US008455867B2

(12) United States Patent
Kim et al.

(10) Patent No.: US 8,455,867 B2
(45) Date of Patent: Jun. 4, 2013

(54) ORGANIC LIGHT-EMITTING DEVICE

(75) Inventors: Young-Kook Kim, Yongin (KR);
Seok-Hwan Hwang, Yongin (KR);
Hye-Jin Jung, Yongin (KR); Jin-O Lim, Yongin (KR); Sang-Hyun Han, Yongin (KR); Yoon-Hyun Kwak, Yongin (KR);
Sun-Young Lee, Yongin (KR);
Jong-Hyuk Lee, Yongin (KR);
Sung-Chul Kim, Yongin (KR)

(73) Assignee: Samsung Display Co., Ltd.,
Giheung-Gu, Yongin, Gyeonggi-Do (KR)

( * ) Notice: Subject to any disclaimer, the term of this patent is extended or adjusted under 35 U.S.C. 154(b) by 83 days.

(21) Appl. No.: 13/078,809

(22) Filed: Apr. 1, 2011

(65) Prior Publication Data

US 2012/0097924 A1 Apr. 26, 2012

(30) Foreign Application Priority Data

Oct. 26, 2010 (KR) ........................ 10-2010-0104736
Mar. 29, 2011 (KR) ........................ 10-2011-0028214

(51) Int. Cl.
*H01L 51/00* (2006.01)
(52) U.S. Cl.
USPC 257/40; 257/103; 257/E51.018; 257/E51.026; 257/E51.028; 548/416; 548/418; 548/518; 428/690

(58) Field of Classification Search
USPC .................. 257/40, 103, E51.018, E51.026, 257/E51.028; 548/416, 418, 518; 428/690
See application file for complete search history.

(56) References Cited

U.S. PATENT DOCUMENTS

| | | | |
|---|---|---|---|
| 3,291,771 | A | 12/1966 | Altermatt |
| 5,635,308 | A | 6/1997 | Inoue et al. |
| 5,645,948 | A | 7/1997 | Shi et al. |
| 5,972,247 | A | 10/1999 | Shi et al. |
| 6,465,115 | B2 | 10/2002 | Shi et al. |
| 6,596,415 | B2 | 7/2003 | Shi et al. |
| 7,989,644 | B2 | 8/2011 | Tanabe et al. |
| 8,247,089 | B2 * | 8/2012 | Otsu et al. ............ 428/690 |
| 2004/0076853 | A1 | 4/2004 | Jarikov |
| 2006/0210830 | A1 | 9/2006 | Funahashi et al. |
| 2007/0155991 | A1 | 7/2007 | Funahashi |
| 2008/0124455 | A1 | 5/2008 | Shin et al. |
| 2008/0203905 | A1 | 8/2008 | Je et al. |
| 2008/0268283 | A1 | 10/2008 | Funahashi |
| 2008/0306303 | A1 | 12/2008 | Rostovtsev et al. |
| 2009/0096393 | A1 | 4/2009 | Taniguchi et al. |
| 2010/0073602 | A1 | 3/2010 | Akino |

FOREIGN PATENT DOCUMENTS

| | | |
|---|---|---|
| JP | 05-339565 | 12/1993 |
| JP | 08-012600 | 1/1996 |
| JP | 1996-012600 | 1/1996 |
| JP | 2000-003782 | 1/2000 |
| JP | 2006-052324 A | 2/2006 |
| JP | 2008-078362 A | 4/2008 |
| JP | 2008-218987 A | 9/2008 |
| JP | 2008-290999 A | 12/2008 |
| JP | 2010-073987 A | 4/2010 |
| KR | 10-2010-0108924 A | 10/2010 |
| KR | 2011-0039108 A | 4/2011 |
| WO | 2008-150872 A1 | 12/2008 |
| WO | 2009-008354 | 1/2009 |
| WO | 2010-053210 A1 | 5/2010 |
| WO | 2010-114264 A2 | 7/2010 |

OTHER PUBLICATIONS

Hwang et al. "Highly efficient and versatile synthesis of polarylfluorenes via pd-catalyzed c-h bond activation." Organic Letters. vol. 11, No. 20 (4588-4591), (2009).
Henriques et al. "Characterization of the coke formed during o-xylene isomerization over mordenites at various tempereatures." Journal of Catalysis 172 (436-445), (1997).
Liu et al. "Facile synthesis of spirocyclic aromatic hydrocarbon derivatives based on o-halobiaryl route and domino reaction for deep-blue organic semiconductors." Organic Letters. vol. 11, No. 17 (3850-3853), (2009).
U.S. Appl. No. 13/,078,080, filed Apr. 1, 2011.
U.S. Appl. No. 13/077,467, filed Mar. 31, 2011.
Korean Office Action issued by Korean Patent Office on Feb. 23, 2013 corresponding to Korean Patent Application No. 10-2011-0028214 and Request for Entry of the Accompanying Office Action attached herewith.

\* cited by examiner

*Primary Examiner* — Tu-Tu Ho
(74) *Attorney, Agent, or Firm* — Robert E. Bushnell, Esq.

(57) ABSTRACT

A heterocyclic compound represented by a general Formula 1 and an organic light-emitting device including the heterocyclic compound. In some embodiments the heterocyclic compound of Formula 1 may be used as a light-emitting material, a hole transporting material, or an electron transporting material. The heterocyclic compound of Formula 1 having a heterocyclic group in the molecules thereof has a high glass transition temperature (Tg) or a high melting point due to the inclusion of the heterocyclic group. Thus, the heterocyclic compound has high heat resistance against Joule's heat generated in an organic layer, between organic layers, or between an organic layer and a metal electrode when light emission occurs, and has high durability in high-temperature environments. An organic light-emitting device manufactured using the heterocyclic compound of Formula 1 has high durability when stored or operated. In addition, due to the inclusion of a substituent such as an aryl group or heteroaryl group, molecular layers formed as thin films may be maintained in good condition, thereby improving the characteristics of the organic light-emitting device.

28 Claims, 2 Drawing Sheets

ORGANIC LIGHT-EMITTING DEVICE

PRIORITY CLAIM

This application claims the benefit of Korean Patent Application No. 10-2011-0028214 filed on Mar. 29, 2011 and Korean Patent Application No. 10-2010-0104736, filed on Oct. 26, 2010, in the Korean Intellectual Property Office, the disclosures of which are each incorporated herein by reference in their entirety.

BACKGROUND OF THE INVENTION

1. Field of the Invention

The present invention relates to a heterocyclic compound represented by Formula 1 and an organic light-emitting device including the heterocyclic compound.

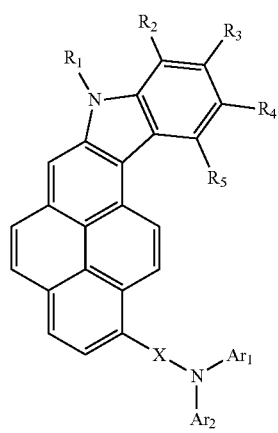

Formula 1

2. Description of the Related Art

Light-emitting devices are self-emitting display devices and have a wide viewing angle, a high contrast ratio, and a short response time. Due to these characteristics, light-emitting devices are drawing more attention.

SUMMARY OF THE INVENTION

The present invention provides heterocyclic compounds having improved electrical characteristics, charge transporting capabilities, light-emission capabilities, and a high glass-transition temperature that is high enough to prevent crystallization.

The present invention provides an organic light-emitting device including the heterocyclic compound.

The present invention provides a flat panel display device including the organic light-emitting device.

According to an aspect of the present invention, there is provided a heterocyclic compound represented by Formula 1 below:

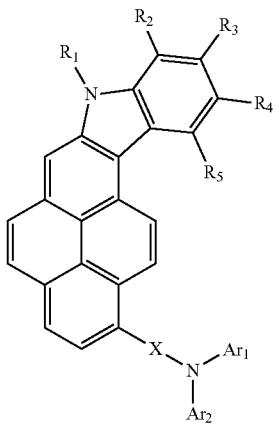

Formula 1 wherein, in Formula 1. $R_1$ through $R_5$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted C3-C60 cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a amino group substituted with a $C_5$-$C_{60}$ aryl or $C_3$-$C_{60}$ heteroaryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, or a carboxyl group:

$Ar_1$ and $Ar_2$ are each independently a substituted or unsubstituted $C_3$-$C_{50}$ cycloalkyl group, a substituted or unsubstituted $C_5$-$C_{60}$ aryloxy group, a substituted or unsubstituted $C_5$-$C_{60}$ arythio group, a substituted or unsubstituted $C_5$-$C_{60}$ aryl group, a amino group substituted with a $C_5$-$C_{60}$ aryl or $C_3$-$C_{60}$ heteroaryl group, a substituted or unsubstituted $C_3$-$C_{60}$ heteroaryl group, or a substituted or unsubstituted $C_6$-$C_{60}$ condensed polycyclic group; and X is a divalent linking group represented by —$(Ar_3)_n$— where $Ar_3$ is a substituted or unsubstituted $C_5$-$C_{60}$ arylene group, a substituted or unsubstituted $C_3$-$C_{60}$ heteroarylene group, or a substituted or unsubstituted $C_6$-$C_{60}$ condensed polycyclic group, and n is an integer from 1 to 10, wherein n groups of $Ar_3$ are identical to or different from each other, and at least two adjacent groups of the n $Ar_3$ groups are fused or linked to each other by a single bond.

In Formula 1 above, $R_1$ to $R_5$ may be each independently a hydrogen atom, a deuterium atom, a cyano group, a halogen atom, an unsubstituted $C_1$-$C_{20}$ alkyl group, a substituted $C_1$-$C_{20}$ alkyl group with at least one fluorine (—F) substituent, a substituted or unsubstituted $C_5$-$C_{20}$ aryl group, or a substituted or unsubstituted $C_3$-$C_{20}$ heteroaryl group.

In Formula 1 above, $R_1$ to $R_5$ may be each independently a hydrogen atom, a deuterium atom, a halogen atom, a cyano group, a substituted or unsubstituted $C_1$-$C_{20}$ alkyl group, or groups represented by Formulae 2a to 2f below:

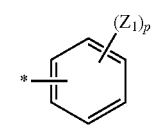

formula 2a

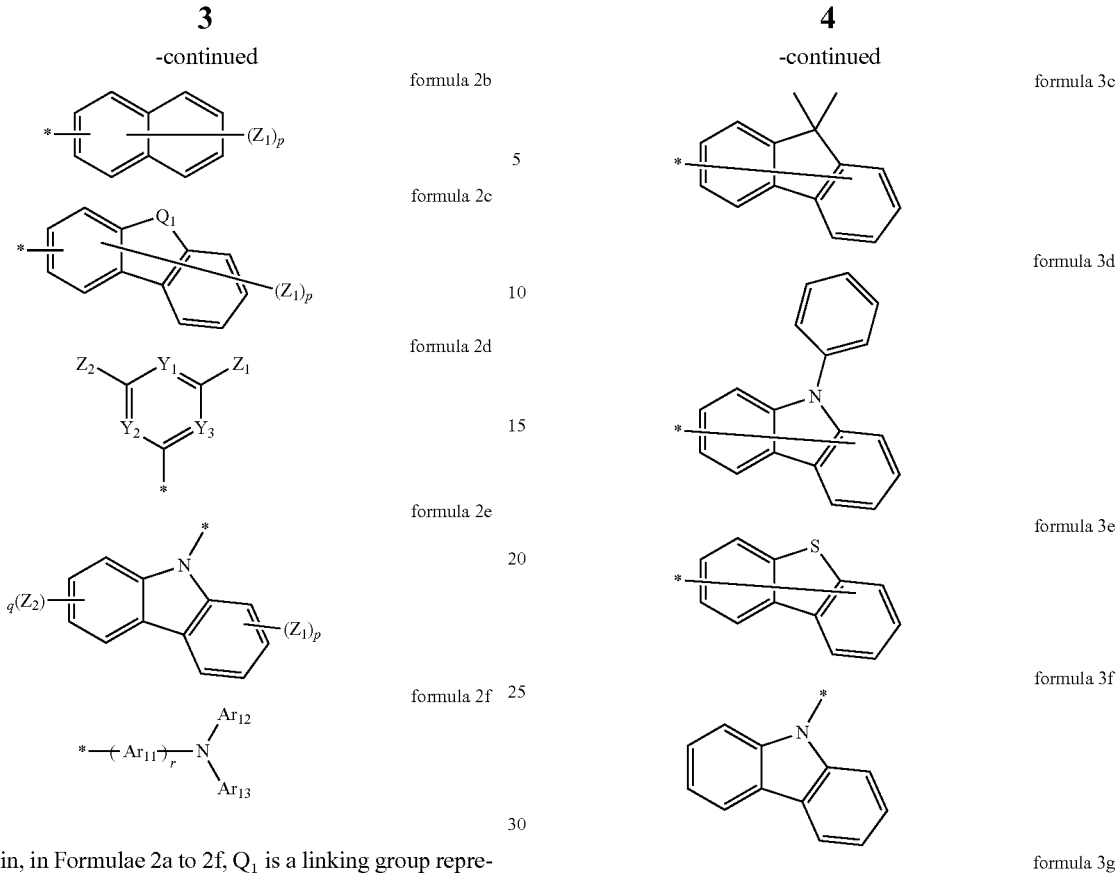

wherein, in Formulae 2a to 2f, $Q_1$ is a linking group represented by $-C(R_6)(R_7)-$, $-N(R_6)-$, $-S-$, or $-O-$;

$Y_1$, $Y_2$, and $Y_3$ are each independently a linking group represented by $-N=$ or $-C(R_8)=$;

$Z_1$, $Z_2$, $Ar_{12}$, $Ar_{13}$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

$Ar_{11}$ is a substituted or unsubstituted alkylene group, a substituted or unsubstituted $C_5$-$C_{20}$ arylene group, or a substituted or unsubstituted $C_3$-$C_{20}$ heteroarylene group;

p is an integer from 1 to 12;

q is an integer from 1 to 12;

r is an integer from 0 to 5: and

* indicates a binding site.

In Formula 1 above, $R_1$ to $R_5$ may be each independently a hydrogen atom, a deuterium atom, a halogen atom, a cyano group, a methyl group, an ethyl group, a propyl group, a butyl group, a pentyl group, or groups represented by Formulae 3a to 3h below:

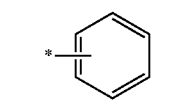

formula 3a

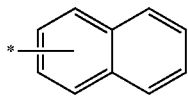

formula 3b wherein in Formula 3a to 3h, $Ar_{12}$ and $Ar_{13}$ are each independently an unsubstituted aryl group, a substituted or unsubstituted $C_3$-$C_{20}$ heteroaryl group, or a substituted or unsubstituted $C_6$-$C_{20}$ condensed polycyclic group;

r is an integer from 0 to 2; and

* indicates a binding site.

In Formula 1 above, $R_2$ and $R_5$ may be hydrogen atoms; and $R_1$, $R_3$, and $R_4$ may be each independently a hydrogen atom, a deuterium atom, a halogen atom, a cyano group, a methyl group, an ethyl group, a propyl group, a butyl group, a pentyl group, or groups is represented by Formulae 3a to 3h below:

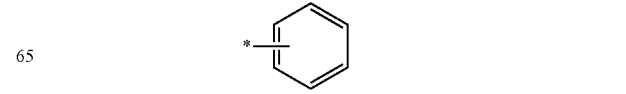

formula 3a

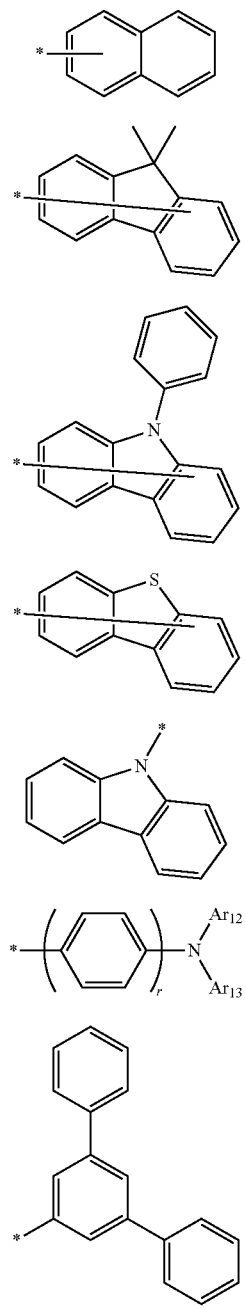

In Formula 1 above, $Ar_1$ and $Ar_2$ may be each independently a group represented by one of Formulae 4a to 4d below:

formula 4a formula 4b formula 4c formula 4d wherein, in Formula 4a to 4d, $Q_1$ is a linking group represented by $—C(R_6)(R_7)—$, $—N(R_6)—$, $—S—$, or $—O—$;

$Y_1$, $Y_2$, and $Y_3$ are each independently a linking group represented by $—N=$ or $—C(R_8)=$;

$Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

p is an integer from 1 to 8; and

* indicates a binding site.

In Formula 1 above, $Ar_1$ and $Ar_2$ may be each independently a group represented by one of Formulae 5a to 5i below:

formula 5 formula 5b formula 5c formula 5d wherein, in Formula 3a to 3h, $Ar_{12}$ and $Ar_{13}$ are each independently an unsubstituted aryl group, a substituted or unsubstituted $C_3$-$C_{20}$ heteroaryl group, or a substituted or unsubstituted $C_6$-$C_{20}$ condensed polycyclic group: r is an integer from 0 to 2; and * indicates a binding site.

In Formula 1 above, $R_2$ and $R_5$ may be hydrogen atoms; and $R_1$, $R_3$ and $R_4$ may be each independently a substituted or unsubstituted $C_1$-$C_{20}$ alkyl group, a substituted or unsubstituted $C_6$-$C_{20}$ aryl group, or a substituted or unsubstituted $C_3$-$C_{20}$ heteroaryl group.

In Formula 1 above, $Ar_1$ and $Ar_2$ may be each independently a substituted or unsubstituted $C_1$-$C_{20}$ alkyl group, a substituted or unsubstituted $C_5$-$C_{20}$ aryl group, or a substituted or unsubstituted $C_3$-$C_{20}$ heteroaryl group.

formula 5e
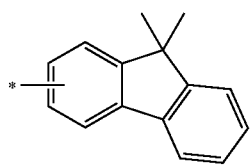

formula 5f
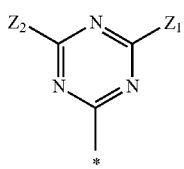

formula 5g
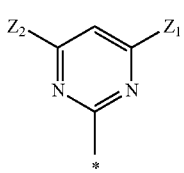

formula 5h
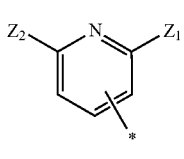

formula 5i
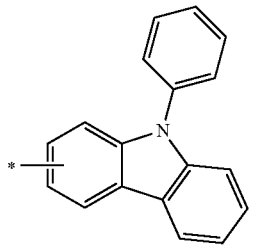

wherein $Z_1$ and $Z_2$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, or a substituted or unsubstituted $C_6$-$C_{20}$ condensed polycyclic group; and * indicates a binding site.

$Ar_3$ for X in Formula 1 may be a substituted or unsubstituted $C_5$-$C_{20}$ arylene group, a substituted or unsubstituted $C_3$-$C_{20}$ heteroarylene group, or a substituted or unsubstituted $C_6$-$C_{20}$ condensed polycyclic group.

$Ar_3$ for X in Formula 1 may include a group represented by one of Formulae 6a to 6e below:

formula 6a
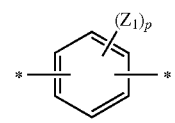

formula 6b
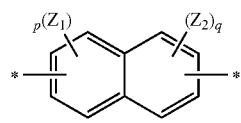

formula 6c
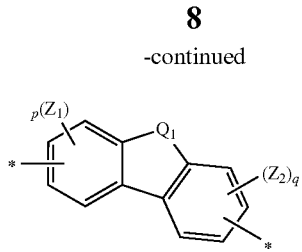

formula 6d
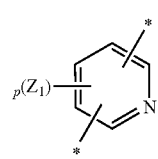

formula 6e
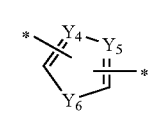

wherein, in Formula 6a to 6e, $Q_1$ is a linking group represented by —C($R_6$)($R_7$)—, —N($R_6$)—, or —S—;

$Y_4$, $Y_5$, and $Y_6$ are each independently a linking group represented by —N= or —C($R_8$)=, —S—, or —O—;

$Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group:

p is an integer from 1 to 8;

q is an integer from 1 to 8; and

* indicates a binding site.

In Formula 1 above, n may be 1 or 2.

In Formula 1, X may include a group represented by one of Formulae 7a to 7j:

formula 7a
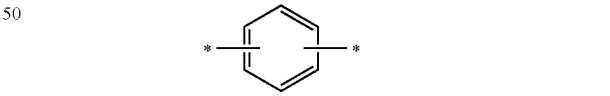

formula 7b
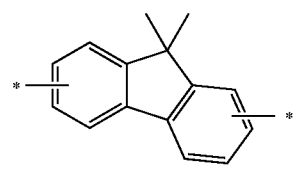

formula 7c
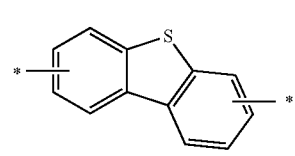

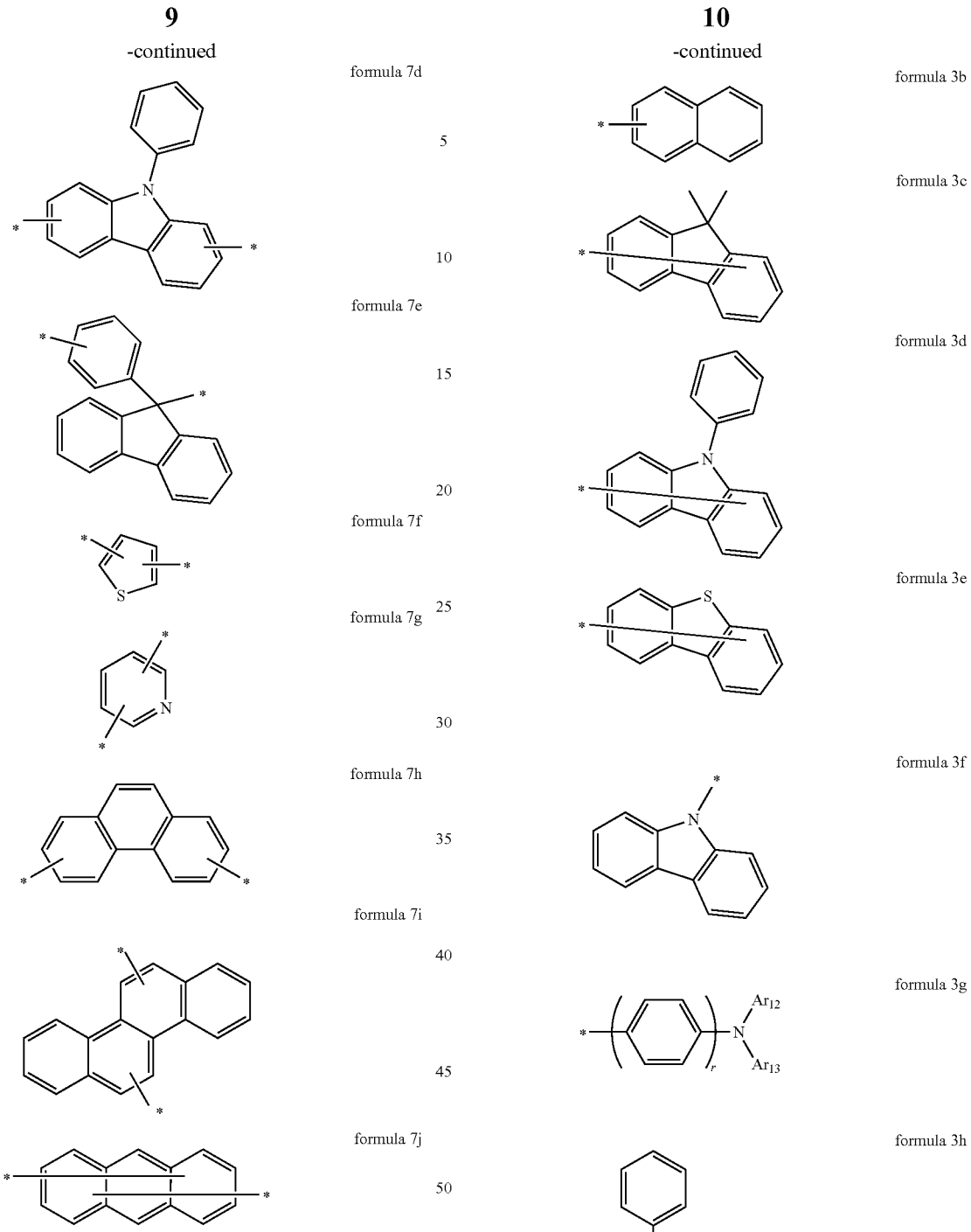

wherein, in Formula 7a to 7j, * indicates a binding site.

In Formula 1 above, $R_1$, $R_3$, and $R_4$ may be each independently a hydrogen atom, a deuterium atom, a halogen atom, a cyano group, a methyl group, an ethyl group, a propyl group, a butyl group, a pentyl group, or groups represented by Formulae 3a to 3h below:

formula 3a

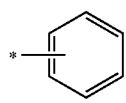

wherein, in Formula 3a to 3h, $Ar_{12}$ and $Ar_{13}$ are each independently an unsubstituted aryl group, a substituted or unsubstituted $C_3$-$C_{20}$ heteroaryl group, or a substituted or unsubstituted $C_6$-$C_{20}$ condensed polycyclic group; r is an integer from 0 to 2, and * indicates a binding site;

$R_2$ and $R_5$ are hydrogen atoms;

Ar$_3$ comprises a group represented by one of Formulae 6a to 6e below:

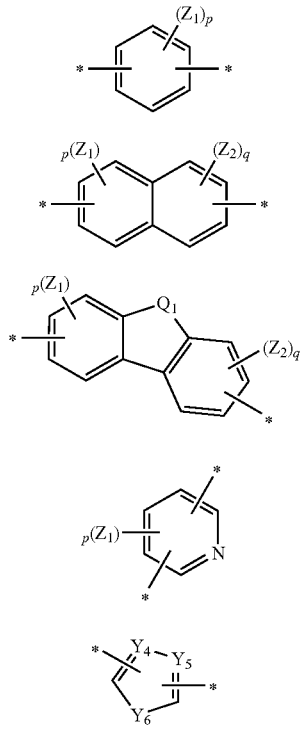

formula 6a formula 6b formula 6c formula 6d formula 6e wherein, in Formulae 6a to 6e, Q$_1$ is a linking group represented by —C(R$_6$)(R$_7$)—, —N(R$_6$)—, or —S—; Y$_4$, Y$_5$ and Y$_6$ are each independently a linking group represented by —N=, —C(R$_8$)=, —S—, or —O—; Z$_1$, Z$_2$, R$_6$, R$_7$, and R$_8$ are each independently a hydrogen atom, a deuterium atom, a substituted or unsubstituted C$_1$-C$_{20}$ alkyl group, a substituted or unsubstituted C$_5$-C$_{20}$ aryl group, a substituted or unsubstituted C$_3$-C$_{20}$ heteroaryl group, a substituted or unsubstituted C$_6$-C$_{20}$ condensed polycyclic group, a halogen atom, a cyano group, a nitro group, a hydroxyl group, or a carboxy group; p is an integer from 1 to 8; q is an integer from 1 to 8; and * indicates a binding site;

n in Formula 1 is 1 or 2; and

Ar$_1$ and Ar$_2$ are each independently selected from among groups represented by Formulae 4a to 4d below:

formula 4a formula 4b formula 4c

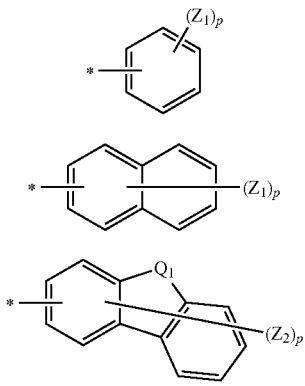

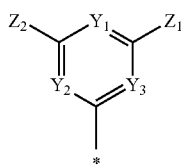

formula 4d wherein, in Formulae 4a to 4d, Q$_1$ is a linking group represented by —C(R$_6$)(R$_7$)—, —N(R$_6$)—, —S—, or —O—; Y$_1$, Y$_2$ and Y$_3$ are each independently a linking group represented by —N= or —C(R$_8$)=; Z$_1$, Z$_2$, R$_6$, R$_7$, and R$_8$ are each independently a hydrogen atom, a deuterium atom, a substituted or unsubstituted C$_1$-C$_{20}$ alkyl group, a substituted or unsubstituted C$_5$-C$_{20}$ aryl group, a substituted or unsubstituted C$_3$-C$_{20}$ heteroaryl group, a substituted or unsubstituted C$_6$-C$_{20}$ condensed polycyclic group, a halogen atom, a cyano group, a nitro group, a hydroxyl group, or a carboxy group; p is an integer from 1 to 8; and * indicates a binding site.

The heterocyclic compound may include one of the compounds below:

3

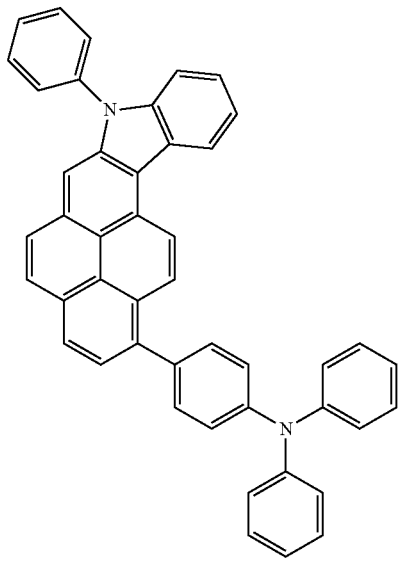

5

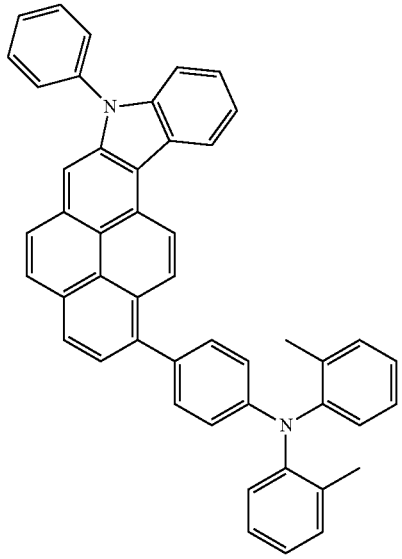

11
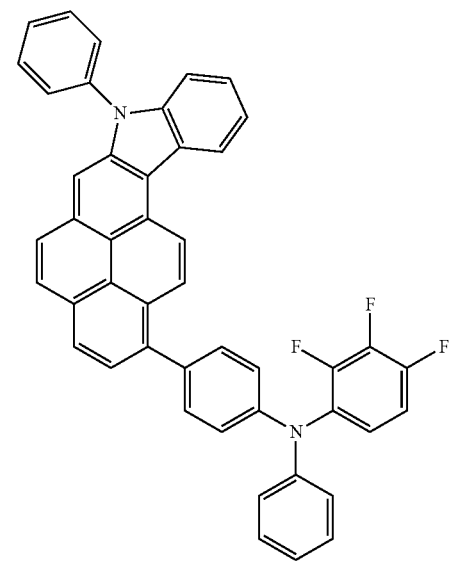
21
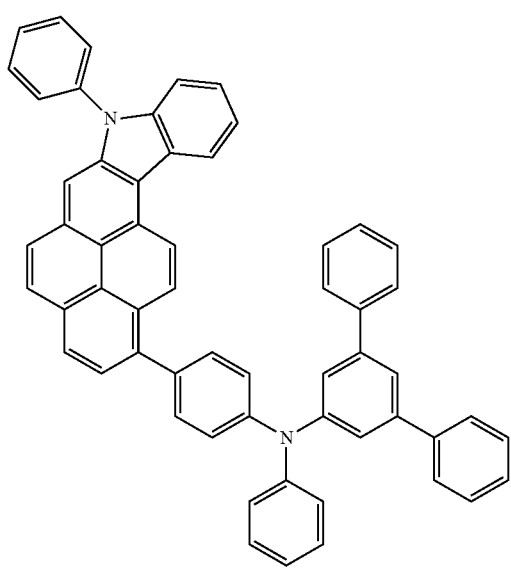
24
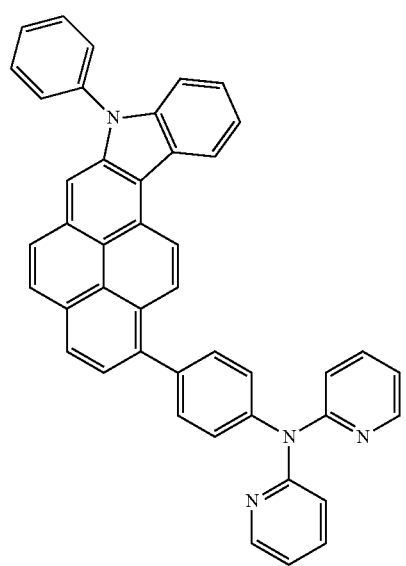
40
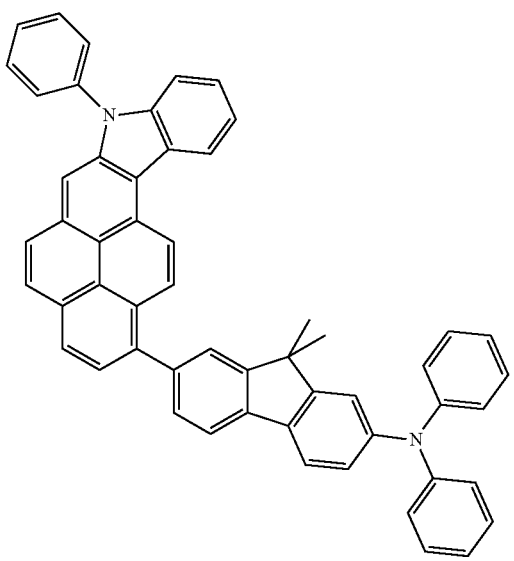
58
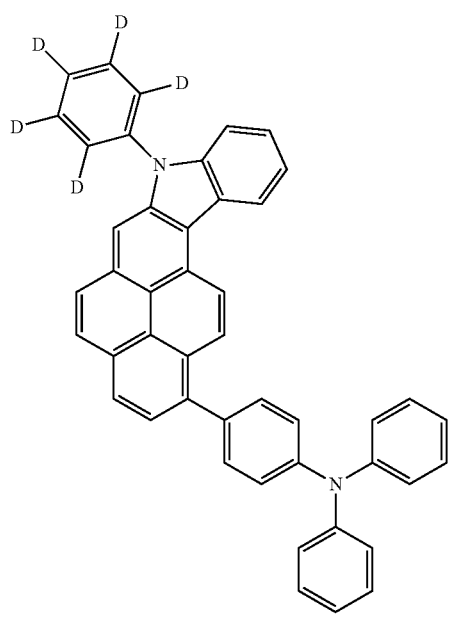

-continued

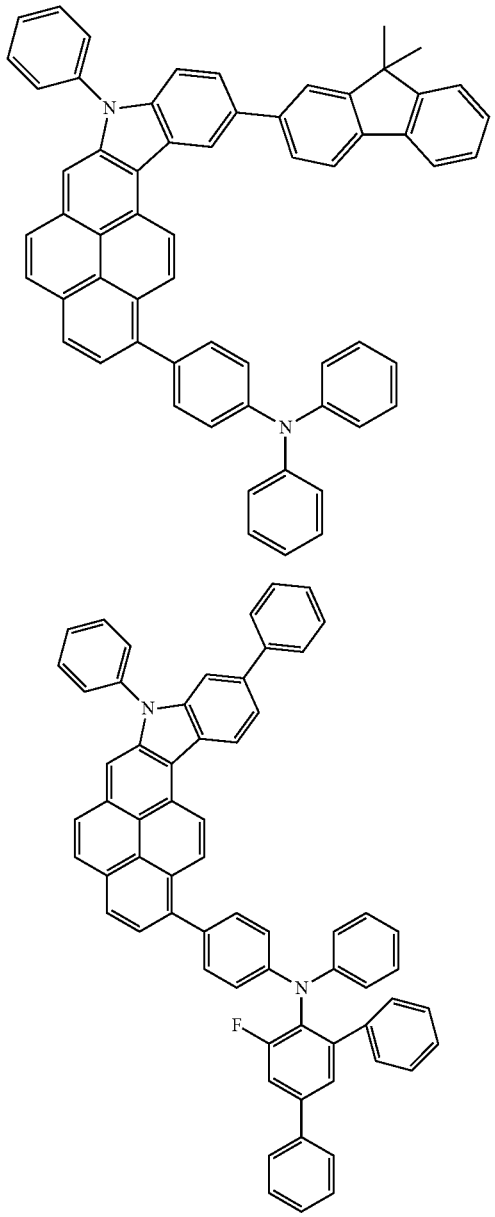

According to another aspect of the present invention, an organic light-emitting device includes: a first electrode; a second electrode; and an organic layer between the first electrode and the second electrode, wherein the organic layer includes a heterocyclic compound represented by Formula 1 above.

The organic layer may include a hole injection layer, a hole transport layer, a functional layer having both hole injection and hole transport capabilities, an electron injection layer, an electron transport layer, a functional layer having both electron injection and electron transport capabilities or any combination thereof.

The organic layer may include an emission layer, and the heterocyclic compound of Formula 1 may be used as a host or a dopant for a fluorescent or phosphorescent device.

The organic layer may include an emission layer, a hole transport layer, and an electron transport layer. The emission layer, the hole transport layer, or the electron transport layer may include the heterocyclic compound of Formula 1. The emission layer may include an anthracene compound, an arylamine compound, or a styryl compound.

The organic layer may include an emission layer, a hole transport layer, and an electron transport layer. The emission layer, the hole transport layer, or the electron transport layer may include the heterocyclic compound of Formula 1. The emission layer may include red, green, blue, and white emission layers, one of which includes a phosphorescent compound.

The organic layer may include a blue emission layer.

The organic layer may include a blue emission layer, and the heterocyclic compound of Formula 1 may be used as a blue dopant.

The organic layer may include at least one organic layer including the heterocyclic compound of Formula 1 above, the at least one organic layer being formed using a wet process.

According to another aspect of the present invention, a flat panel display device includes the organic light-emitting device according to the one or more embodiments described above, wherein the first electrode of the organic light-emitting device may be electrically connected to a source electrode or a drain electrode of a thin-film transistor.

BRIEF DESCRIPTION OF THE DRAWING

The above and other features and advantages of the present invention will become more apparent by a detailed description of exemplary embodiments thereof with reference to the attached drawings in which.

DETAILED DESCRIPTION OF THE INVENTION

Figure 1:
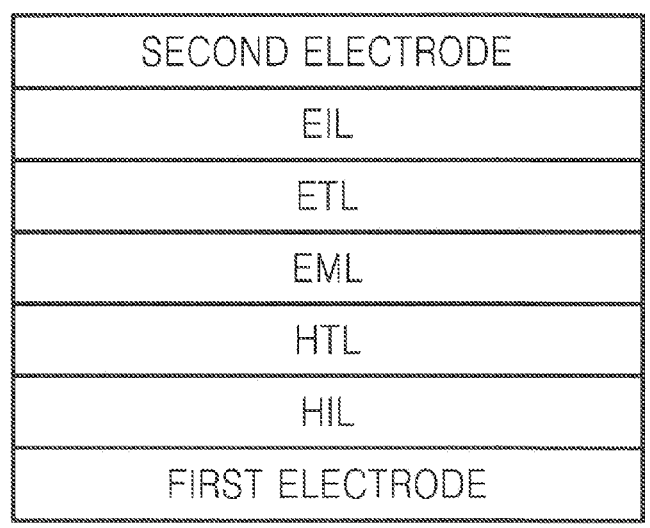
FIG. 1 illustrates the structure of an organic light-emitting device according to an embodiment of the present invention.
Figure 2:
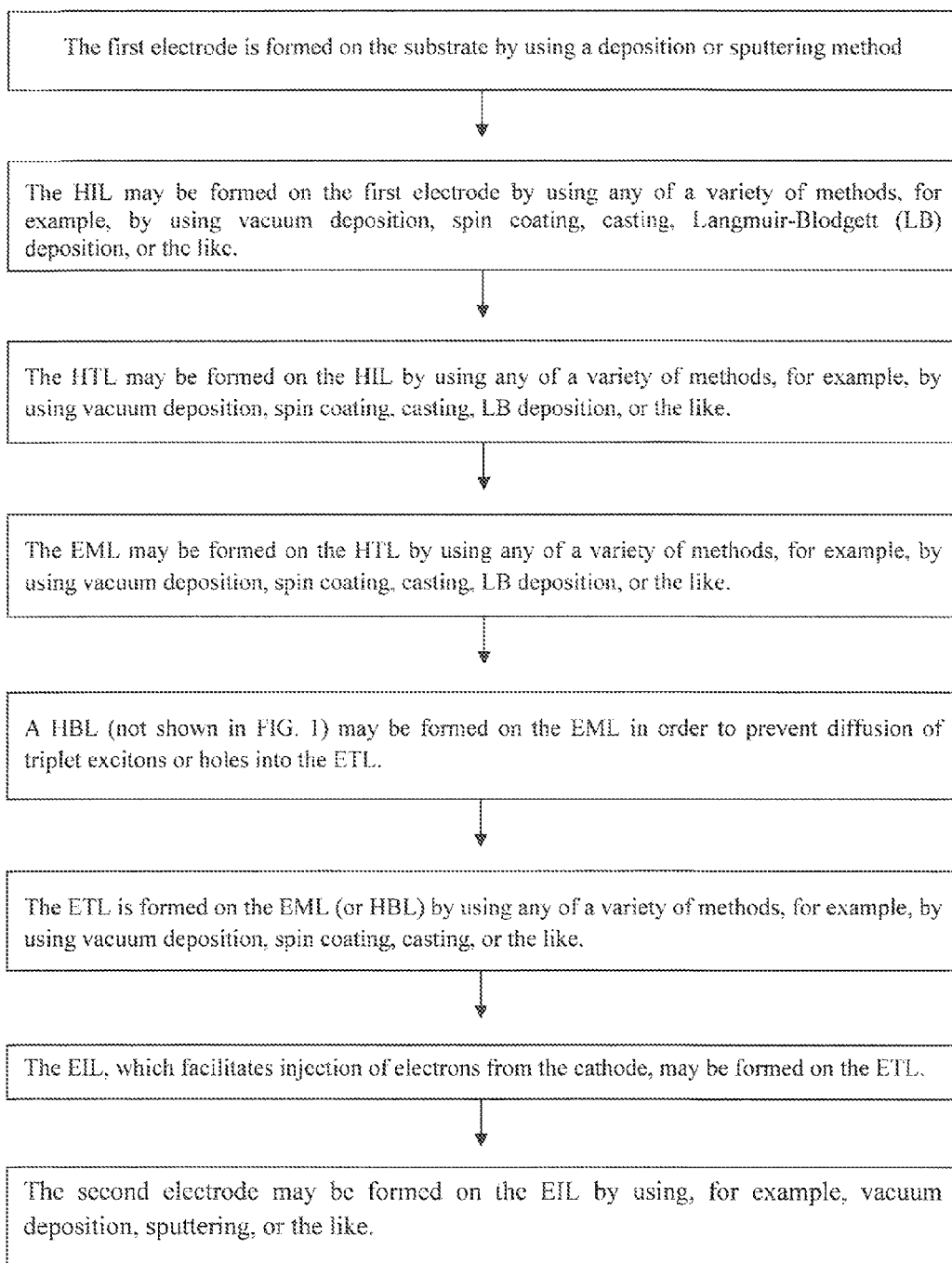
FIG. 2 illustrates the preparation of an organic light emitting device according to an embodiment of the present invention.

Organic light-emitting devices can be roughly classified as either inorganic light-emitting devices that include emission layers containing inorganic compounds, or organic light-emitting devices that include emission layers containing organic compounds.

Specifically, organic light-emitting devices have higher luminance, lower driving voltages, and shorter response times than inorganic light-emitting devices, and can render multi-colored displays. Thus, much research into such organic light-emitting devices has been conducted.

Typically, an organic light-emitting device has a stack structure including an in anode, a cathode and an organic emission layer interposed therebetween. However, a hole injection layer, a hole transport layer, an electron transport layer, or an electron injection layer may be further stacked between either the anode or the cathode and the organic emission layer. In other words, an organic light-emitting device may have a stack structure of anode/hole transport layer/organic emission layer/cathode or a stack structure of anode/hole transport layer/organic emission layer/electron transport layer/cathode.

As a material for forming the organic emission layer, naphthalene derivatives can be used. However, organic light-emitting devices including such materials may not have satisfactory life span, efficiency, and power consumption characteristics, therefore improvement in this regard is still necessary.

An organic light-emitting device manufactured using a compound of phenylanthracene dimer or trimer as an organic emission layer material is widely known. However, such organic light-emitting devices have a narrow energy gap and lower blue-light color purity since two or three oligomeric species of anthracene are linked by conjugation. In addition, such compounds are highly vulnerable to oxidation and thus are liable to produce impurities, necessitating purification. In order to overcome these drawbacks, organic light-emitting devices manufactured using an anthracene compound including naphthalene substituted for anthracene at the 1, 9 positions or using a diphenylanthracene compound including an aryl group substituted for a phenyl group at the m-position have been introduced. However, these organic light-emitting devices have a lower light-emission efficiency.

Organic light-emitting devices may also be manufactured using naphthalene-substituted monoanthracene derivatives. However, the light-emission efficiency thereof is low at about 1 cd/A, and thus such organic light-emitting devices are not suitable for practical use.

Furthermore, organic light-emitting devices may be manufactured using phenylanthracene compounds including aryl substituents at the m-position. Such a compound has excellent thermal resistance but leads to an unsatisfactorily low light-emission efficiency of about 2 cd/A.

The present invention will now be described more fully with reference to the accompanying drawings, in which exemplary embodiments of the invention are shown.

A heterocyclic compound according to an embodiment of the present invention is represented by Formula 1 below:

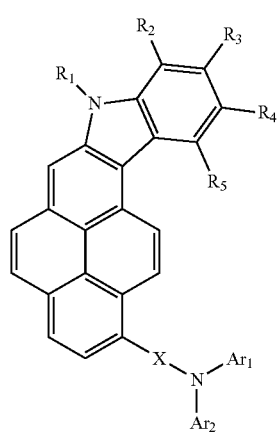

Formula 1

In Formula 1, $R_1$ through $R_5$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a amino substituted group with a $C_5$-$C_{60}$ aryl or $C_3$-$C_{60}$ heteroaryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, or a carboxyl group;

$Ar_1$ and $Ar_2$ are each independently a substituted or unsubstituted $C_3$-$C_{50}$ cycloalkyl group, a substituted or unsubstituted $C_5$-$C_{60}$ aryloxy group, a substituted or unsubstituted $C_5$-$C_{60}$ arythio group, a substituted or unsubstituted $C_5$-$C_{60}$ aryl group, a amino group substituted with a $C_3$-$C_{60}$ aryl or $C_3$-$C_{60}$ heteroaryl group, a substituted or unsubstituted $C_3$-$C_{60}$ heteroaryl group, or a substituted or unsubstituted $C_6$-$C_{60}$ condensed polycyclic group; and X is a divalent linking group represented by —$(Ar_3)_6$— where $Ar_3$ is a substituted or unsubstituted $C_5$-$C_{60}$ arylene group, a substituted or unsubstituted $C_3$-$C_{14}$) heteroarylene group, or a substituted or unsubstituted $C_6$-$C_{60}$ condensed polycyclic group, and n is an integer from 1 to 10, wherein n groups of $Ar_3$ may be identical to or different from each other, and at least two adjacent groups of the n $Ar_3$ groups may be fused or linked to each other by a single bond.

In some embodiments the heterocyclic compound of Formula 1 may be used as a light-emitting material, a hole transporting material, or an electron transporting material. Having improved performance as blue-emitting material, the compound of Formula 1 may be useful as a deep blue material in a large display having a non-resonant structure. The heterocyclic compound of Formula 1 having a heterocyclic group in the molecules thereof has a high glass transition temperature (Tg) or a high melting point due to the inclusion of the heterocyclic group. Thus, the heterocyclic compound has high heat resistance against Joule's heat generated in an organic layer, between organic layers, or between an organic layer and a metal electrode when light emission occurs, and has high durability in high-temperature environments.

An organic light-emitting device manufactured using a heterocyclic compound of Formula 1 has high durability when stored or operated. In addition, due to the inclusion of a substituent such as an aryl group or heteroaryl group, molecular layers formed as thin films may be maintained in good condition, thereby improving the characteristics of the organic light-emitting device.

Substituents in the heterocyclic compound of Formula f will now be described in detail.

$R_1$ to $R_5$ in Formula 1 above may be each independently a hydrogen atom, a deuterium atom, a cyano group, a halogen atom, an unsubstituted $C_1$-$C_{20}$ alkyl group, a substituted $C_1$-$C_{20}$ alkyl group with at least one fluorine (—F) substituent, a substituted or unsubstituted $C_5$-$C_{10}$ aryl group, or a substituted or unsubstituted $C_3$-$C_{20}$ heteroaryl group.

In some embodiments $R_1$ to $R_5$ in Formula 1 may be each independently a hydrogen atom, a deuterium atom, a halogen atom, a cyano group, a substituted or unsubstituted $C_1$-$C_{20}$ alkyl group, or compounds represented by Formulae 2a to 2f below:

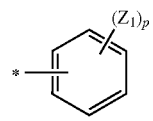

formula 2a

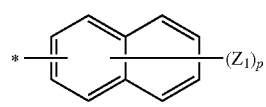

formula 2b

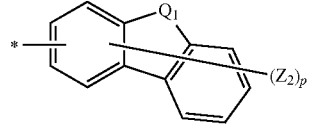

formula 2c

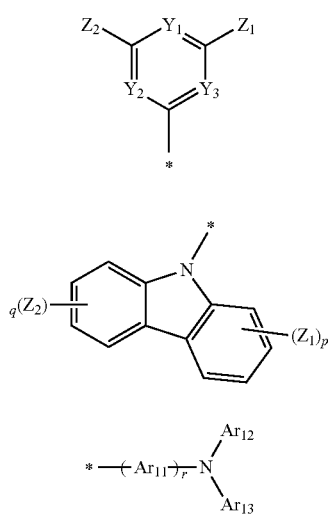

formula 2d formula 2e formula 2f

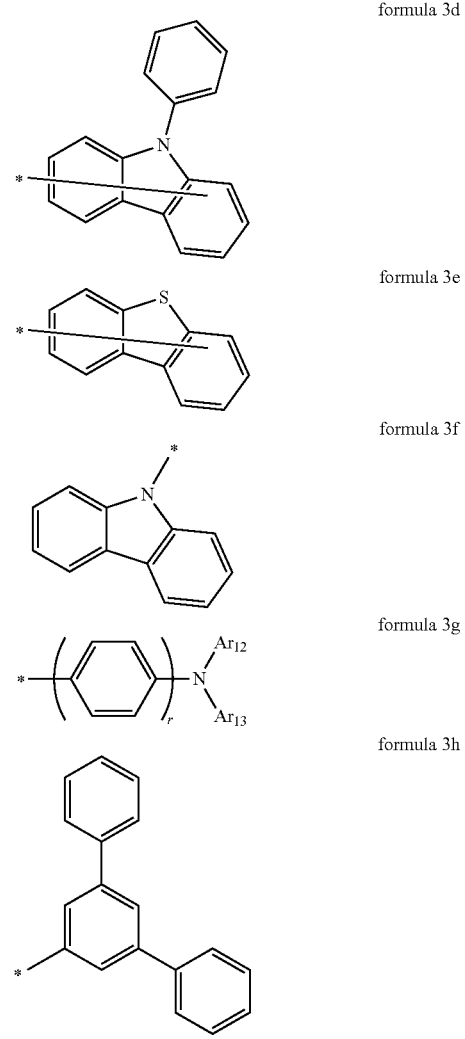

formula 3d formula 3e formula 3f formula 3g formula 3h

In Formula 2a to 2f above, $Q_1$ is a linking group represented by —$C(R_6)(R_7)$—, —$N(R_6)$—, —S—, or —O—; $Y_1$, $Y_2$ and $Y_3$ are each independently a linking group represented by —N= or —$C(R_8)$=;

$Z_1$, $Z_2$, $Ar_{12}$, $Ar_{13}$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

$Ar_{11}$ is a substituted or unsubstituted $C_1$-$C_{20}$ alkylene group, a substituted or unsubstituted $C_5$-$C_{20}$ arylene group, or a substituted or unsubstituted $C_3$-$C_{20}$ heteroarylene group;

p is an integer from 1 to 12; q is an integer from 1 to 12; r is an integer from 0 to 5; and * indicates a binding site.

In some embodiments $R_1$ to $R_5$ in Formula 1 above may be each independently a hydrogen atom, a deuterium atom, a halogen atom, a cyano group, a methyl group, an ethyl group, a propyl group, a butyl group, a pentyl group, or compounds represented by Formulae 3a to 3h below:

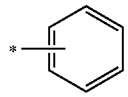

formula 3a

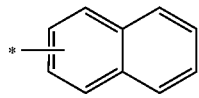

formula 3b

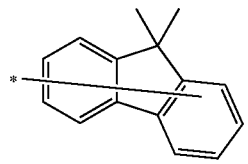

formula 3c

In Formula 3a to 3h above, $Ar_{12}$ and $Ar_{13}$ are each independently an unsubstituted aryl group, a substituted or unsubstituted $C_3$-$C_{20}$ heteroaryl group, or a substituted or unsubstituted $C_6$-$C_{20}$ condensed polycyclic group: r is an integer from 0 to 2; and * indicates a binding site.

In some embodiments $R_2$ and $R_5$ in Formula 1 above may be hydrogen atoms; and $R_1$, $R_3$ and $R_4$ may be each independently a hydrogen atom, a deuterium atom, a halogen atom, a cyano group, a methyl group, an ethyl group, a propyl group, a butyl group, a pentyl group, or compounds represented by Formulae 3a to 3h above.

In some embodiments $R_2$ and $R_5$ in Formula 1 above may be hydrogen atoms; and $R_1$, $R_3$ and $R_4$ may be each independently a substituted or unsubstituted $C_1$-$C_{20}$alkyl group, a 11 substituted or unsubstituted $C_6$-$C_{20}$ aryl group, or a substituted or unsubstituted $C_3$-$C_{20}$ heteroaryl group.

In some embodiments $Ar_1$ and $Ar_2$ in Formula 1 above may be each independently a substituted or unsubstituted $C_1$-$C_{20}$ alkyl group, a substituted or unsubstituted $C_5$-$C_{20}$ aryl group, or a substituted or unsubstituted $C_3$-$C_{20}$heteroaryl group.

In some other embodiments $Ar_1$ and $Ar_2$ in Formula 1 above may be each independently a compound represented by Formulae 4a to 4d below:

formula 4a
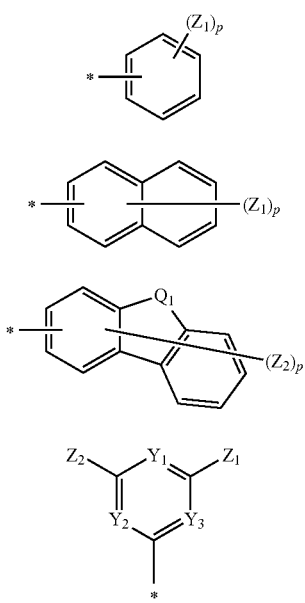
formula 4b formula 4c formula 4d formula 5e
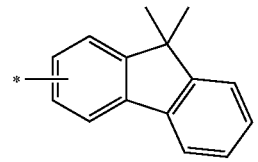

formula 5f
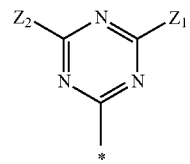

formula 5g
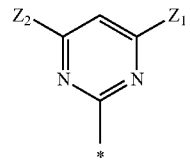

formula 5h
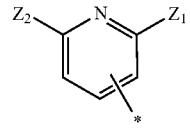

formula 5i
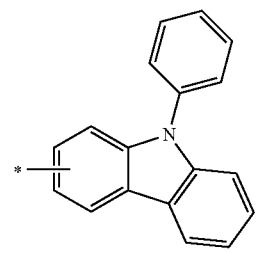

In Formulae 4a to 4d, $Q_1$ is a linking group represented by —C($R_6$)($R_7$)—, —N($R_6$)—, —S—, or —O—; $Y_1$, $Y_2$, and $Y_3$ are each independently a linking group represented by —N= or —C($R_8$)=; $Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p is an integer from 1 to 8; and * indicates a binding site.

In some embodiments $Ar_1$ and $Ar_2$ in Formula 1 above may be each independently a compound represented by one of Formulae 5a to 5i below:

formula 5
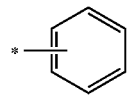

formula 5b
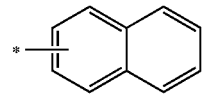

formula 5c
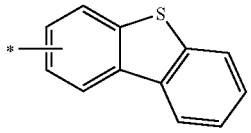

formula 5d
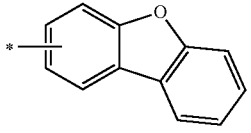

In Formulae 5a to 5i, $Z_1$ and $Z_2$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, or a substituted or unsubstituted $C_6$-$C_{20}$ condensed polycyclic group; and * indicates a binding site.

In some embodiments $Ar_3$ for X in Formula 1 above may be a substituted or unsubstituted $C_5$-$C_{20}$ arylene group, a substituted or unsubstituted $C_3$-$C_{20}$ heteroarylene group, or a substituted or unsubstituted $C_6$-$C_{20}$ condensed polycyclic group.

In some other embodiments $Ar_3$ may be a group represented by one of Formulae 6a to 6e:

formula 6a
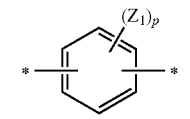

formula 6b
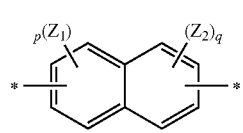

-continued formula 6c

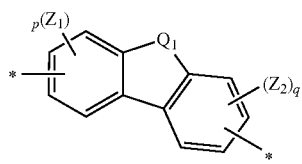

formula 6d

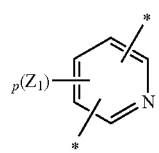

formula 6e

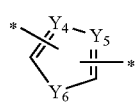

In Formulae 6a to 6e, $Q_1$ is a linking group represented by —C($R_6$)($R_7$)—, —($R_6$)—, or —S—;

$Y_4$, $Y_5$, and $Y_6$ are each independently a linking group represented by —N═ or —C($R_8$)═, —S—, or —O—;

$Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

p is an integer from 1 to 8; q is an integer from 1 to 8; and * indicates a binding site.

In some embodiments n indicating the number of $Ar_3$ groups for X in Formula above may be an integer of 1 or 2, In some embodiments X in Formula 1 above may be a group represented by one of Formulae 7a to 7j:

formula 7a

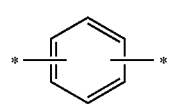

formula 7b

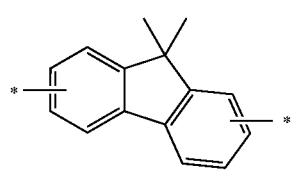

formula 7c

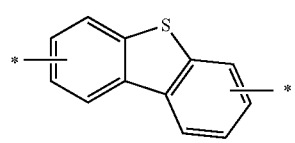

formula 7d

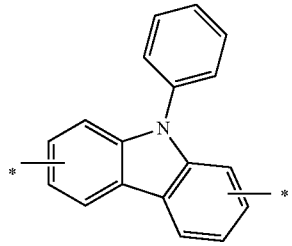

formula 7e

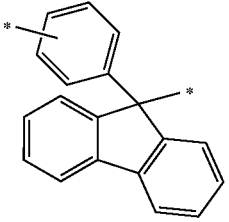

formula 7f

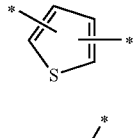

formula 7g

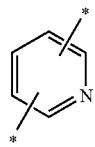

formula 7h

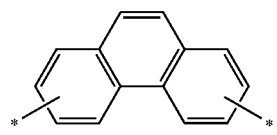

formula 7i

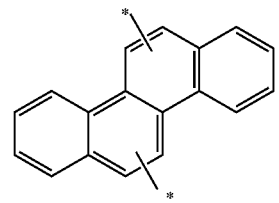

formula 7j

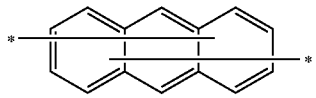

In Formulae 7a to 7j, * indicates a binding site.

In some embodiments $R_1$, $R_3$, and $R_4$ in Formula 1 above may be each independently a hydrogen atom, a deuterium atom, a halogen atom, a cyano group, a methyl group, an ethyl group, a propyl group, a butyl group, a pentyl group, or compounds represented by Formulae 3a to 3h below:

formula 3a

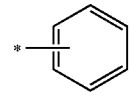

-continued formula 3b
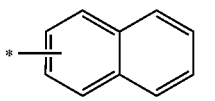

formula 3c
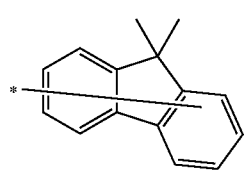

formula 3d
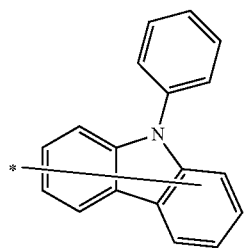

formula 3e
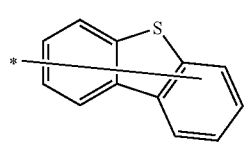

formula 3f
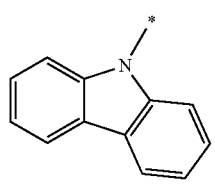

formula 3g
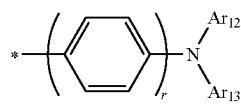

formula 3h
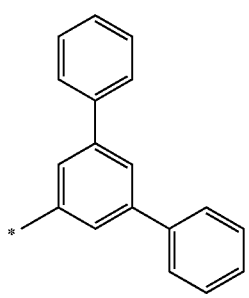

In Formula 3a to 3h above, $Ar_{12}$ and $Ar_{13}$ are each independently an unsubstituted aryl group, a substituted or unsubstituted $C_3$-$C_{20}$ heteroaryl group, or a substituted or unsubstituted $C_6$-$C_{20}$ condensed polycyclic group; r is an integer from 0 to 2, and * indicates a binding site;

$R_2$ and $R_5$ in Formula 1 may be hydrogen atoms;

$Ar_3$ in Formula 1 may be a group represented by one of Formulae 6a to 6e below;

formula 6a
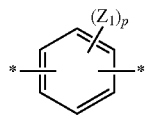

formula 6b
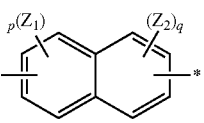

formula 6c
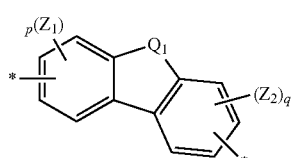

formula 6d
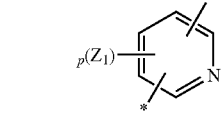

formula 6e
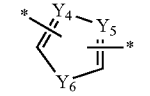

wherein, in Formulae 6a to 6e, $Q_1$ is a linking group represented by —C($R_6$)($R_7$)—, —N($R_6$)—, or —S—; $Y_4$, $Y_5$ and $Y_6$ are each independently a linking group represented by —N=, —C($R_8$)=, —S—, or —O—; $Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p is an integer from 1 to 8; q is an integer from 1 to 8; and * indicates a binding site;

n, which indicates the number of $Ar_3$ groups for X in Formula 1, may be an integer of 1 or 2;

$Ar_1$ and $Ar_2$ in Formula 1 may be each independently a compound represented by one of Formulae 4a to 4d below:

formula 4a
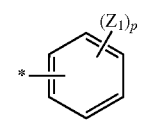

formula 4b
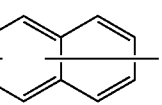

formula 4c
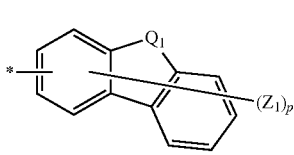

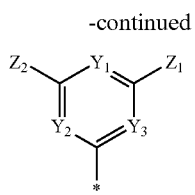

formula 4d wherein, in Formulae 4a to 4e, $Q_1$ is a linking group represented by $-C(R_6)(R_7)-$, $-N(R_6)-$, $-S-$, or $-O-$; $Y_1$, $Y_2$ and $Y_3$ are each independently a linking group represented by $-N=$ or $-C(R_8)=$; $Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p is an integer from 1 to 8; and * indicates a binding site.

Hereinafter, substituents described with reference to Formulae 1 to 7J will now be described in detail. In this regard, the numbers of carbons in substituents are presented only for illustrative purposes and do not limit the characteristics of the substituents The unsubstituted $C_1$-$C_{60}$ alkyl group used herein may be linear or branched. Examples of the alkyl group may include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom of the alkyl group may be substituted with heavy hydrogen atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_3$-$C_{16}$; heteroaryl group.

The unsubstituted $C_2$-$C_{60}$ alkenyl group indicates an unsaturated alkyl groups having at least one carbon-carbon double bond in the center or at a terminal of the alkyl group. Examples of the alkenyl group include an ethenyl group, a propenyl group, a butenyl group, and the like. At least one hydrogen atom in the unsubstituted alkenyl group may be substituted with a substituent described above in conjunction with the alkyl group.

The unsubstituted $C_2$-$C_{60}$ alkynyl group indicates an alkyl group having at least one carbon-carbon triple bond in the center or at a terminal of the alkyl group. Examples of the unsubstituted $C_2$-$C_{20}$ alkynyl group include acetylene, propylene, phenylacetylene, naphthylacetylene, isopropylacetylene, t-butylacetylene, diphenylacetylene, and the like. At least one hydrogen atom in the alkynyl group may be substituted with a substituent described above in conjunction with the alkyl group.

The unsubstituted $C_3$-$C_{60}$ cycloalkyl group indicates a $C_3$-$C_{60}$ cyclic alkyl group wherein at least one hydrogen atom in the cycloalkyl group may be substituted with a substituent described above in connection with the $C_1$-$C_{60}$ alkyl group.

The unsubstituted $C_1$-$C_{60}$ alkoxy group indicate's a group having a structure of $-OA$ wherein A is an unsubstituted $C_1$-$C_{60}$ alkyl group as described above. Nonlimiting examples of the unsubstituted alkoxy group include a methoxy group, an ethoxy group, a propoxy group, an isopropyloxy group, a butoxy group, and a pentoxy group. At least one hydrogen atom of the alkoxy group may be substituted with a substituent such as those described above in conjunction with the alkyl group.

The unsubstituted $C_5$-$C_{60}$ aryl group indicates a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted as described above with reference to the unsubstituted $C_1$-$C_{60}$ alkyl group.

Examples of the substituted or unsubstituted $C_5$-$C_{60}$ aryl group include, but are not limited to, a phenyl group, a $C_1$-$C_{10}$ alkylphenyl group (for example, ethylphenyl group), a halophenyl group (for example, o-, m-, and p-fluorophenyl group, dichlorophenyl group), a cyanophenyl group, dicyanophenyl group, a trifluoromethoxyphenyl group, a biphenyl group, a halobiphenyl group, a cyanobiphenyl group, a $C_1$-$C_{10}$ alkyl biphenyl group, a $C_1$-$C_{10}$-alkoxybiphenyl group, a o-, m-, and p-tolyl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (for example, fluoronaphthyl group), a $C_1$-$C_{10}$ alkylnaphthyl group (for example, methylnaphthyl group), a $C_1$-$C_{10}$ alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinonyl group, a methylanthryl group, a phenanthryl group, a triphenylene group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptaenyl group, a pyranthrenyl group, and an ovalenyl group.

The unsubstituted $C_3$-$C_{60}$ heteroaryl group includes one, two or three hetero atoms selected from N, O, P and S. At least two rings may be fused to each other or linked to each other by a single bond. Examples of the unsubstituted $C_3$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. In addition, at least one hydrogen atom in the heteroaryl group may be substituted with a substituent described above in conjunction with the unsubstituted $C_1$-$C_{60}$ alkyl group.

The unsubstituted $C_5$-$C_{60}$ aryloxy group is a group represented by $-OA_1$ wherein $A_1$ may be a $C_5$-$C_{50}$ aryl group. An example of the aryloxy group is a phenoxy group. At least one hydrogen atom in the aryloxy group may be substituted with a substituent described above in conjunction with the unsubstituted $C_1$-$C_{50}$ alkyl group.

The unsubstituted $C_5$-$C_{60}$ arylthio group is a group represented by $-SA_1$ where $A_1$ may be a $C_5$-$C_{60}$ aryl group. Nonlimiting examples of the arylthio group include a benzenethiol group and a naphthylthio group. At least one hydrogen atom in the arylthio group may be substituted with a substituent described above in conjunction with the unsubstituted $C_1$-$C_{60}$ alkyl group.

The unsubstituted $C_6$-$C_{60}$ condensed polycyclic group refers to a substituent including at least two rings wherein at least one aromatic ring and/or at least one non-aromatic ring are fused to each other. The unsubstituted $C_6$-$C_{60}$ condensed polycyclic group may include some of the substituents described in conjunction with the aryl group or the heteroaryl group.

The following compound is an example of the condensed polycyclic group.

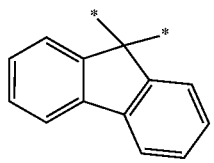 [SMILES: *C1(*)c2ccccc2-c2ccccc21]

X in the compound of Formula 1 tends to be perpendicular to moiety A (pyrene moiety) in Formula 1 (see below), interfering with lone pair electron of moiety B (arylamine moiety) forming a resonance structure in the moiety A.

Formula 1

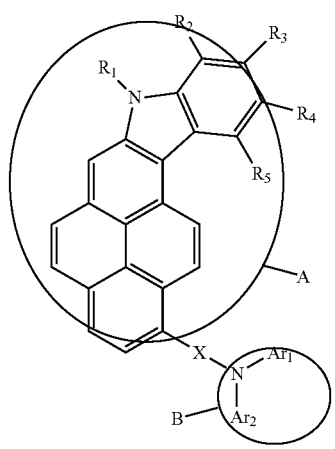

As a result, the compound of Formula 1 may emit high-color purity blue light. The blue light emitted from the compound of Formula 1 is distinct from common longer-wavelength bluish green light.

The compound of Formula 1 may have strong resistance to heat. Thus, when used in an organic light-emitting device, the compound of Formula 1 may improve efficiency and lifespan characteristics of the organic light emitting device.

Examples of the heterocyclic compound represented by Formula 1 may include Compounds 1 through 75 represented by the following formulae. However, the heterocyclic compounds represented by Formula 1 are not limited thereto.

1

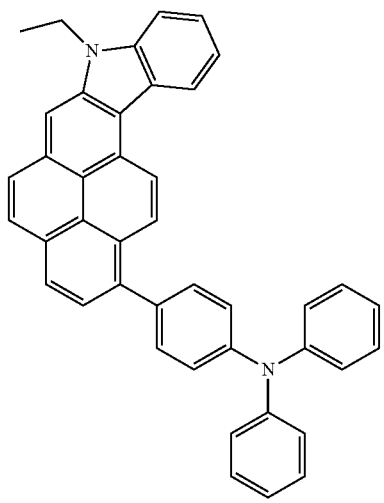

2

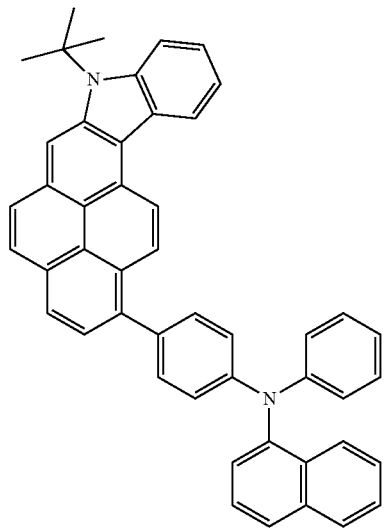

3

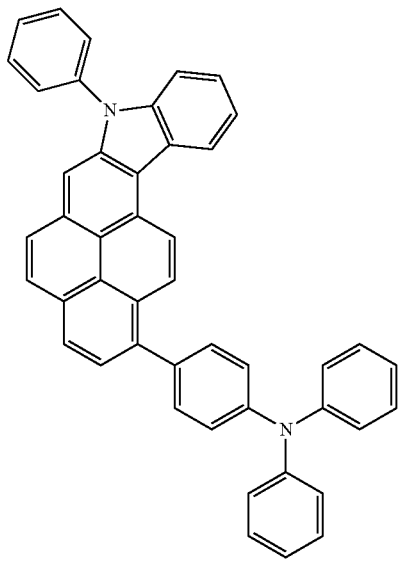

4

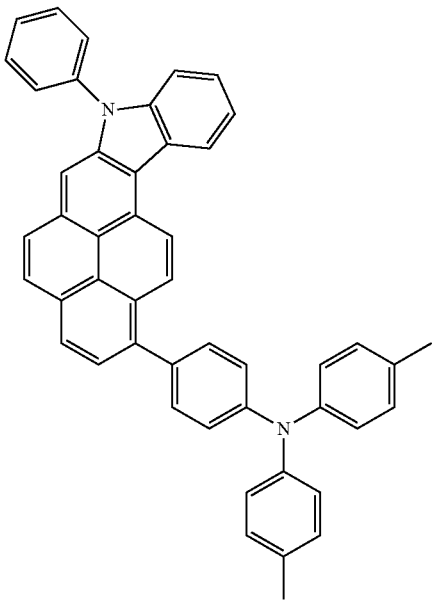

5
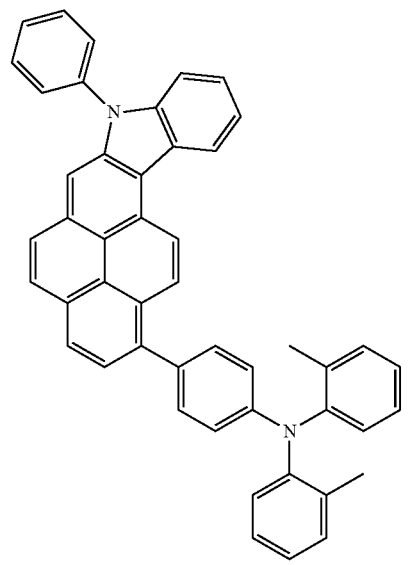
6
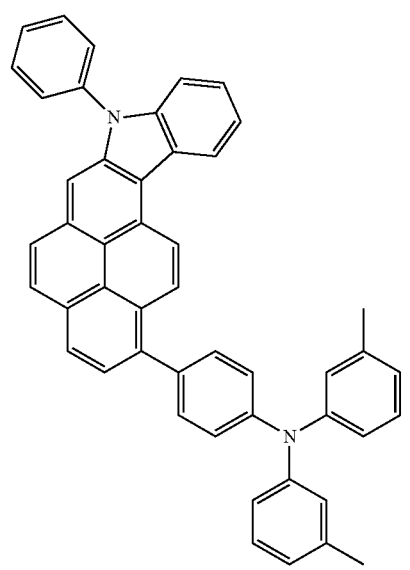
7
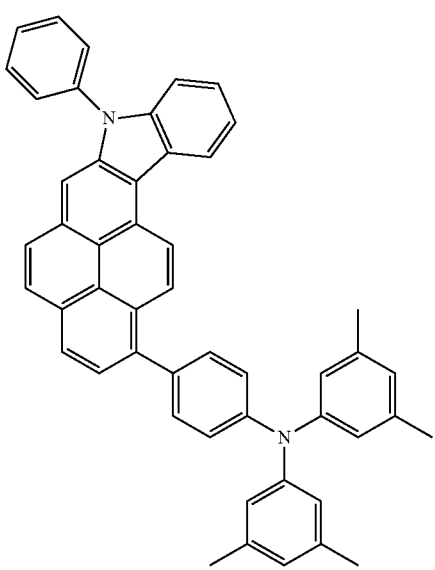
8
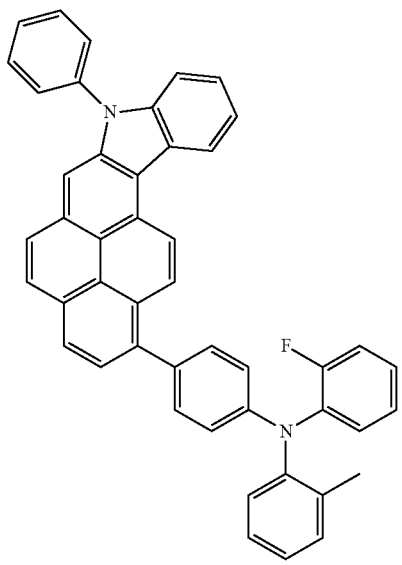
9
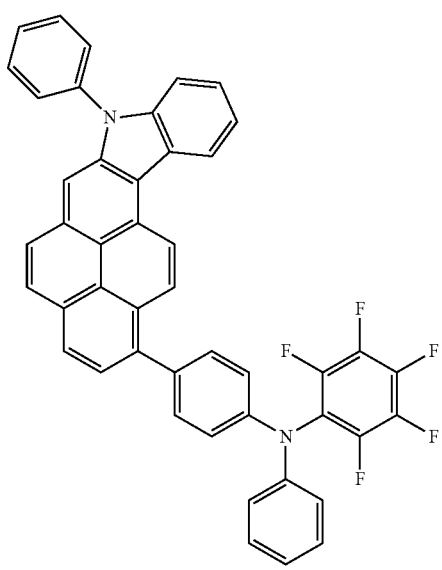
10
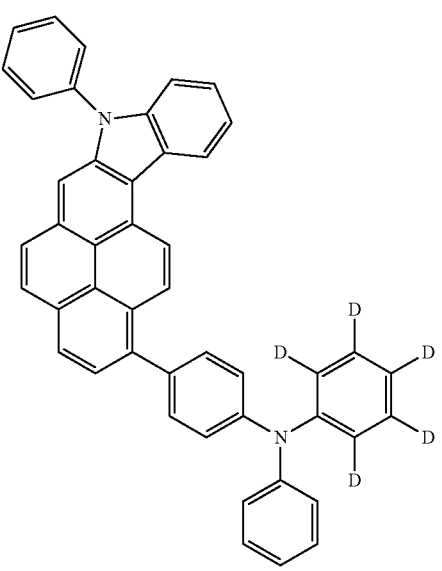

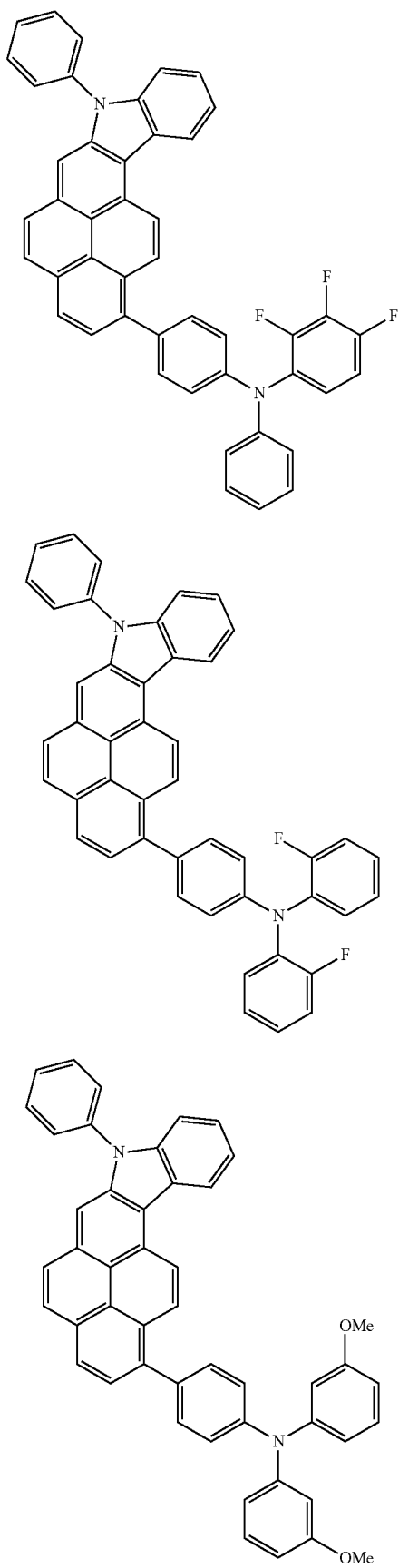
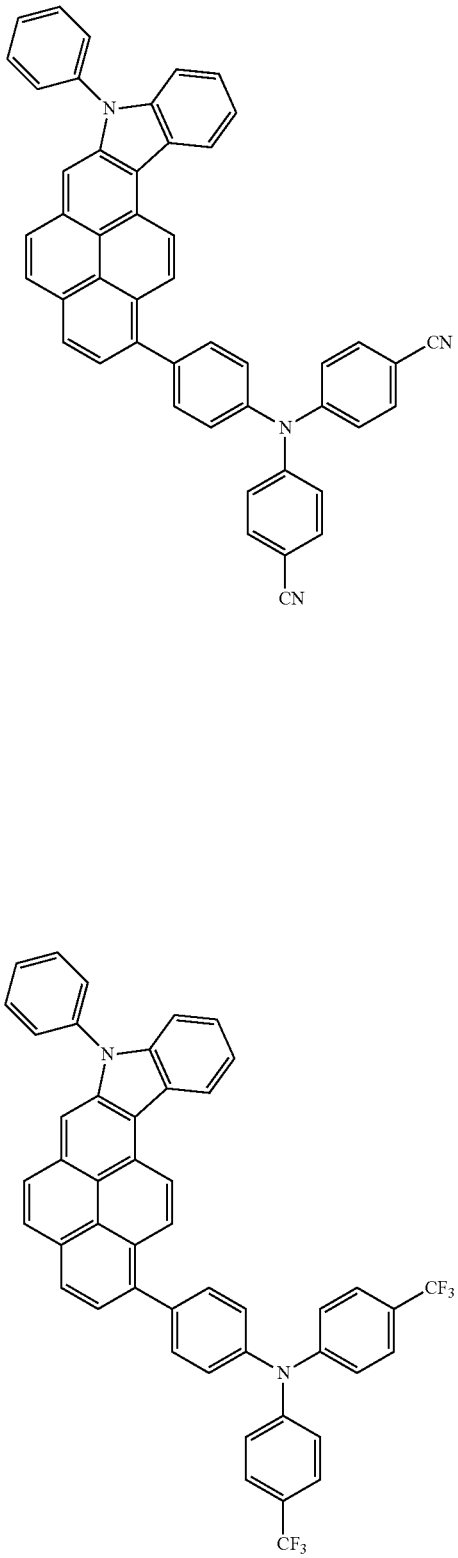

16
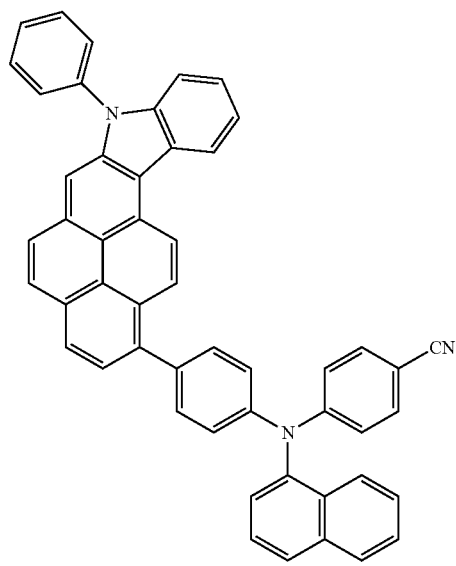
18
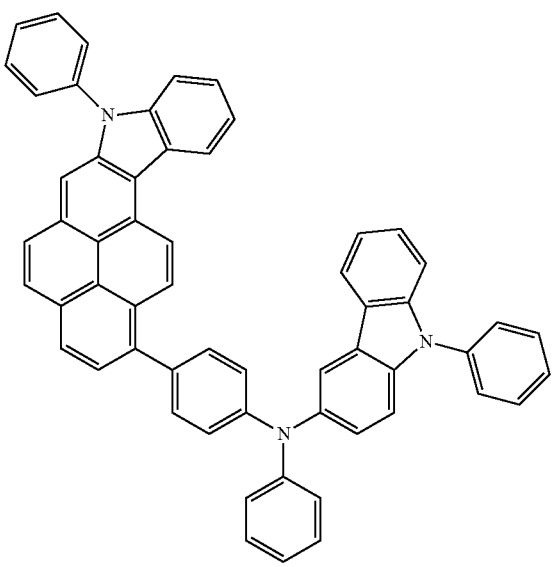
17
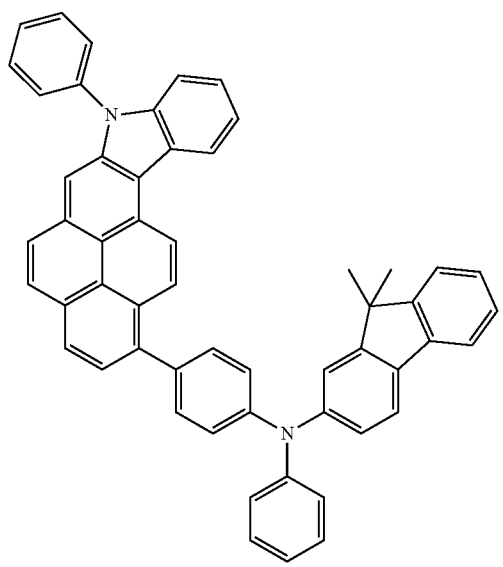
19
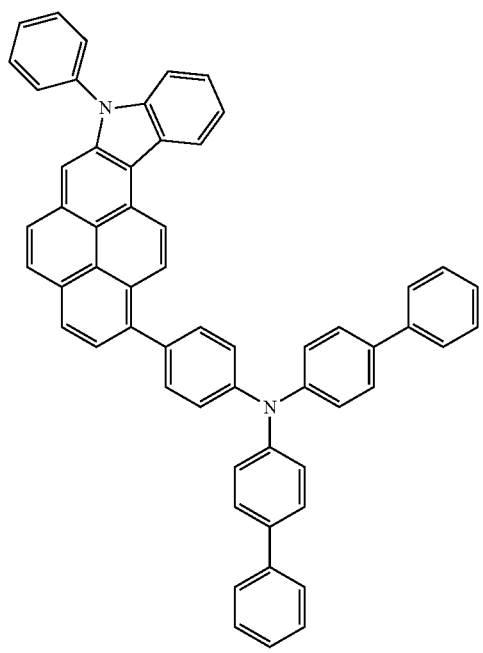

20
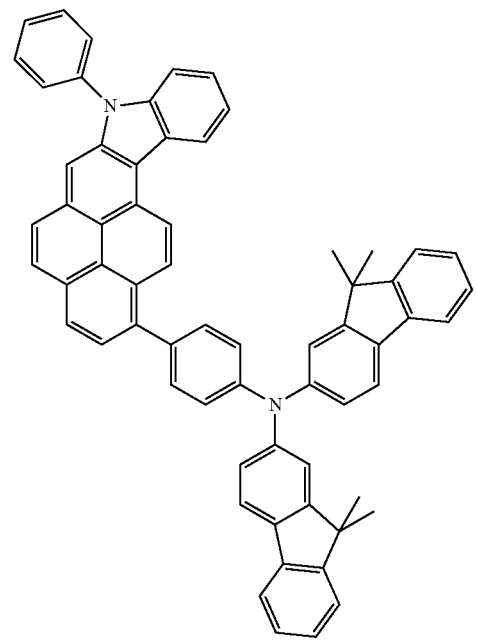
21
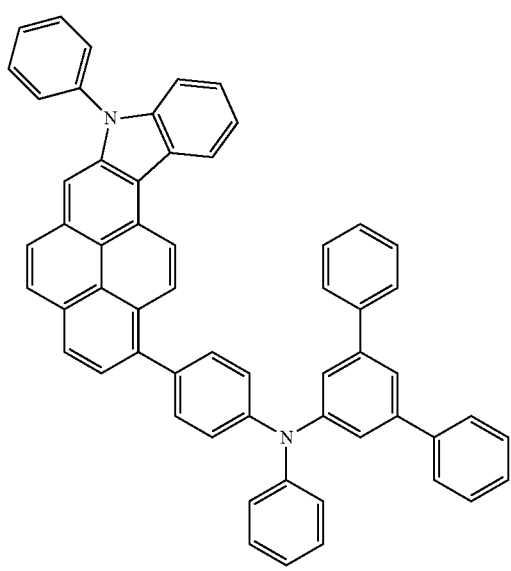
22
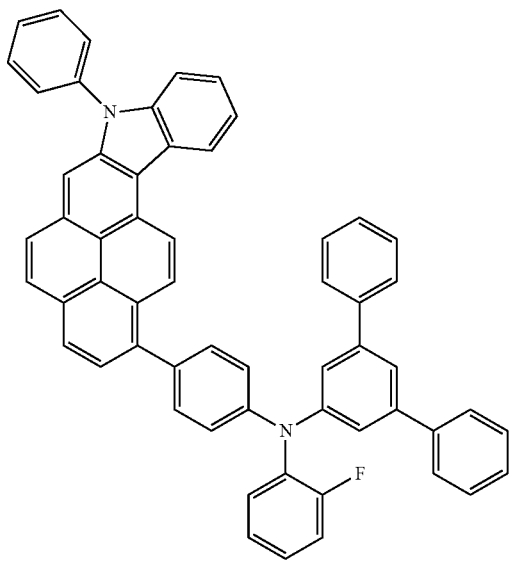
23
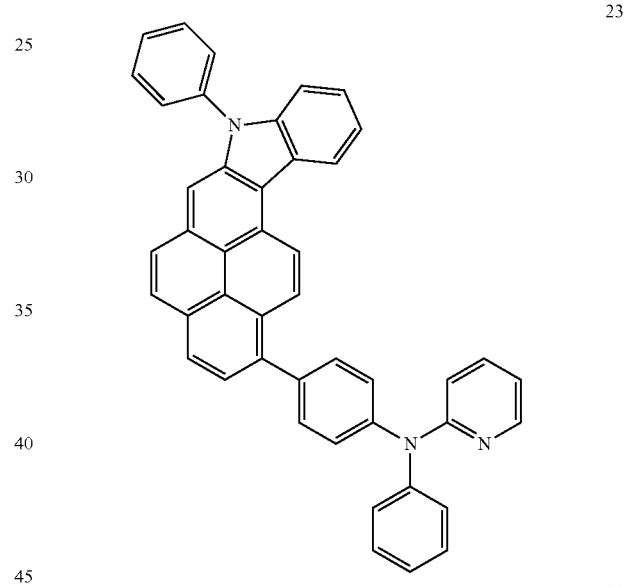
24
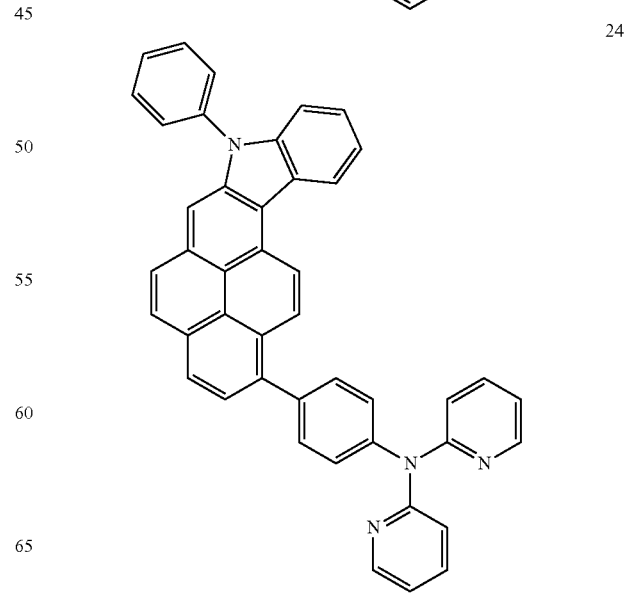

25
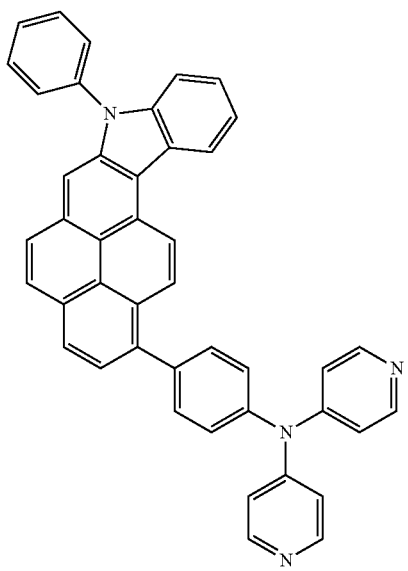
26
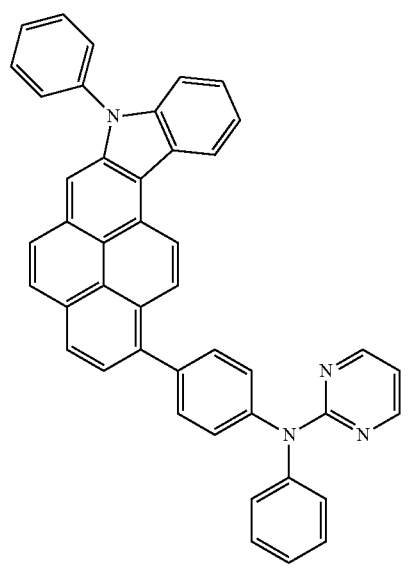
27
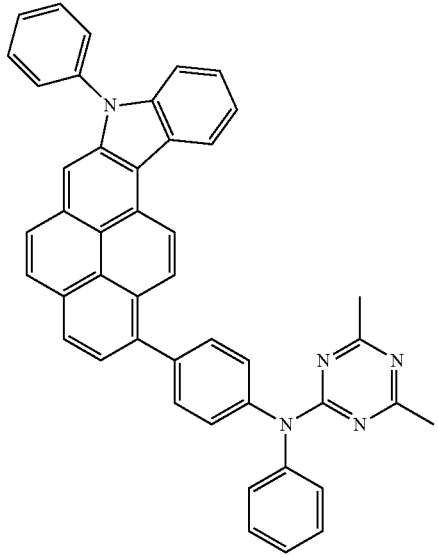
28
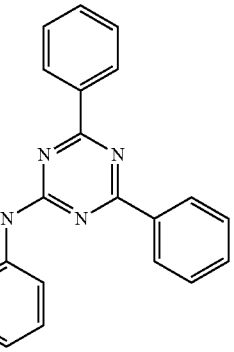
29
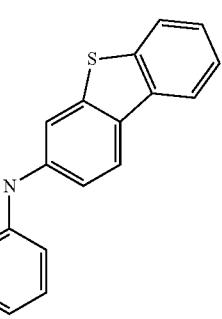

30
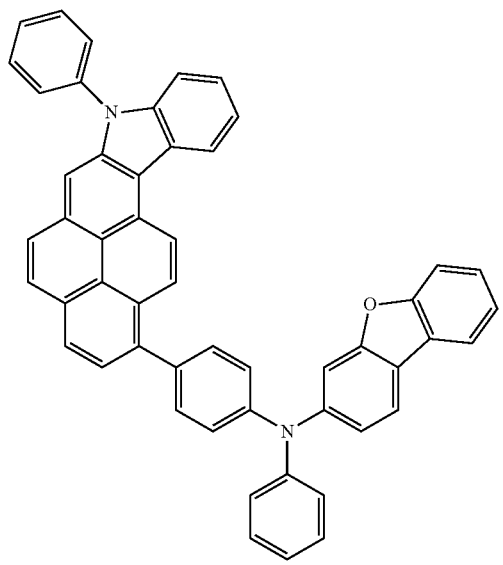
31
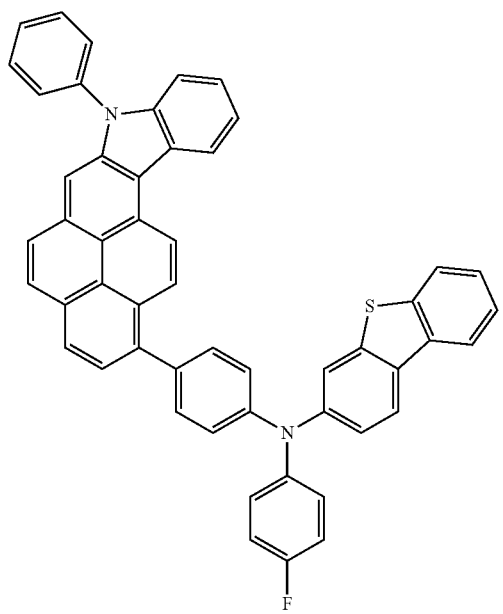
32
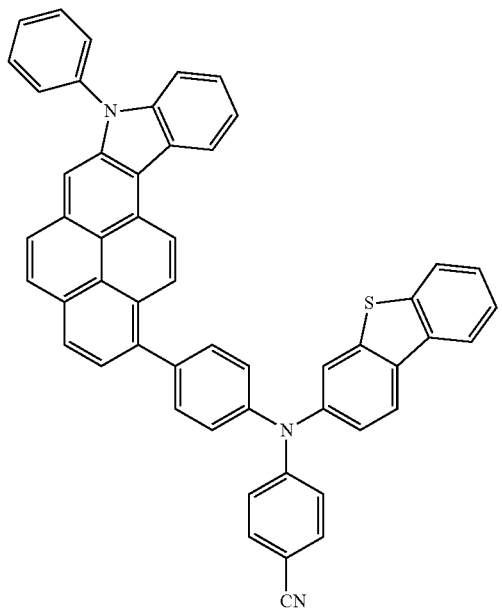
33
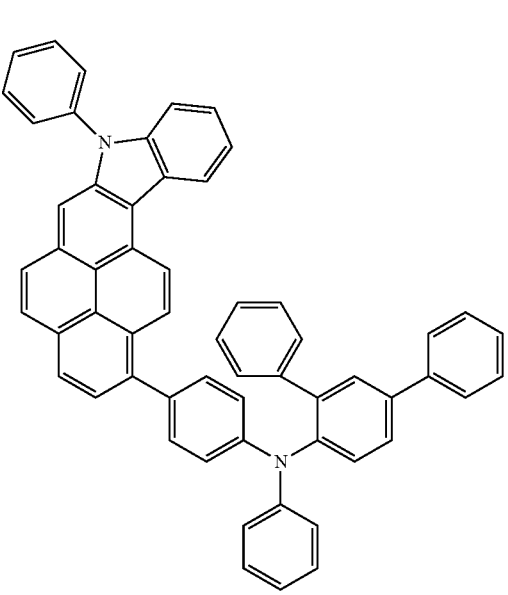

34
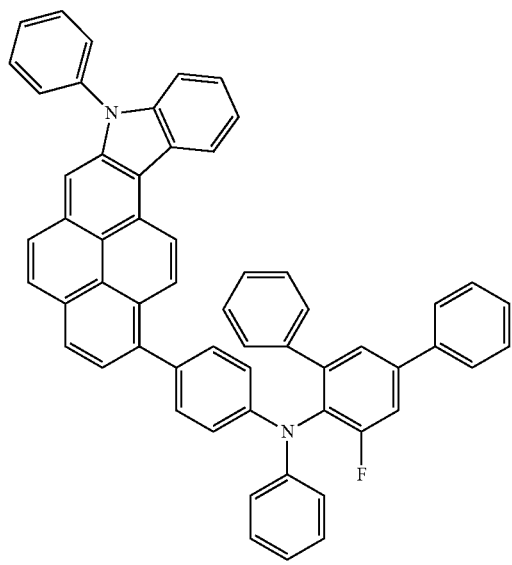
35
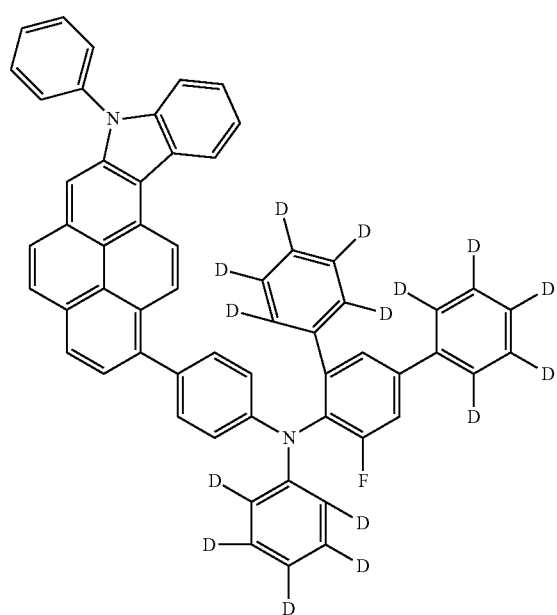
36
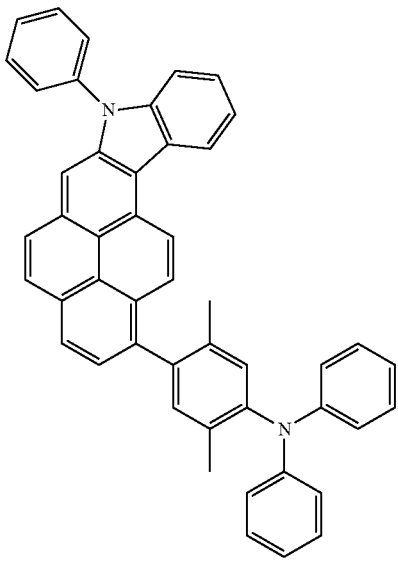
37
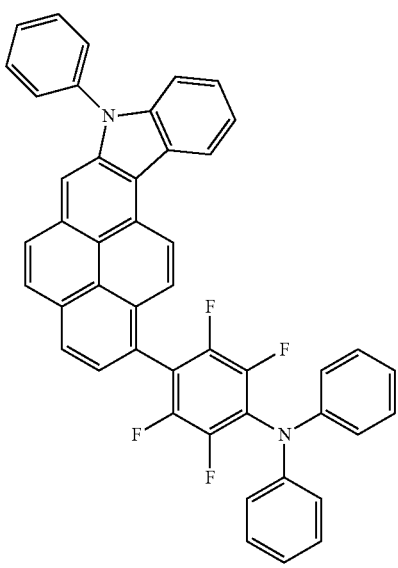
38
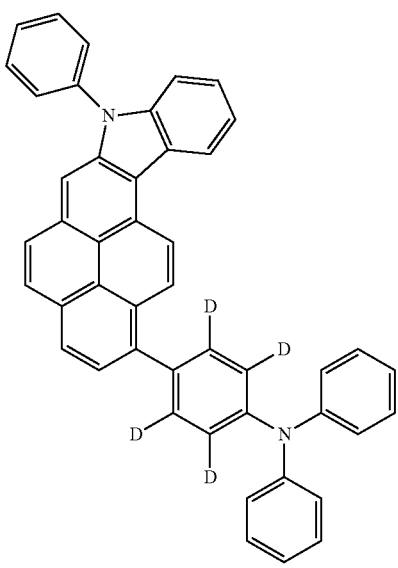

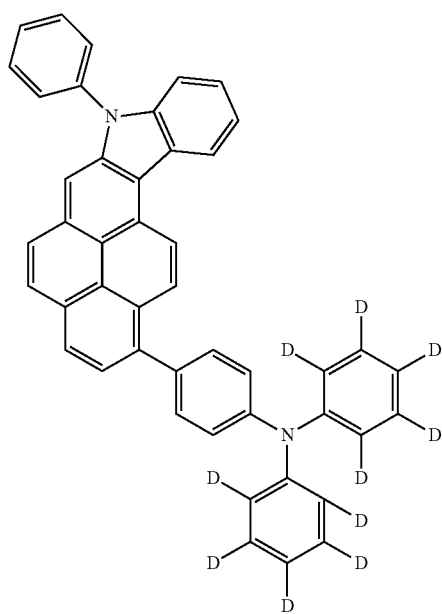
39
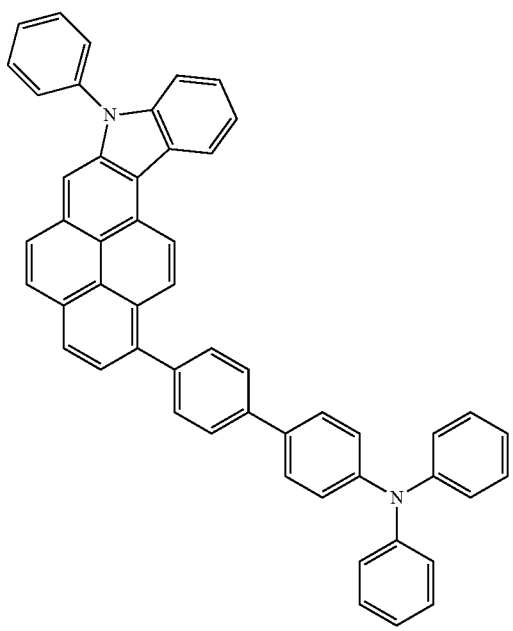
41
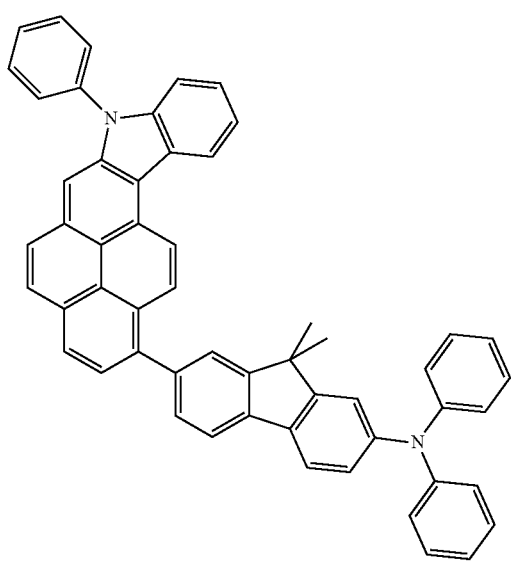
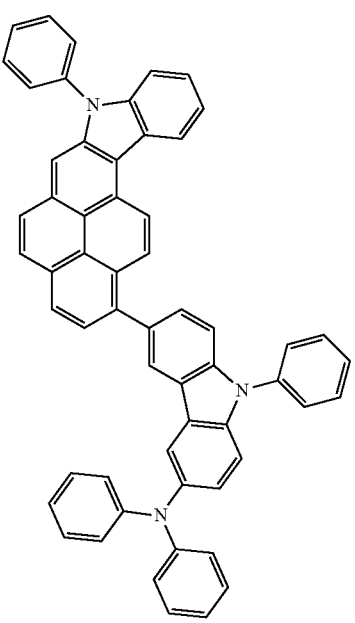
42

43
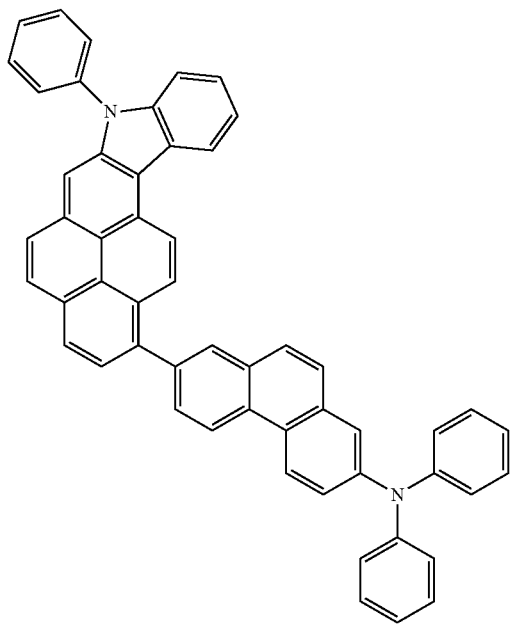
45
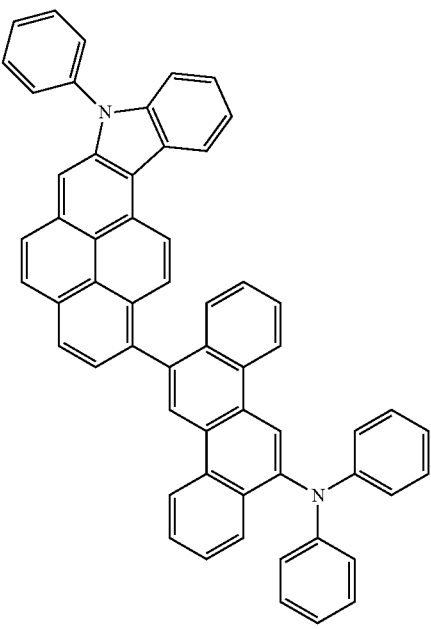
44
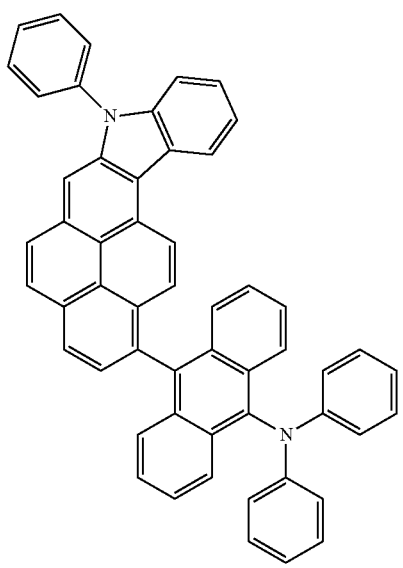
46

47
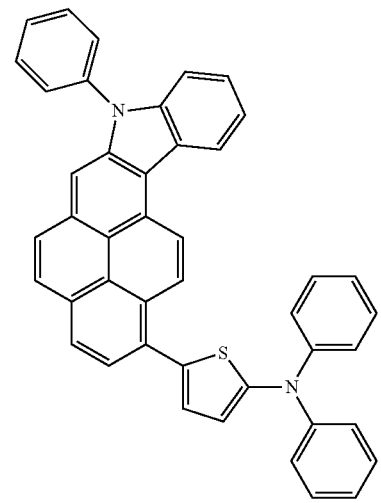
48
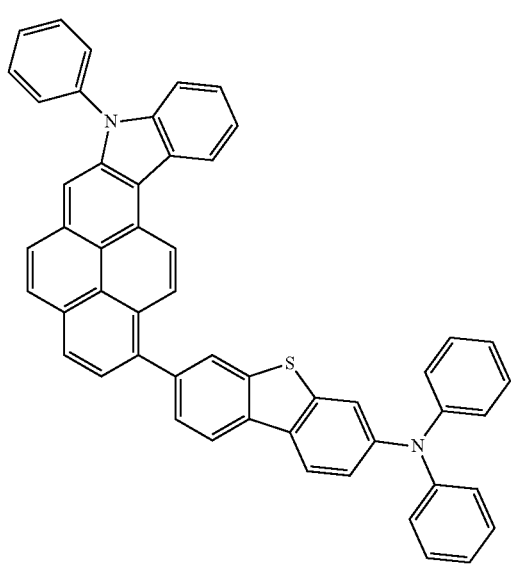
50
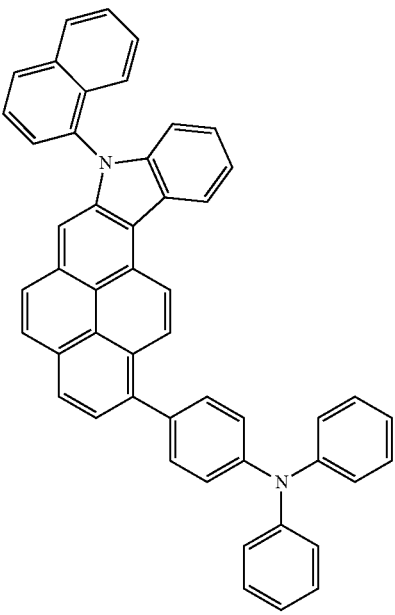
51
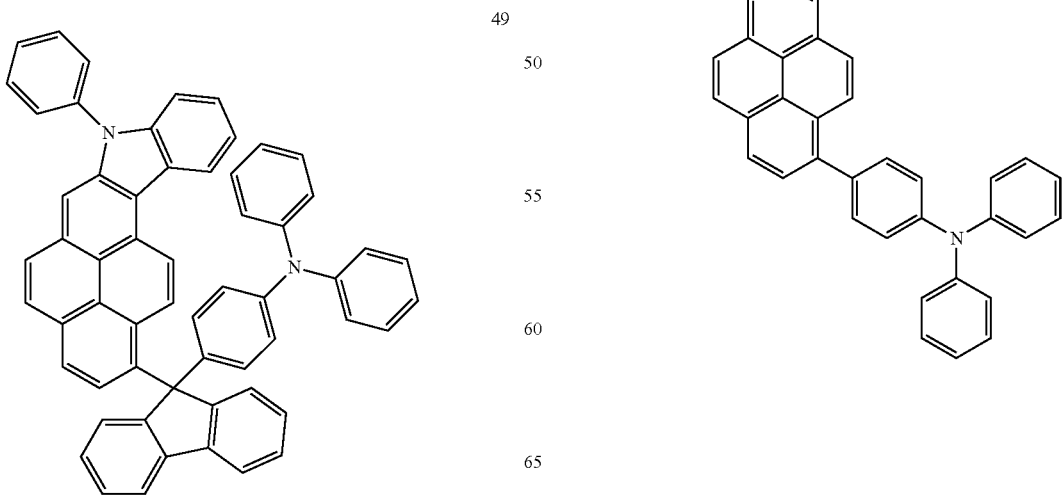

52
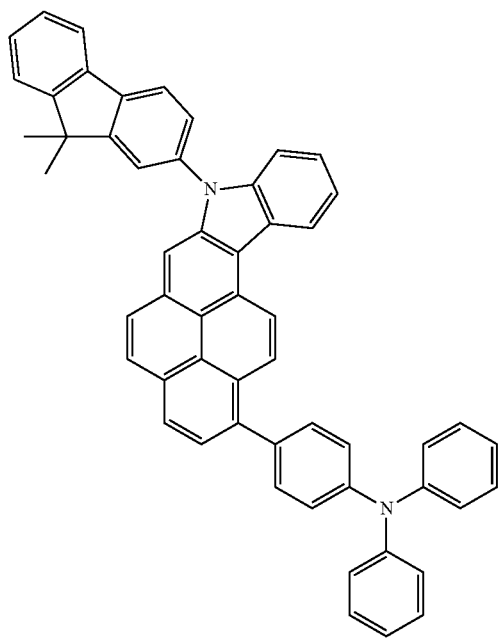
53
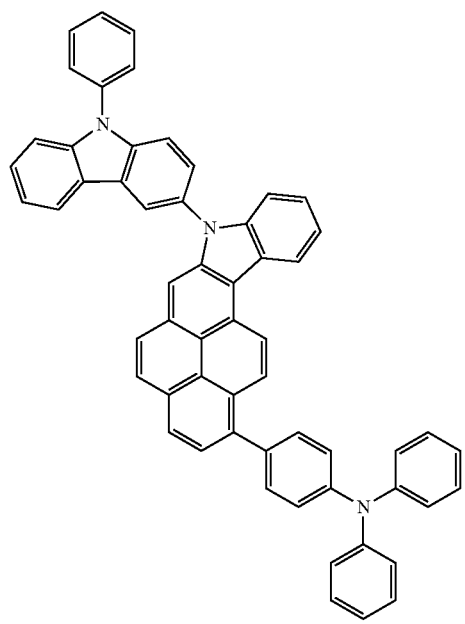
54
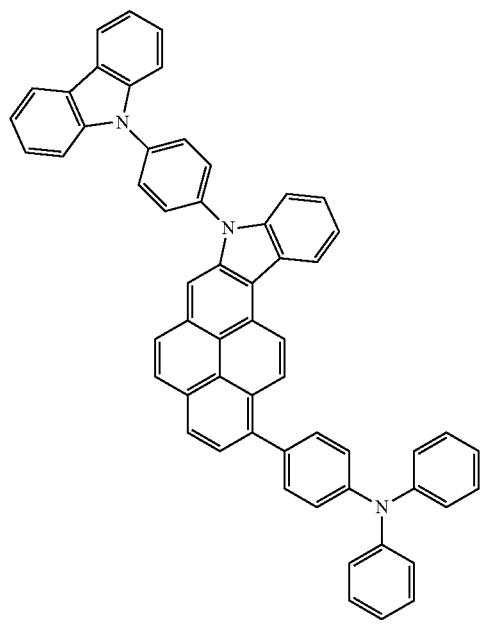
55
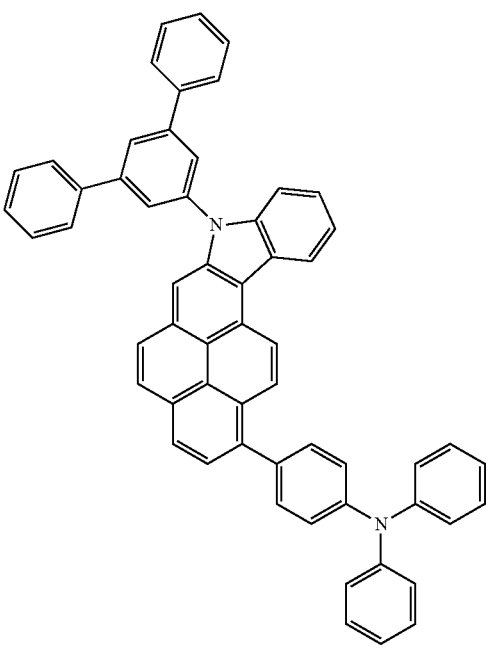

56
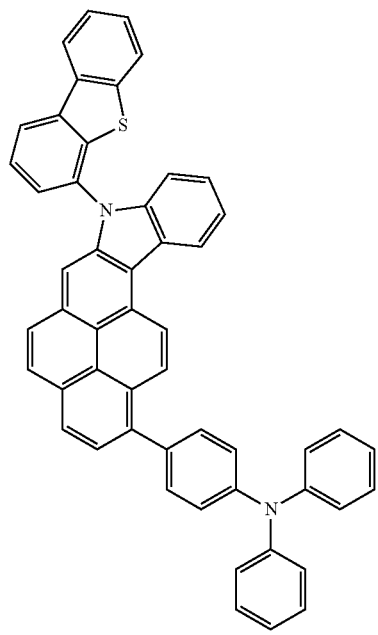
57
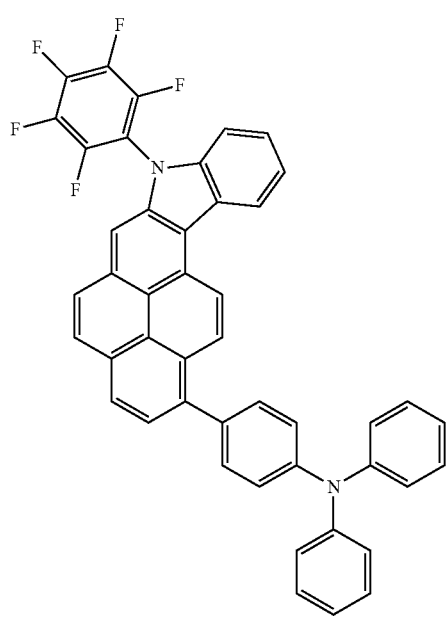
58
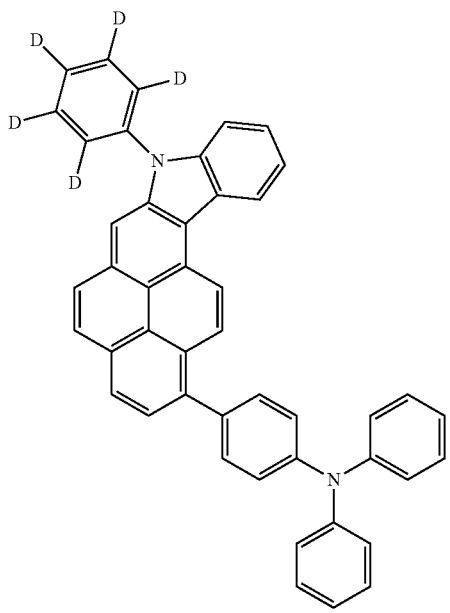
59
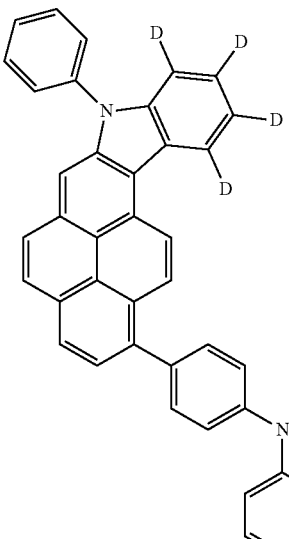

60
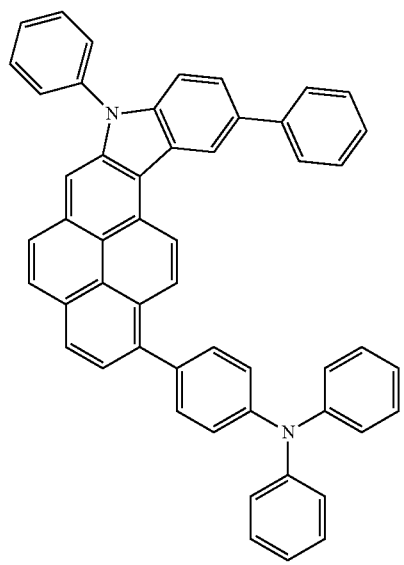
62
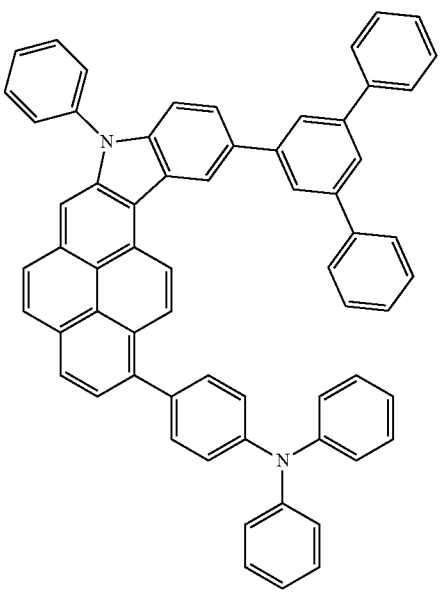
61
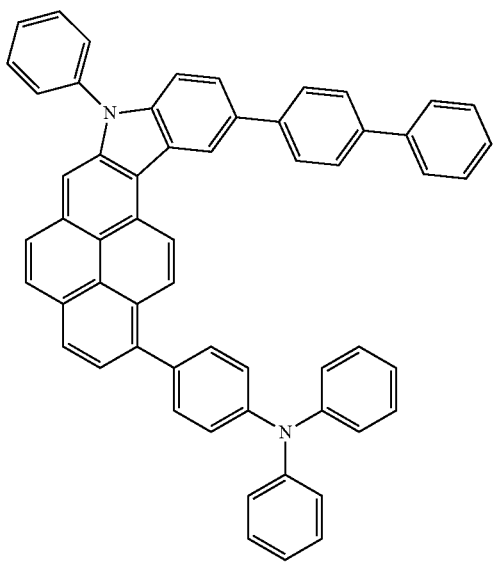
63
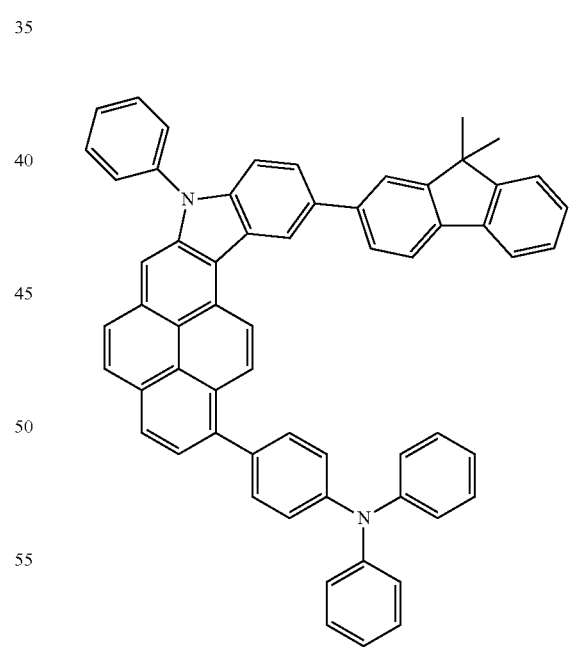

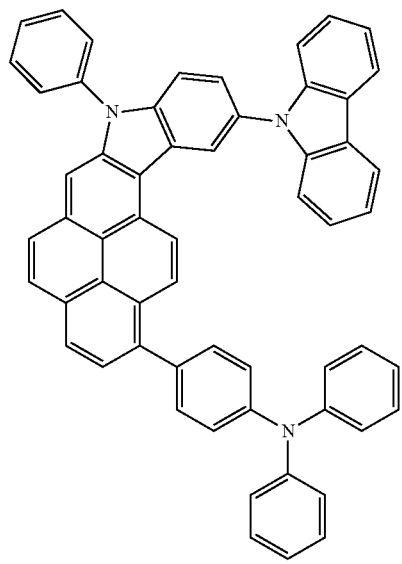
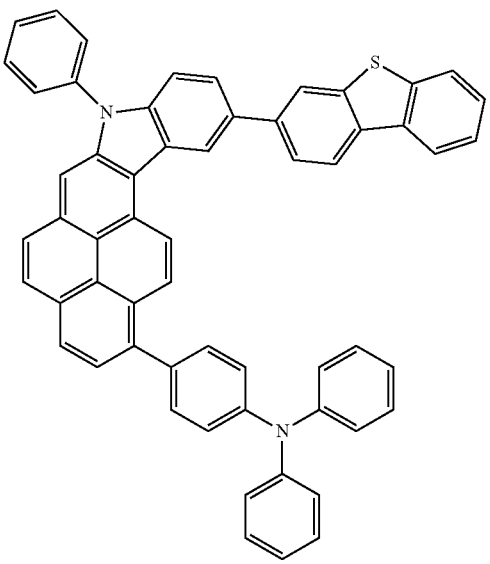

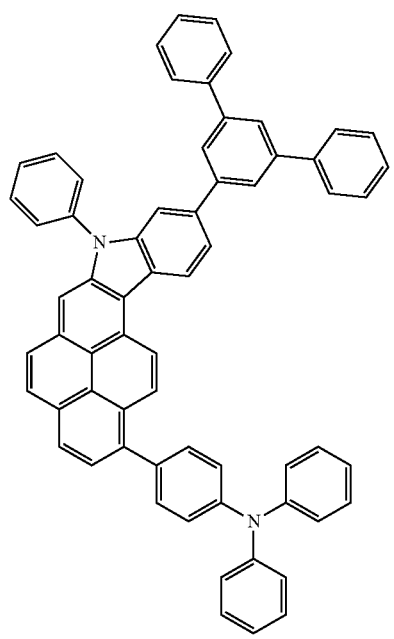
69
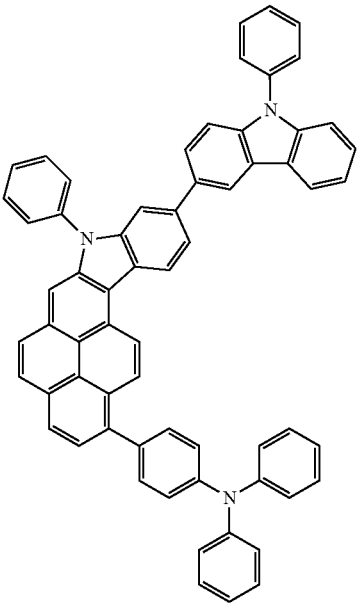
71
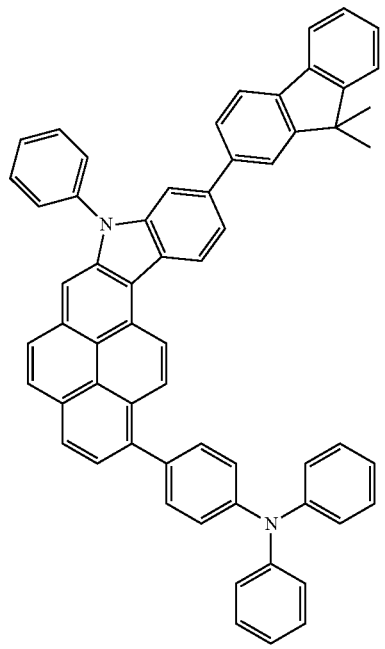
70
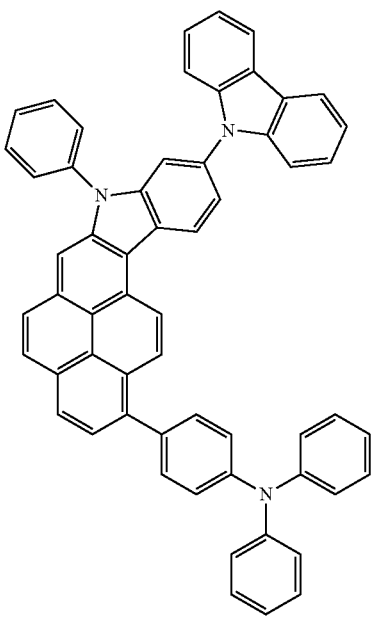
72

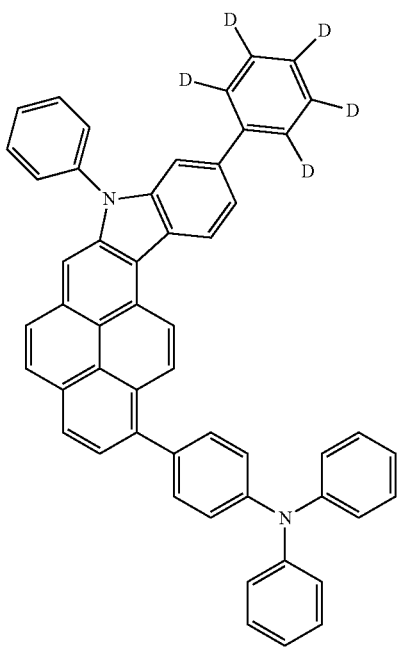

73

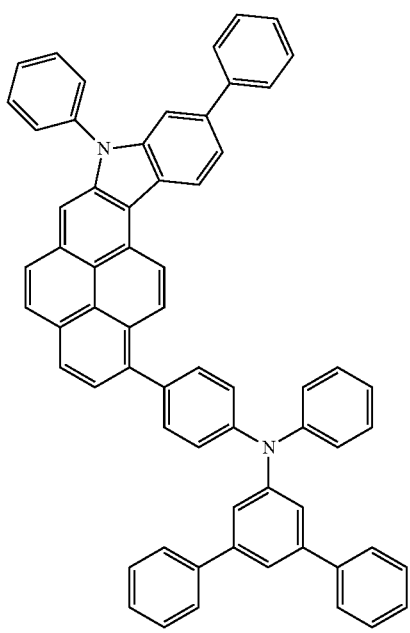

74

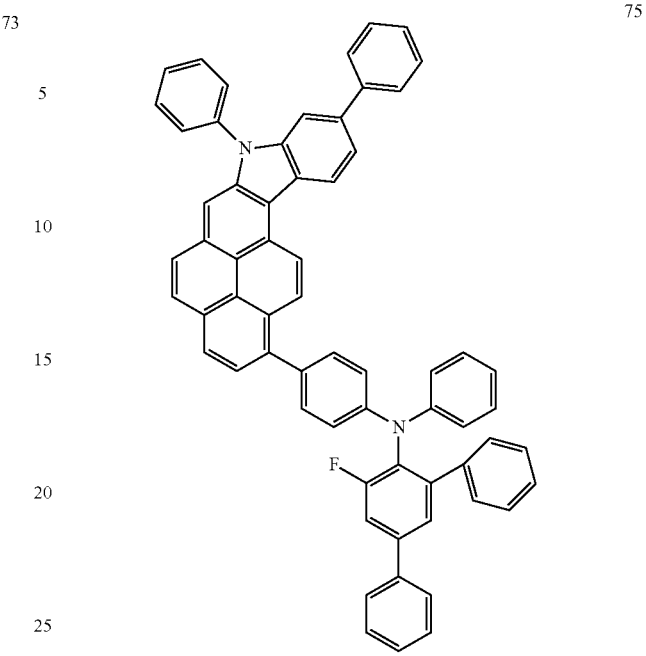

75

According to an embodiment, an organic light-emitting device includes a first electrode, a second electrode, and an organic layer between the first electrode and the second electrode, wherein the organic layer may include a first layer including the heterocyclic compound of Formula 1 described above.

The first layer including the heterocyclic compound of Formula 1 may include a hole injection layer, a hole transport layer, or a functional layer having both hole injection and hole transport capabilities.

The first layer including the heterocyclic compound of Formula 1 may include an electron injection layer, an electron transport layer, or a functional layer having both electron injection and electron transport capabilities.

When the first layer including the heterocyclic compound of Formula 1 is an emission layer, the heterocyclic compound of Formula 1 may be used as a host or a dopant for a fluorescent or phosphorescent device.

In some embodiments if the first layer of the organic light-emitting device is an emission layer, the emission layer may further include a known anthracene, arylamine or styryl compound.

In addition, at least one hydrogen atom in the anthracene, arylamine or styryl compound may be substituted with a substituent described above in conjunction with the unsubstituted $C_1$-$C_{60}$ alkyl group.

The arylamine is a $C_5$-$C_{60}$ arylamine group including an amino group with a $C_5$-$C_{60}$ aryl or $C_3$-$C_{60}$ heteroaryl substituent.

In some embodiments if the first layer of the organic light-emitting device is an emission layer, a red emission layer, a green emission layer, a blue emission layer or a white emission layer of the emission layer may include a widely-known phosphorescent compound.

In some embodiments the first layer of the organic light-emitting device may include a blue emission layer. When the first layer includes a blue emission layer, the heterocyclic compound of Formula 1 may be used as a blue dopant. In some embodiments, the organic layer of the organic light-emitting device may further include, but is not limited to, a hole injection layer, a hole transport layer, a functional layer having both hole injection and transport functions, an emission layer, a hole blocking layer, an electron transport layer, an electron injection layer, of a combination of at least two of these layers. At least one of the hole injection layer, the hole transport layer, and the functional layer having both hole injection and transport functions, may further include, in addition to the heterocylic compound of Formula 1 and widely-known hole injection and transport materials, a charge-generating material for improving conductivity of the layer.

The charge-generating material may include, for example, a p-dopant. Nonlimiting examples of the p-dopant include quinine derivatives, including tetracyanoquinondimethane (TCNQ) and 2,3,5,6-tetrafluoro-tetracyano-1,4-benzoquinonedmethane (F4TCNQ); metal oxides, including tungsten oxide and molybdenum oxide; and cyano group-containing compounds, including a compound represented by Formula 100 below.

Formula 100

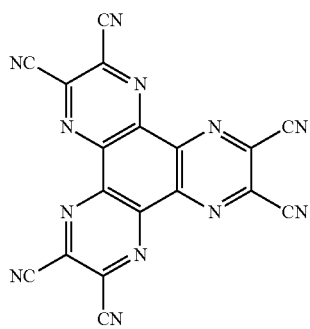

In some embodiments, when the hole injection layer, the hole transport layer, or the functional layer having both hole injection and transport functions further includes the charge-generating material, the charge-generating material may be uniformly or nonuniformly distributed in the layer.

In one embodiment, the electron transport layer of the organic light-emitting device may include an electron transporting organic compound and a metal-containing material. Nonlimiting examples of the electron transporting organic compound include ADN (9,10-di(naphthalene-2-yl)anthracene); and anthracene-based compounds, including a compound of Formula 101 and a compound of Formula 102 below.

Formula 101

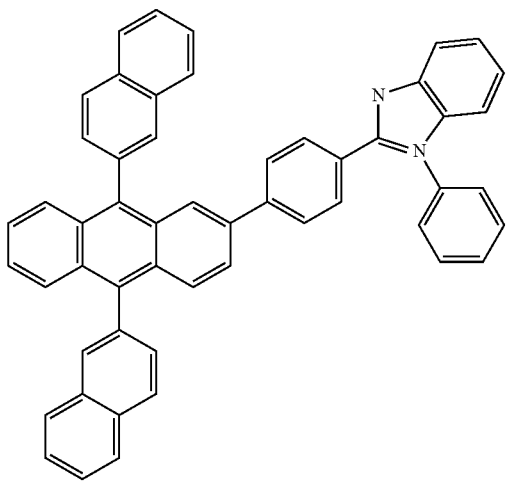

Formula 102

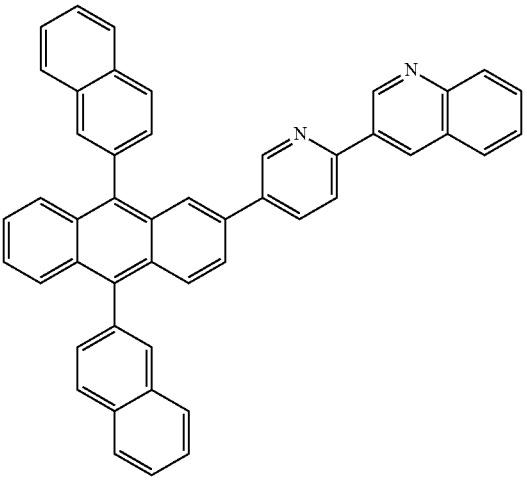

The metal-containing material may include a Li complex. Nonlimiting examples of the Li complex include lithium quinolate (LiQ) and a compound of Formula 103 below.

Formula 103

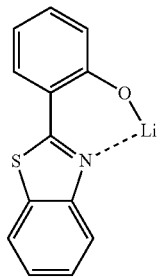

The first electrode may be an anode, and the second electrode may be a cathode, but the reverse is also possible.

In some embodiments, the organic light-emitting device may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure. In some other embodiments, the organic light-emitting device may have a first electrode/functional layer having both hole injection and hole transport capabilities/emission layer/electron transport layer/second electrode structure, or a first electrode/functional layer having both hole injection and hole transport capabilities/emission layer/electron transport layer/electron injection layer/second electrode structure. Alternatively, the organic light-emitting device may have a first electrode/hole transport layer/emission layer/functional layer having both electron injection and electron transport capabilities/second electrode structure, a first electrode/hole injection layer/emission layer/functional layer having both electron injection and electron transport capabilities/second electrode structure, or a first electrode/hole injection layer/hole transport layer/emission layer/functional layer having both electron injection and electron transport capabilities/second electrode structure.

In some embodiments the organic light-emitting device may be either a top-emission organic light-emitting device or a bottom-emission organic light emitting device.

Hereinafter, a method of manufacturing an organic light-emitting device according to an embodiment of the present invention will be described with reference to FIG. 1. FIG. 1 illustrates the structure of an organic light-emitting device according to an embodiment of the present invention. Referring to FIG. 1, the organic light-emitting device according to the present embodiment includes a substrate (not shown), a first electrode (anode), a hole injection layer (HIL), a hole transport layer (HTL), an emission layer (EML), an electron transport layer (ETL), an electron injection layer (EIL), and a second electrode (cathode).

First, the first electrode is formed on the substrate by using a deposition or sputtering method. The first electrode may be formed of a first electrode material having a high work function. The first electrode may constitute an anode or a cathode. The substrate may be a substrate conventionally used in organic light-emitting devices, and may include, for example, a glass substrate or a transparent plastic substrate with excellent mechanical strength, thermal stability, transparency, surface smoothness, ease of handling, And water resistance. Examples of the first electrode material include materials, such as indium tin oxide (ITO), indium zinc oxide (17.0), tin oxide (SnO2), zinc oxide (ZnO), aluminum (Al), silver (Ag), and magnesium (Mg), which have excellent conductivity. The first electrode may be formed as a transparent or reflective electrode.

An organic layer(s) is formed on the first electrode. The term "organic layer" used herein indicates any layer interposed between the first electrode and the second electrode. The organic layer may not be formed of pure organic materials, and may also include a metal complex.

The organic layer may include a first layer including the heterocyclic compound of Formula 1. The organic layer may further include at least one of a HIL, a EML, a hole blocking layer (HBL), an ETL, and an EIL. The first layer may include an emission layer.

The HIL may be formed on the first electrode by using any of a variety of methods, and in some embodiments, by using vacuum deposition, spin coating, casting, Langmuir-Blodgett (LB) deposition, or the like.

When the HIL is formed using vacuum deposition, the deposition conditions may vary according to the material that is used to form the HIL, and the structure and thermal characteristics of the HIL. For example, the deposition conditions may include a deposition temperature of about 100 to about 500° C., a vacuum pressure of about $10^{-8}$ to about $10^{-3}$ torr, and a deposition rate of about 0.01 to about 100 Å/sec.

When the HIL is formed using spin coating, coating conditions may vary according to the material used to form the HIL, and the structure and thermal properties of the HIL. For example, the coating conditions may include a coating speed of about 2000 rpm to about 5000 rpm, and a thermal treatment temperature of about 80° C. to about 200° C. at which the solvent remaining after coating may be removed.

The HIL may be formed of the heterocyclic compound of Formula 1 or any material that is commonly used to form a HIL. Nonlimiting examples of the material that can be used to form the HIL include a phthalocyanine compound such as copperphthalocyanine, 4,4',4"-tris(3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS).

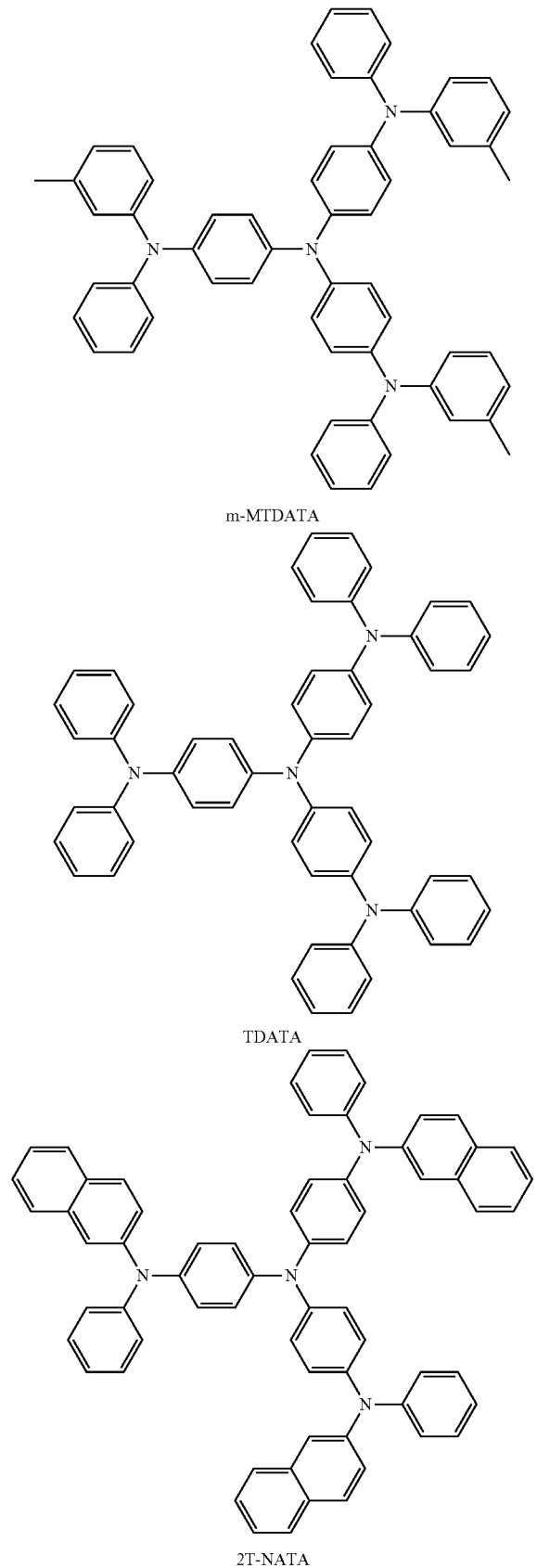

m-MTDATA

TDATA

2T-NATA

The HIL may have a thickness of about 100 Å to about 10000 Å, and in some embodiments, a thickness of about 100 Å to about 1000 Å. When the thickness of the HIL is within these ranges, the HIL may have good hole injection characteristics without an increase in driving voltage.

Next, the HTL may be formed on the HIL by using any of a variety of methods, and in some embodiments, by using vacuum deposition, spin coating, casting, LB deposition, or the like. When the HTL, is formed using vacuum deposition or spin coating, the deposition or coating conditions may be similar to those applied to form the HIL, though the deposition or coating conditions may vary according to the material that is used to form the HTL.

The HTL may be formed of the heterocyclic compound of Formula 1 or any known HTL material. Nonlimiting examples of such HTL materials include carbazole derivatives such as N-phenylcarbazole or polyvinylcarbazole, and amine derivatives having an aromatic condensed ring, such as NPB, N,N'-bis(3-methylphenyl)-N,N'-diphenyl-[1,1-biphenyl]-4,4'-diamine (TPD).

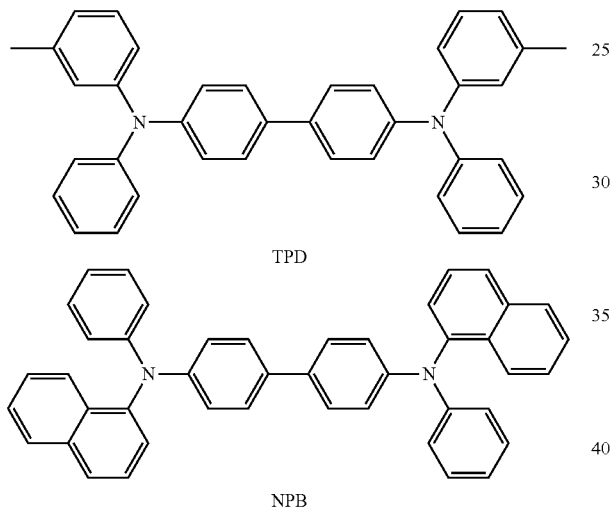

The HTL may have a thickness of about 50 Å to about 1000 Å, and in some embodiments, a thickness of about 100 Å to about 600 Å. When the thickness of the HTL is within these ranges, the HTL may have good hole transport characteristics without a substantial increase in driving voltage.

Next, the EML may be formed on the HTL by using any of a variety of methods, and in some embodiments, by using vacuum deposition, spin coating, casting, LB deposition, or the like. When the EML is formed using vacuum deposition or spin coating, the deposition or coating conditions may be similar to those applied to form the HIL, though the deposition or coating conditions may vary according to the material that is used to form the EML.

The EML may include the heterocyclic compound of Formula 1 described above. For example, the heterocyclic compound of Formula 1 may be used as a host or a dopant. The EML may be formed using a variety of well-known light-emitting materials, in addition to the heterocyclic compound of Formula 1. Alternatively, the EML may also be formed using a well-known host and a dopant. Dopants that may be used to form the EML may include either a fluorescent dopant or a phosphorescent dopant, which are widely known in the art.

Examples of the host include Alq3, dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tort-butyl-9,10-di-2-naphthylanthracene (TBADN), E3, and distyrylarylene (DSA), bur are not limited thereto.

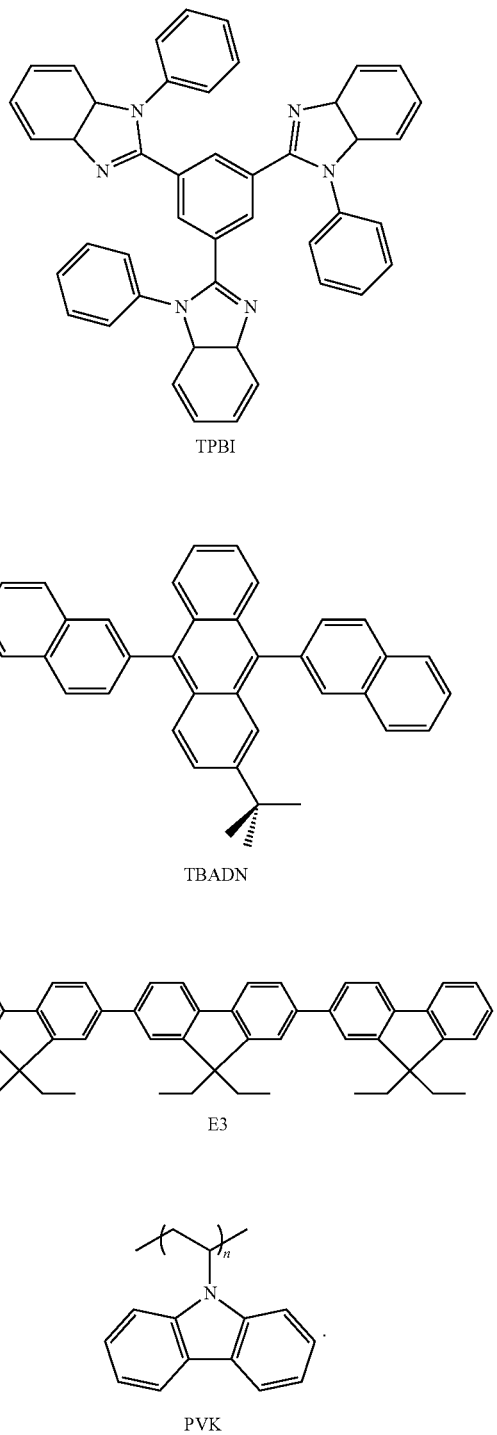

Nonlimiting examples of red dopants include platinum(II) octaethylporphyrin (PtOEP), Ir(piq)$_3$, Btp$_2$Ir(acac), and DCJTB.

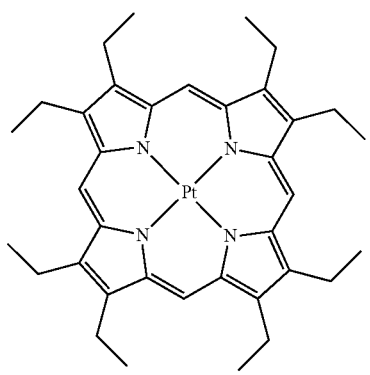

PtOEP

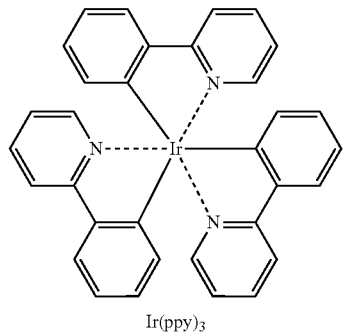

Ir(ppy)₃

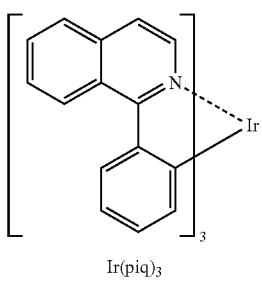

Ir(piq)₃

Ir(ppy)₂(acac)          Ir(mpyp)₃

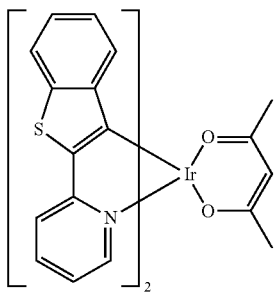

Btp₂Ir(acac)

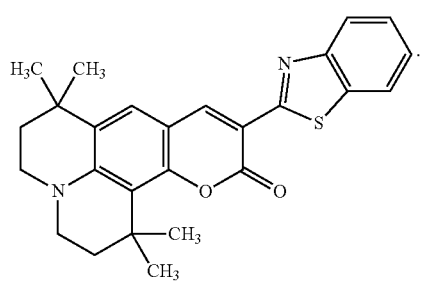

C545T

Nonlimiting examples of green dopants include Ir(ppy)₃ (where "ppy" denotes phenylpyridine), Ir(ppy)₂(acac), Ir(mpyp)₃, and C545T.

Nonlimiting examples of blue dopants include the heterocyclic compound of Formula 1, F₂Irpic, (F₂PPY)₂Ir(tmd), Ir(dfppz)₃, ter-fluorene, 4',4'-bis(4-diphenylaminostyryl)biphenyl (DPAVBi), and 2,5,8,11-tetra-t-butyl phenylene (TBP).

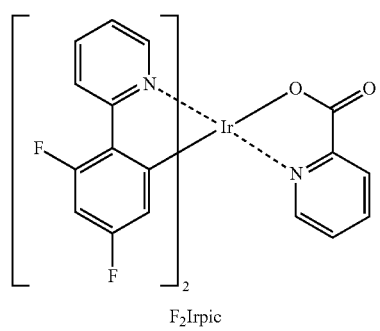

F₂Irpic

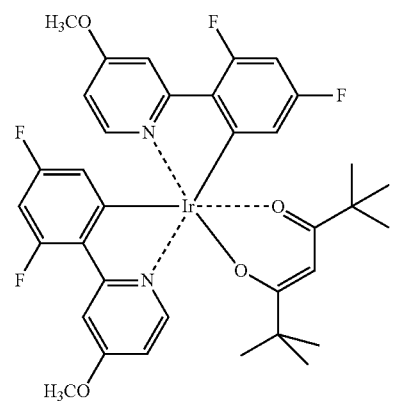

(F₂ppy)₂Ir(tmd)

-continued

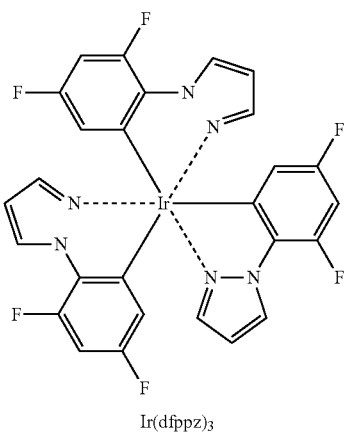
Ir(dfppz)₃

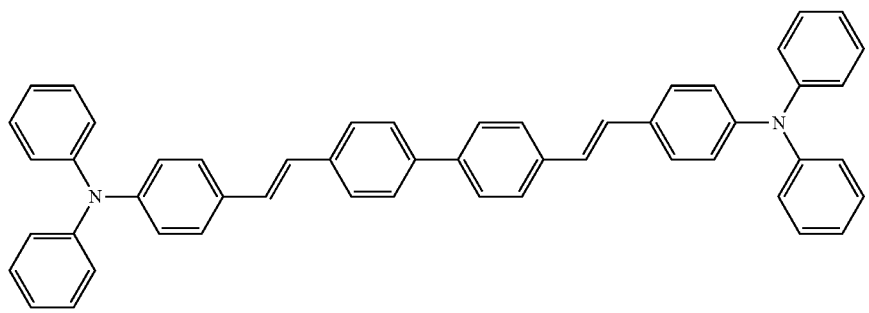
DPAVBi

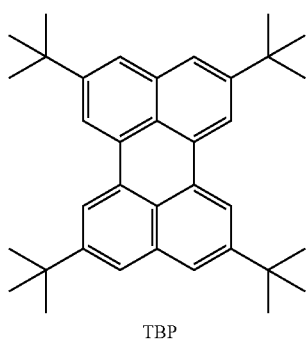
TBP

The amount of the dopant may be from about 0.1 to about 20 parts by weight, and in some embodiments, from about 0.5 to about 12 parts by weight, based on 100 parts by weight of the EML material, which is equivalent to the total weight of the host and the dopant. When the amount of the dopant is within these ranges, concentration quenching may be substantially prevented.

The EML may have a thickness of about 100 Å to about 1,000 Å, and in some embodiments, about 200 Å to about 600 Å. When the thickness of the EML is within these ranges, the EML may have good light-emitting characteristics without a substantial increase in driving voltage.

When the EML includes a phosphorescent dopant, a HBL (not shown in FIG. 1) may be formed on the EML in order to prevent diffusion of triplet excitons or holes into the ETL. In this case, the HBL may be formed of any material commonly used to form a HBL. Nonlimiting examples of such HBL materials include oxadiazole derivatives, triazole derivatives, phenanthroline derivatives, Balq, and BCP.

The HBL may have a thickness of about 50 Å to about 1,000 Å, and in some embodiments, about 100 Å to about 300 Å. When the thickness of the HBL is within these ranges, the HBL may have good hole blocking characteristics without a substantial increase in driving voltage.

Next, the ETL is formed on the EML (or HBL) by using any of a variety of methods, and in some embodiments, by using vacuum deposition, spin coating, casting, or the like. When the ETL is formed using vacuum deposition or spin coating, the deposition or coating conditions may be similar to those applied to form the HIL, though the deposition or coating conditions may vary according to the material that is used to form the ETL.

The ETL material may include the heterocyclic compound of Formula 1 scribed above. Alternatively, the ETL may be formed of any material that is widely known in the art. Nonlimiting examples of the En material include quinoline derivatives, such as tris(8-quinolinolate)aluminum (Alq3), TAZ, and BAlq.

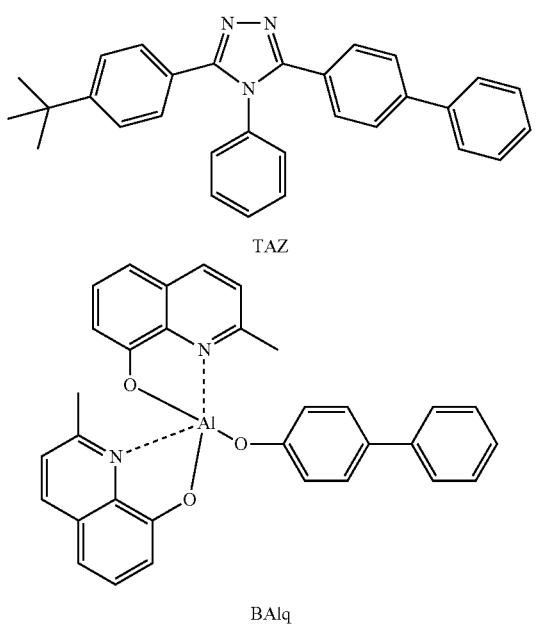

TAZ

BAlq

The ETL may have a thickness of about 100 Å to about 1,000 Å, and in some embodiments, about 100 Å to about 500 Å. When the thickness of the ETL is within these ranges, the ETL may have good electron transport characteristics without a substantial increase in driving voltage.

In addition, the EIL, which facilitates injection of electrons from the cathode, may be formed on the ETL.

The EIL may include the heterocyclic compound of Formula 1 described above. In some embodiments well-known EIL materials, such as LiF, NaCl, CsF, $Li_2O$, or BaO, may be used to form the EIL. The deposition or coating conditions may be similar to those applied to form the HIL, although the deposition and coating conditions may vary according to the material that is used to form the EIL.

The EIL may have a thickness of about 1 Å to 100 Å, and in some embodiments, about 5 Å to about 90 Å. When the thickness of the EIL is within these ranges, the EIL may have good electron injection characteristics without a substantial increase in driving voltage.

Finally, the second electrode may be formed on the EIL by using, for example, vacuum deposition, sputtering, or the like. The second electrode may constitute a cathode or an anode. The material for forming the second electrode may include a metal, an alloy, or an electrically conductive compound, which are materials having a low work function, or a mixture thereof. Nonlimiting examples of such materials include lithium (Li), magnesium (Mg), aluminum (Al), aluminum-lithium (Al—Li), calcium (Ca), magnesium-indium (Mg—In), and magnesium-silver (Mg—Ag). In addition, in order to manufacture a top-emission organic light-emitting device, a transparent cathode formed of a transparent material such as ITO or IZO may be used as the second electrode.

According to embodiments of the present invention, the organic light-emitting device may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

According to embodiments, the first layer of the organic light-emitting device may be formed of the heterocyclic compound according to the embodiments described above by using a deposition method or a wet method of coating a solution of the heterocyclic compound according to the embodiments described above.

Hereinafter, the present invention will be described in detail with reference to synthesis examples of Compounds 3, 5, 11, 21, 24, 40, 58, 63 and 75 and other examples. However, these examples are for illustrative purposes only and are not intended to limit the scope of the present invention.

EXAMPLES

Synthesis Example 1

Synthesis of Compound 3

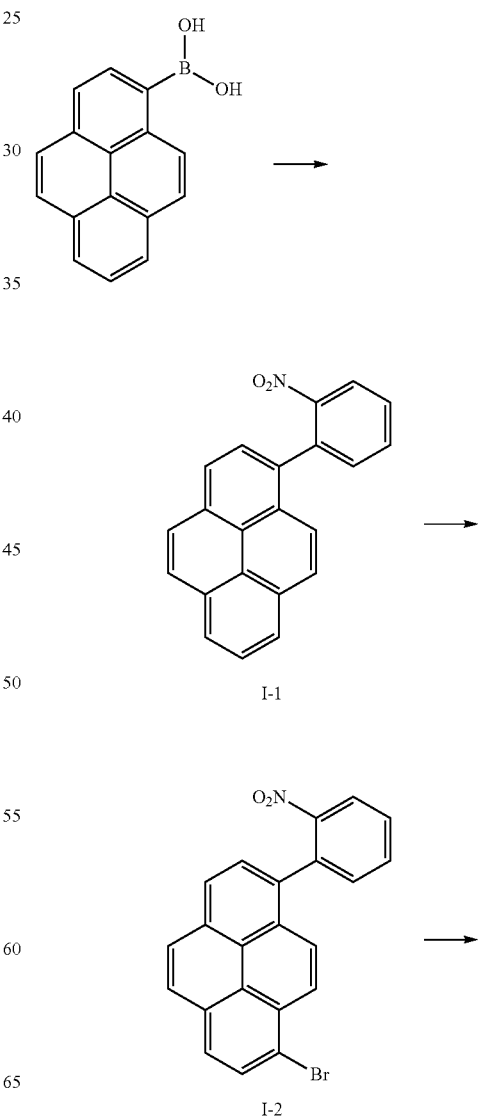

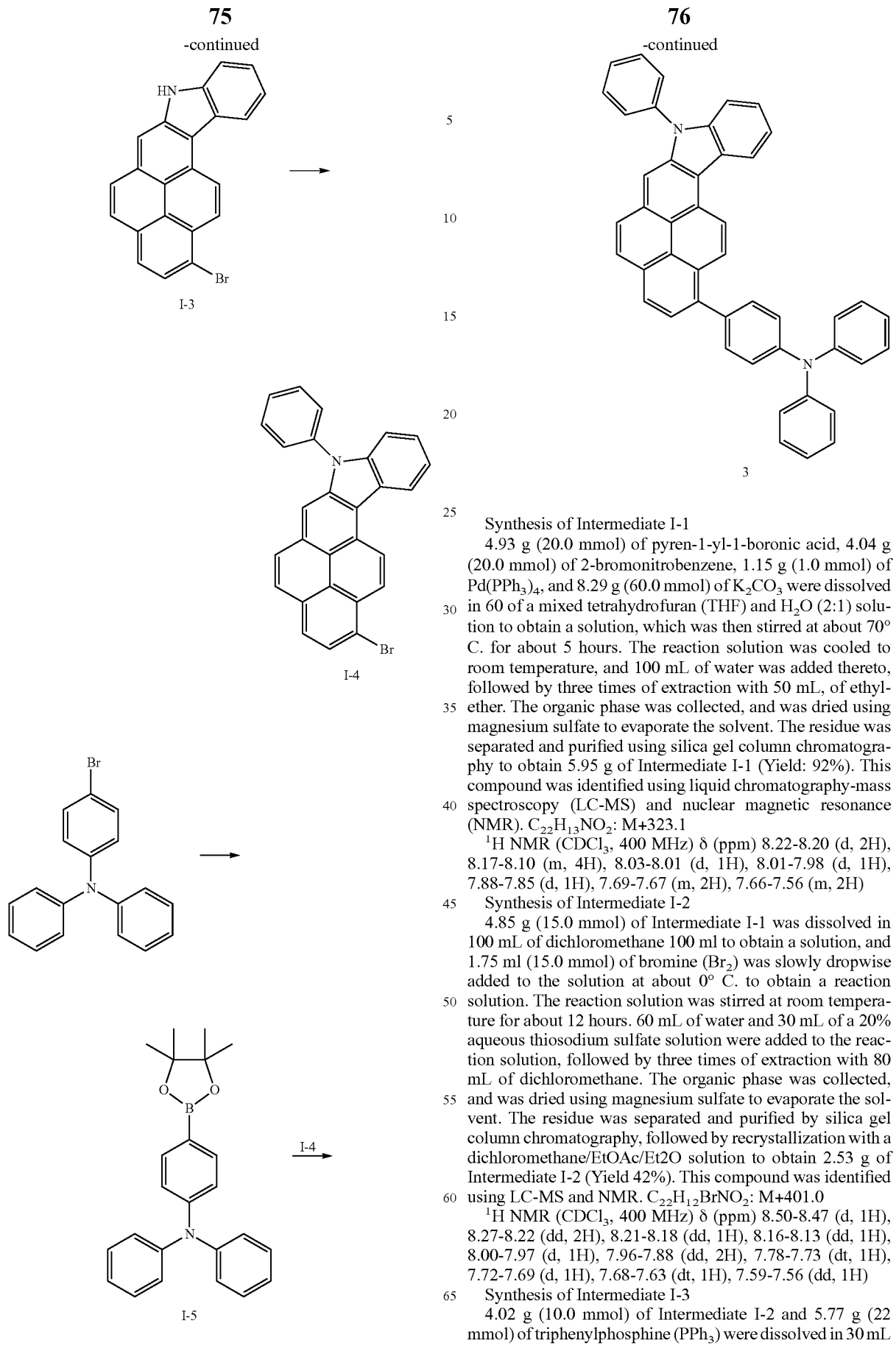

Synthesis of Intermediate I-1

4.93 g (20.0 mmol) of pyren-1-yl-1-boronic acid, 4.04 g (20.0 mmol) of 2-bromonitrobenzene, 1.15 g (1.0 mmol) of Pd(PPh$_3$)$_4$, and 8.29 g (60.0 mmol) of K$_2$CO$_3$ were dissolved in 60 of a mixed tetrahydrofuran (THF) and H$_2$O (2:1) solution to obtain a solution, which was then stirred at about 70° C. for about 5 hours. The reaction solution was cooled to room temperature, and 100 mL of water was added thereto, followed by three times of extraction with 50 mL, of ethylether. The organic phase was collected, and was dried using magnesium sulfate to evaporate the solvent. The residue was separated and purified using silica gel column chromatography to obtain 5.95 g of Intermediate I-1 (Yield: 92%). This compound was identified using liquid chromatography-mass spectroscopy (LC-MS) and nuclear magnetic resonance (NMR). C$_{22}$H$_{13}$NO$_2$: M+323.1

$^1$H NMR (CDCl$_3$, 400 MHz) δ (ppm) 8.22-8.20 (d, 2H), 8.17-8.10 (m, 4H), 8.03-8.01 (d, 1H), 8.01-7.98 (d, 1H), 7.88-7.85 (d, 1H), 7.69-7.67 (m, 2H), 7.66-7.56 (m, 2H)

Synthesis of Intermediate I-2

4.85 g (15.0 mmol) of Intermediate I-1 was dissolved in 100 mL of dichloromethane 100 ml to obtain a solution, and 1.75 ml (15.0 mmol) of bromine (Br$_2$) was slowly dropwise added to the solution at about 0° C. to obtain a reaction solution. The reaction solution was stirred at room temperature for about 12 hours. 60 mL of water and 30 mL of a 20% aqueous thiosodium sulfate solution were added to the reaction solution, followed by three times of extraction with 80 mL of dichloromethane. The organic phase was collected, and was dried using magnesium sulfate to evaporate the solvent. The residue was separated and purified by silica gel column chromatography, followed by recrystallization with a dichloromethane/EtOAc/Et2O solution to obtain 2.53 g of Intermediate I-2 (Yield 42%). This compound was identified using LC-MS and NMR. C$_{22}$H$_{12}$BrNO$_2$: M+401.0

$^1$H NMR (CDCl$_3$, 400 MHz) δ (ppm) 8.50-8.47 (d, 1H), 8.27-8.22 (dd, 2H), 8.21-8.18 (dd, 1H), 8.16-8.13 (dd, 1H), 8.00-7.97 (d, 1H), 7.96-7.88 (dd, 2H), 7.78-7.73 (dt, 1H), 7.72-7.69 (d, 1H), 7.68-7.63 (dt, 1H), 7.59-7.56 (dd, 1H)

Synthesis of Intermediate I-3

4.02 g (10.0 mmol) of Intermediate I-2 and 5.77 g (22 mmol) of triphenylphosphine (PPh$_3$) were dissolved in 30 mL of 1,2-dichlorobenzene to obtain a solution, which was then stirred at about 170° C. for about 12 hours. The reaction solution was cooled to room temperature, and the solvent was removed therefrom under vacuum conditions, followed by three times of extraction with 50 mL of water and 50 mL of dichloromethane. The organic phase was collected, and was dried using magnesium sulfate to evaporate the solvent. The residue was separated and purified using silica gel column chromatography to obtain 2.41 g of Intermediate I-3 (Yield: 65%). This compound was identified using LC-CM and NMR. $C_{22}H_{12}BrN$: M+369.0

$^1$H NMR (CDCl$_3$, 400 MHz) δ (ppm) 9.16-9.13 (d, 1H), 8.80-8.78 (d, 1H), 8.60 (s, 1H), 8.43-8.40 (d, 1H), 8.31-8.28 (d, 1H), 8.23-8.21 (d, 1H), 8.18 (s, 1H), 8.10-8.07 (d, 1H), 7.67-7.65 (d, 1H), 7.61-7.57 (dt, 1H), 7.50-7.46 (dt, 1H)

Synthesis of Intermediate I-4

3.70 g (10.0 mmol) of Intermediate I-3, 3.06 g (15.0 mmol) of iodobenzene, 0.19 g (1.0 mmol) of CuI, 0.05 g (0.2 mmol) of 18-Crown-6, and 4.15 g (30.0 mmol) of $K_2CO_3$ were dissolved in 30 mL of 1,3-dimethyl-3,4,5,6-tetrahydro-2 (1H)-pyrimidinone (DMPU) to obtain a solution, which was then stirred at about 170° C. for about 12 hours. The reaction solution was cooled to room temperature, followed by three times of extraction with 50 mL of water and 50 mL, of dichloromethane. The organic phase was collected, and was dried using magnesium, sulfate to evaporate the solvent. The residue was separated and purified using silica gel column chromatography to obtain 3.39 g of Intermediate I-4 (Yield: 76%). This compound was identified using LC-MS and NMR. $C_{28}H_{16}BrN$: M+445.0

$^1$H NMR (CDCl$_3$, 400 MHz) δ (ppm) 9.21-9.17 (dd, 1H), 8.86-8.84 (d, 8.46-8.35 (dd, 1H), 8.31-8.27 (dd, 1H), 8.25-8.17 (dd, 1H), 8.12-8.08 (d, 2H), 7.94-7.91 (d, 1H), 7.75-7.67 (m, 4H), 7.63-7.49 (m, 4H)

Synthesis of Intermediate I-5

3.24 g (10.0 mmol) of 4-bromotriphenylamine, 2.54 g (10.0 mmol) of bis(pinacolato)diborone, 0.36 g (0.5 mmol) of [1,1'-bis(diphenylphosphino)ferrocene]dichloro palladium (II) (hereinafter, $PdCl_2(dppf)_2$), and 2.94 g (30.0 mmol) of KOAc were dissolved in 40 mL of dimethylsulfoxide (DMSO) to obtain a solution, which was then stirred at about 80° C. for about 6 hours. The reaction solution was cooled to room temperature, followed by three times of extraction with 50 mL of water and 50 mL of diethylether. The organic phase was collected, and was dried using magnesium sulfate to evaporate the solvent. The residue was separated and purified using silica gel column chromatography to obtain 2.57 g of Intermediate I-5 (Yield: 89%). This compound was identified using LC-MS and NMR. $C_{24}H_{26}BNO_2$: M+371.2

$^1$H NMR (CDCl$_3$, 400 MHz) δ (ppm) 7.67-7.63 (m, 2H), 7.30-7.21 (m, 4H), 7.14-7.06 (m, 4H), 7.05-7.00 (m, 4H), 1.32 (s, 12H)

Synthesis of Compound 3

2.23 g (5.0 mmol) of Intermediate I-4, 1.86 g (5.0 mmol) of Intermediate I-5, 0.29 g (0.25 mmol) of Pd(PPh$_3$)$_4$, and 2.07 g (15.0 mmol) of $K_2CO_3$ were dissolved in 30 mL of a mixed solution THF/H$_2$O (2:1) to obtain a solution, which was then stirred at about 70° C. for about 5 hours. The reaction solution was cooled to room temperature, followed by three times of extraction with 50 mL of water and 50 mL of diethylether. The organic phase was collected, and was dried using magnesium sulfate to evaporate the solvent. The residue was separated and purified using silica gel column chromatography to obtain 2.11 g of Compound 3 (Yield: 72%). This compound was identified using LC-MS and NMR. $C_{46}H_{30}N_2$: M+610.2

$^1$H NMR (CDCl$_3$, 400 MHz) δ (ppm) 9.26-9.22 (d, 1H), 8.92-8.90 (dd, 1H), 8.43-8.41 (d, 1H), 8.34-8.31 (d, 1H), 8.27-8.24 (d, 1H), 8.10 (s, 1H), 8.03-7.98 (dd, 2H), 7.74-7.72 (m, 4H), 7.59-7.52 (m, 6H), 7.35-7.22 (m, 10), 7.10-7.05 (dt, 2H)

Synthesis Example 2

Synthesis of Compound 5

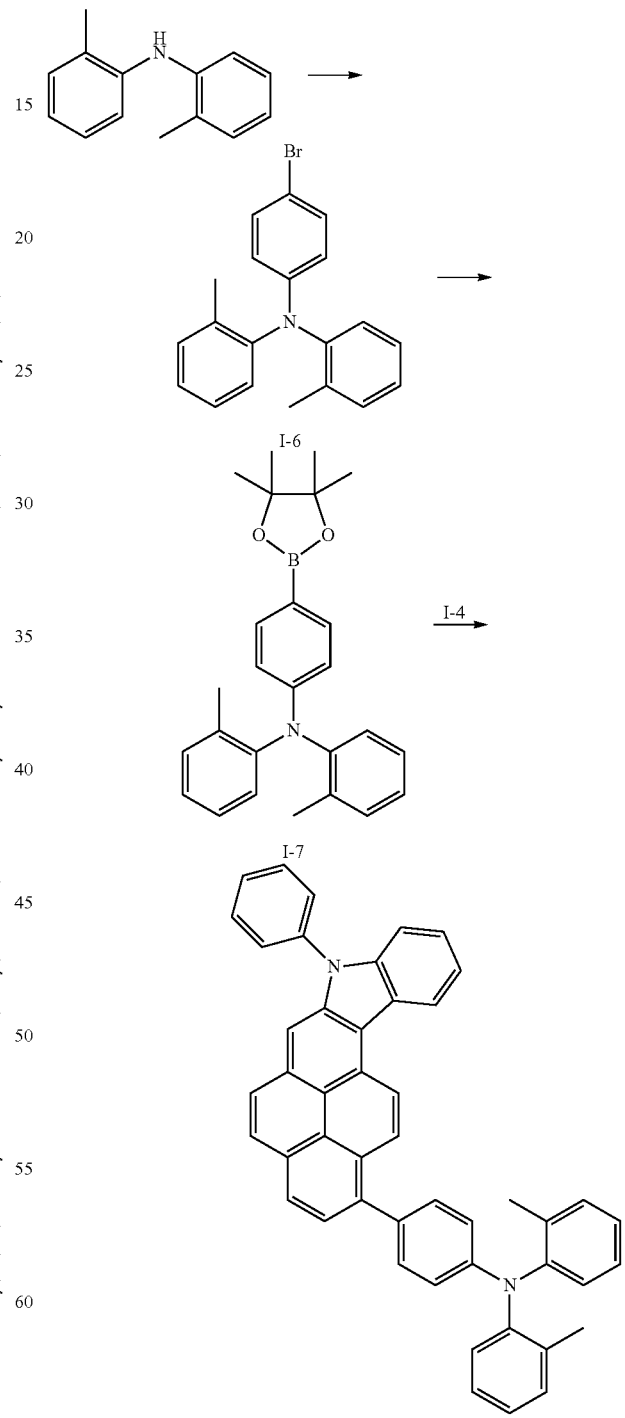

Synthesis of Intermediate I-6

1.97 g (10.0 mmol) of di-ortho-tolylamine, 4.24 g (15.0 mmol) of 4-bromoiodobenzene, 0.18 g (0.2 mmol) of Pd$_2$(dba)$_3$, 0.04 g (0.4 mmol) of PtBu$_3$, and 1.44 g (15.0 mmol) of KOtBu were dissolved in 40 mL of toluene to obtain a solution, which was then stirred at about 85° C. for about 4 hours. The reaction solution was cooled to room temperature, followed by three times of extraction with 30 mL of water and 30 mL of diethylether. The organic phase was collected, and was dried using magnesium sulfate to evaporate the solvent. The residue was separated and purified using silica gel column chromatography to obtain 2.18 g of Intermediate I-6 (Yield: 62%). This compound was identified using LC-MS and NMR. C$_{20}$H$_{18}$BrN: M+351.1

$^1$H NMR (CDCl$_3$, 400 MHz) δ (ppm) 7.29-7.24 (m, 4H), 7.18-7.13 (dt, 2H), 6.92-6.84 (m, 4H), 1.96 (s, 6H)

Synthesis of Intermediate I-7

3.52 g (10.0 mmol) of Intermediate I-6, 2.54 g (10.0 mmol) of bis(pinacolato)diborone, 0.36 g (0.5 mmol) of PdCl$_2$(dppf)$_2$, and 2.94 g (30.0 mmol) of KOAc were dissolved in 40 mL of DMSO to obtain a solution, which was then stirred at about 80° C. for about 6 hours. The reaction solution was cooled to room temperature, followed by three times of extraction with 50 mL of water and 50 mL of diethylether. The organic phase was collected, and was dried using magnesium sulfate to evaporate the solvent. The residue was separated and purified using silica gel column chromatography to obtain 3.03 g of Intermediate I-7 (Yield: 76%). This compound was identified using LC-MS and NMR. C$_{26}$H$_{30}$BNO$_2$: M+399.2

$^1$H NMR (CDCl$_3$, 400 MHz) δ (ppm) 7.62-7.60 (d, 1H), 7.22-7.20 (dd, 2H), 7.18-7.07 (m, 4H), 7.00-6.98 (dd, 2H), 6.63-6.60 (d, 2H), 2.02 (s, 6H), 1.33 (s, 12H)

Synthesis of Compound 5

2.42 g of Compound 5 was synthesized from Intermediate I-5 and Intermediate I-4 in the same manner as in the synthesis of Compound 3 (Yield: 76%). This compound was identified using LC-MS and NMR. C$_{48}$H$_{34}$N$_2$: M+638.3

$^1$H NMR (CDCl$_3$, 400 MHz) δ (ppm) 8.96-8.94 (d, 1H), 8.23-8.17 (m, 2H), 8.09-8.07 (d, 1H), 8.04 (s, 1H), 7.94-7.88 (m, 3H), 7.51-7.47 (m, 4H), 7.37-7.31 (m, 4H), 7.28-7.22 (m, 4H), 7.17-7.13 (dt, 2H), 6.90-6.86 (dt, 2H), 6.78-6.73 (m, 4H), 2.02 (s, 6H)

Synthesis Example 3

Synthesis of Compound 11

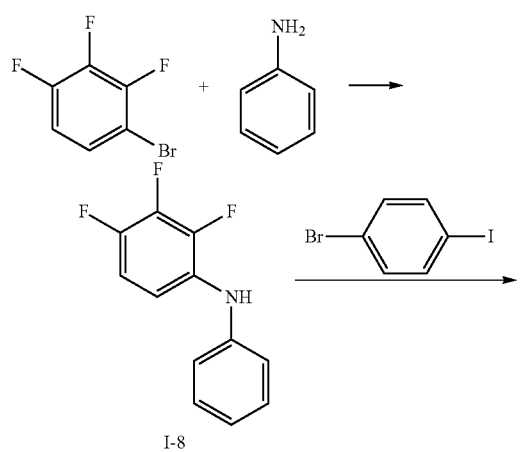

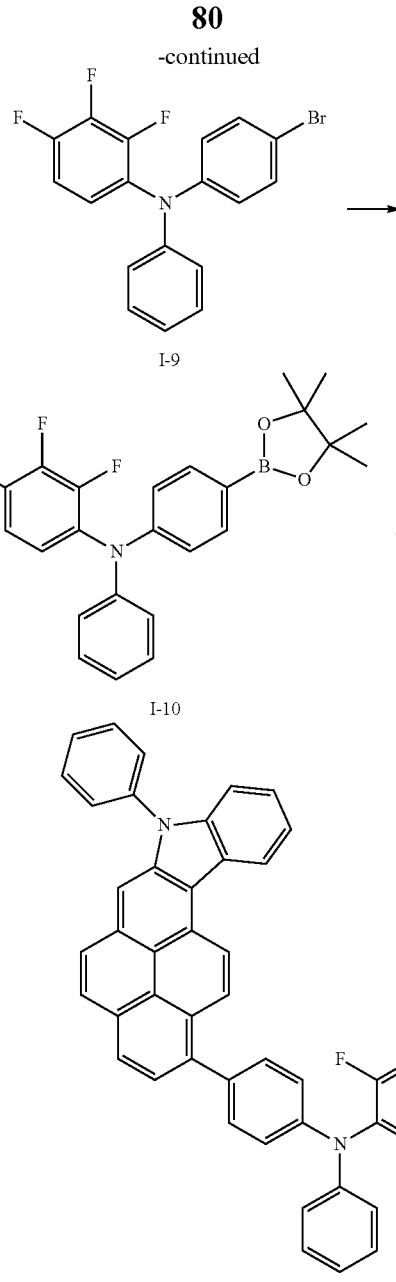

Synthesis of Intermediate I-8

4.22 g (20.0 mmol) of 1-bromo-2,3,4-trifluorobenzene, 2.79 g (30.0 mmol) of aniline. 0.37 g (0.4 mmol) of Pd$_2$(dba)$_3$, 0.08 g (0.4 mmol) of PtBu$_3$, and 2.88 g (30.0 mmol) of KOtBu were dissolved in 60 mL of toluene to obtain a solution, which was then stirred at about 85° C. for about 4 hours. The reaction solution was cooled to room temperature, followed by three times of extraction with 50 mL of water and 50 mL of diethylether. The organic phase was collected, and was dried using magnesium sulfate to evaporate the solvent. The residue was separated and purified using silica gel column chromatography to obtain 3.93 g of Intermediate I-8 (Yield: 88%). This compound was identified using LC-MS and NMR. C$_{12}$H$_8$F$_3$N: M+223.1

$^1$H NMR (CDCl$_3$, 400 MHz) δ (ppm) 7.34-7.26 (m, 2H), 7.04-7.00 (m, 3H), 6.99-6.92 (m, 1H), 6.87-6.77 (m, 1H), 5.62 (s, 1H)

Synthesis of Intermediate I-9

2.23 g (10.0 mmol) of Intermediate I-8, 4.23 g (15.0 mmol) of 4-bromoiodobenzene, 0.18 g (0.2 mmol) of $Pd_2(dba)_3$, 0.04 g (0.4 mmol) of $PtBu_3$, and 1.44 g (15.0 mmol) of KOtBu were dissolved in 40 mL of toluene to obtain a solution, which was then stirred at about 85° C. for about 4 hours. The reaction solution was cooled to room temperature, followed by three times of extraction with 30 mL of water and 30 mL of diethylether. The organic phase was collected, and was dried using magnesium sulfate to evaporate the solvent. The residue was separated and purified using silica gel column chromatography to obtain 2.38 g of intermediate I-9 (Yield: 63%). This compound was identified using LC-MS and NMR. $C_{18}H_{11}BrF_3N$: M+377.0

$^1$H NMR ($CDCl_3$, 400 MHz) δ (ppm) 7.38-7.31 (m, 2H), 7.30-7.25 (m, 2H), 7.11-7.07 (dt, 1H), 7.06-7.01 (m, 2H), 6.98-6.91 (m, 2H), 6.88-6.85 (m, 2H)

Synthesis of Intermediate I-10

3.78 g (10.0 mmol) of Intermediate I-9, 2.54 g (10.0 mmol) of bis(pinacolato)diborone, 0.36 g (0.5 mmol) of $PdCl_2(dppf)_2$, and 2.94 g (30.0 mmol) of KOAc were dissolved in 40 mL of DMSO to obtain a solution, which was then stirred at about 80° C. for about 6 hours. The reaction solution was cooled to room temperature, followed by three times of extraction with 50 mL of water and 50 mL of diethylether. The In organic phase was collected, and was dried using magnesium sulfate to evaporate the solvent. The residue was separated and purified using silica gel column chromatography to obtain 3.40 g of Intermediate I-10 (Yield: 80%). This compound was identified using LC-MS and NMR. $C_{24}H_{23}BF_3NO_2$: M+425.2

$^1$H NMR ($CDCl_3$, 400 MHz) δ (ppm) 7.72-7.68 (m, 2H), 7.32-7.25 (m, 2H), 7.13-7.05 (m, 3H), 6.99-6.85 (m, 4H), 1.35 (s, 12H)

Synthesis of Compound 11

2.39 g of Compound II was synthesized from Intermediate I-10 and Intermediate I-4 in the same manner as in the synthesis of Compound 3 (Yield: 72%). This compound was identified using LC-MS and NMR. $C_{46}H_{27}F_3N_2$: M+664.2

$^1$H NMR ($CDCl_3$, 400 MHz) δ (ppm) 9.25-9.22 (d, 1H), 8.92-8.89 (d, 1H), 8.43-8.40 (d, 1H), 8.33-8.30 (d, 1H), 8.23-8.20 (d, 1H), 8.10 (s, 1H), 7.99 (t, 2H), 7.74-7.72 (m, 4H), 7.62-7.53 (m, 6H), 7.34 (dt, 2H), 7.18-7.15 (d, 4H), 7.12-6.91 (m, 3H)

Synthesis Example 4

Synthesis of Compound 21

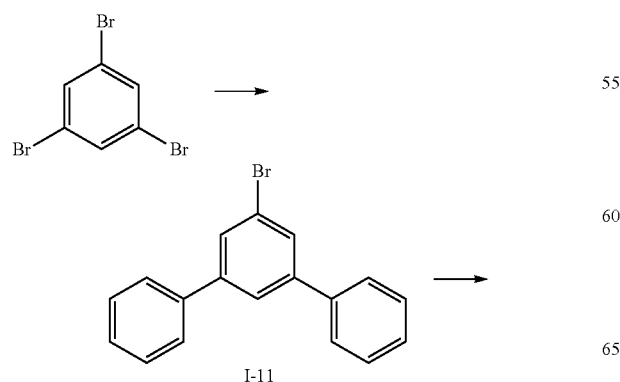

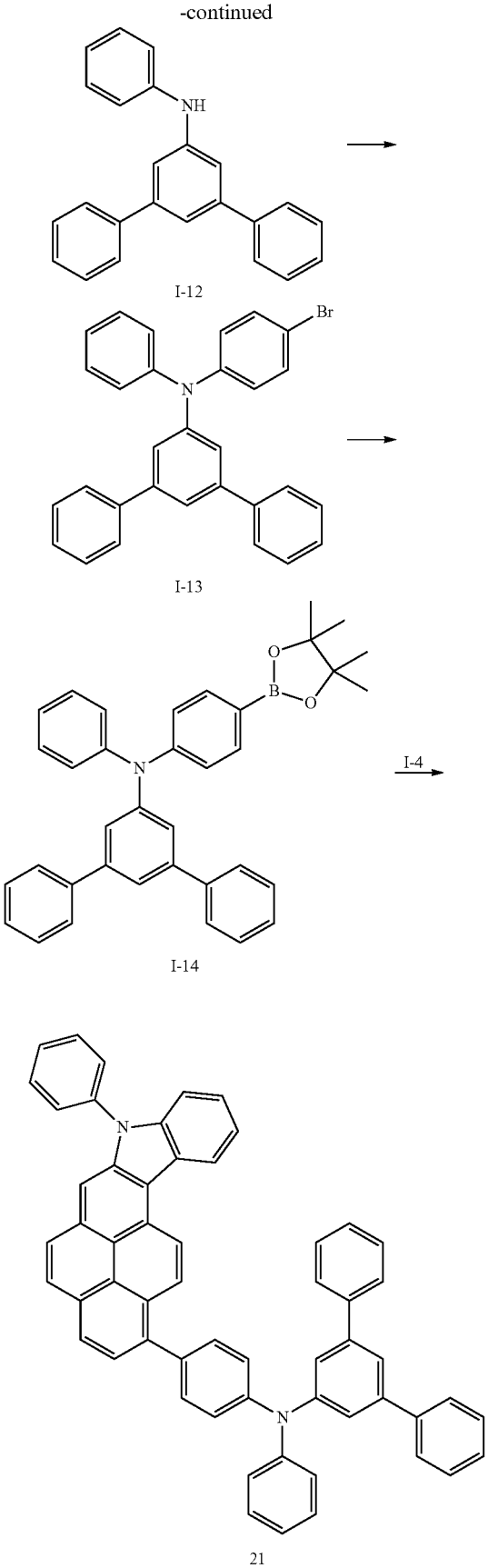

Synthesis of Intermediate I-11

6.3 g (20.0 mmol) of 1,3,5-tribromobenzene, 4.88 g (40.0 mmol) of 1-phenylboronic acid, 2.31 g (2.0 mmol) of Pd(PPh$_3$)$_1$, and 16.6 g (120.0 mmol) of K$_2$CO$_3$ were dissolved in 120 mL of a mixed solution THF/H$_2$O (2:1) to obtain a solution, which was then stirred at about 70° C. for about 5 hours. The reaction solution was cooled to room temperature, followed by three times of extraction with 120 mL of water and 100 mL of diethylether. The organic phase was collected, and was dried using magnesium sulfate to evaporate the solvent. The residue was separated and purified using silica gel column chromatography to obtain 3.83 g of Intermediate I-11 (Yield: 62%). This compound was in identified using LC-MS and NMR. C$_{18}$H$_{13}$Br: M+308.2

$^1$H NMR (CDCl$_3$, 400 MHz) δ (ppm) 7.70 (s, 3H), 7.62-7.58 (m, 4H), 7.48-7.47 (t, 1H), 7.46-7.42 (m, 3H), 7.41-7.35 (m, 2H)

Synthesis of Intermediate I-12

2.73 g of Intermediate I-12 was synthesized from Intermediate I-11 and aniline in the same manner as in the synthesis of Intermediate I-8 (Yield: 85%). This compound was identified using LC-MS and NMR. C$_{24}$H$_{19}$N: M+321.2

$^1$H NMR (CDCl$_3$, 400 MHz) δ (ppm) 7.76-7.75 (t, 1H), 7.54-7.50 (m, 6H), 7.34-7.22 (m, 8H), 7.13-7.11 (m, 2H), 7.10-7.06 (dt, 1H), 6.52 (s, 1H)

Synthesis of Intermediate I-13

3.14 g of Intermediate I-13 was synthesized from Intermediate I-12 in the same manner as in the synthesis of Intermediate I-9 (Yield: 66%). This compound was identified using LC-MS and NMR. C$_{30}$H$_{22}$BrN: M+475.1

$^1$H NMR (CDCl$_3$, 400 MHz) δ (ppm) 7.90 (t, 1H), 7.50 (d, 2H), 7.44-7.43 (d, 8H), 7.34-7.29 (m, 6H), 7.12-7.10 (d, 2H), 7.04-7.00 (m, 1H), 6.91-6.89 (m, 2H)

Synthesis of Intermediate I-14

4.08 g of Intermediate I-14 was synthesized from Intermediate I-13 in the same manner as in the synthesis of Intermediate I-10 (Yield: 78%). This compound was identified using LC-MS and NMR. C$_{36}$H$_{34}$BNO$_2$: M+523.3

$^1$H NMR (CDCl$_3$, 400 MHz) δ (ppm) 7.91 (t, 1H), 7.71-7.67 (m, 2H), 7.50 (d, 2H), 7.44-7.42 (d, 8H), 7.34-7.29 (m, 4H), 7.24-7.22 (d, 2H), 7.14-7.10 (m, 1H), 6.81-6.79 (m, 2H), 1.35 (s, 12H)

Synthesis of Compound 21

2.86 g of Compound 21 was synthesized from Intermediate I-14 and Intermediate I-4 in the same manner as in the synthesis of Compound 3 (Yield: 75%). This compound was identified using LC-MS and NMR. C$_{58}$H$_{38}$N$_2$: M+762.3

$^1$H NMR (CDCl$_3$, 400 MHz) δ (ppm) 9.16-9.14 (d, 1H), 8.73-8.67 (m, 2H), 8.46-8.44 (d, 1H), 8.24 (s, 1H), 7.94-7.90 (m, 4H), 7.62-7.58 (m, 6H), 7.54-7.53 (d, 8H), 7.45-7.39 (m, 10H), 7.24-7.20 (m, 1H), 7.15-7.12 (m, 2H), 7.01-6.99 (d, 21-1)

Synthesis Example 5

Synthesis of Compound 24

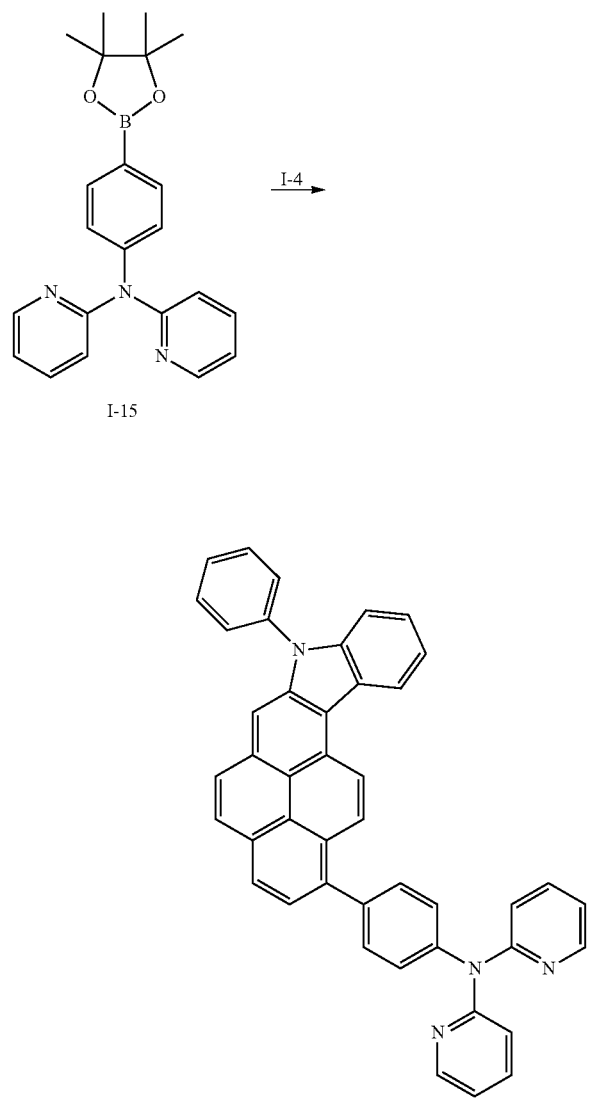

2.18 g of Compound 24 was synthesized from Intermediate I-4 and Intermediate I-15, which was synthesized using a known method, in the same manner as in the synthesis of Compound 3 (Yield: 71%). This compound was identified using LC-MS and NMR. C$_{44}$H$_{28}$N$_4$: M+612.2

$^1$H NMR (CDCl$_3$, 400 MHz) δ (ppm) 9.23-9.21 (d, 1H), 8.63-8.49 (m, 4H), 8.29-8.27 (d, 1H), 8.14 (s, 1H), 7.94-7.88 (m, 3H), 7.78-7.68 (m, 8H), 7.47-7.40 (m, 6H), 7.11-7.08 (m, 2H), 7.02-6.99 (m, 21-1)

Synthesis Example 6

Synthesis of Compound 40

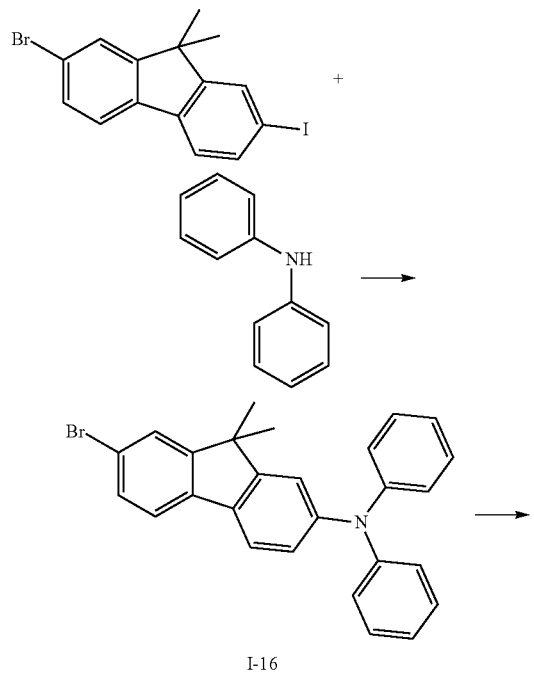

Synthesis of Intermediate I-16

3.04 g of Intermediate I-16 was synthesized from 2-bromo-7-iodo-9,9-dimethylfluorene and diphenylamine in the same manner as in the synthesis of Intermediate I-13 (Yield: 69%). This compound was identified using LC-MS and NMR. $C_{27}H_{22}BrN$: M+439.1

$^1$H NMR (CDCl$_3$, 400 MHz) δ (ppm) 8.09-8.07 (d, 1H), 7.94-7.92 (d, 1H), 7.74-7.68 (m, 2H), 7.53-7.49 (t, 4H), 7.30 (s, 1H), 7.24-7.20 (m, 2H), 7.04-7.02 (m, 1H), 6.98-6.96 (d, 4H), 1.86 (s, 6H)

Synthesis of Intermediate I-17

3.99 g of Intermediate I-17 was synthesized from Intermediate I-16 in the same manner as in the synthesis of Intermediate I-14 (Yield: 82%). This compound was identified using LC-MS and NMR. $C_{31}H_{34}BNO_2$: M+487.3

$^1$H NMR (CDCl$_3$, 400 MHz) δ (ppm) 8.10-8.08 (d, 1H), 7.95-7.92 (m, 2H), 7.79-7.77 (d, 1H), 7.53-7.49 (m, 4H), 7.36-7.35 (m, 1H), 7.24-7.20 (m, 2H), 7.14-7.12 (dd, 11-1), 6.98-6.96 (m, 4H), 1.86 (s, 6H), 1.36 (s, 12H)

Synthesis of Compound 40

2.65 g of Compound 40 was synthesized from Intermediate I-17 and Intermediate I-4 in the same manner as in the synthesis of Compound 3 (Yield: 73%). This compound was identified using LC-MS and NMR. $C_{55}H_{38}N_2$: M+726.3

1H NMR (CDCl$_3$, 400 MHz) δ (ppm) 9.17-9.15 (d, 1H), 8.73-8.67 (m, 2H), 8.57-8.54 (m, 21-1), 8.34-8.32 (d, 1H), 8.28-8.26 (d, 1H), 8.03-8.01 (d, 1H), 7.85-7.83 (d, 1H), 7.69-7.67 (m, 4H), 7.55-7.49 (m, 8H), 7.35-7.33 (d, 1H), 7.30-7.29 (d, 1H), 7.24 (d, 1H), 7.13-7.11 (dd, 1H), 7.04-7.00 (dt, 2H), 6.94-6.92 (dd, 1H), 6.88-6.86 (dd, 4H), 1.85 (s, 6H)

Synthesis Example 7

Synthesis of Compound 58

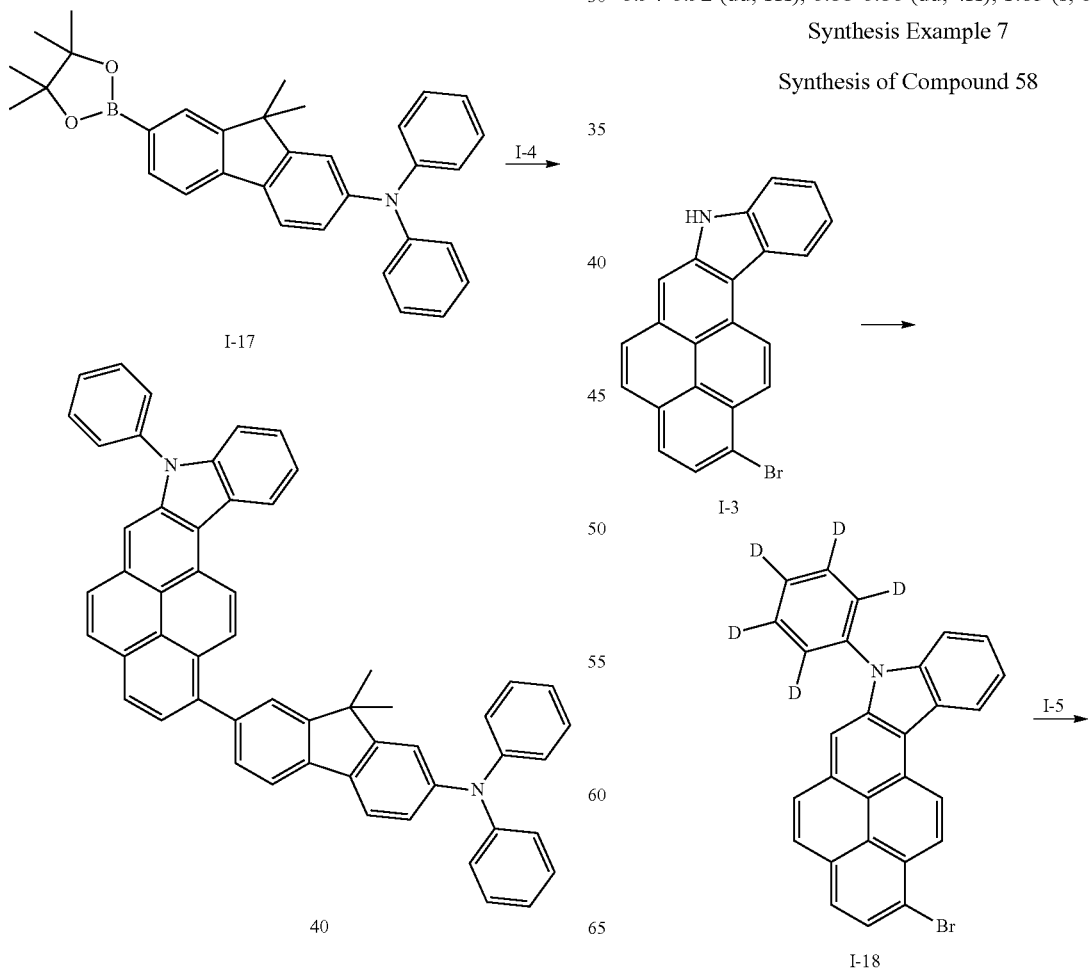

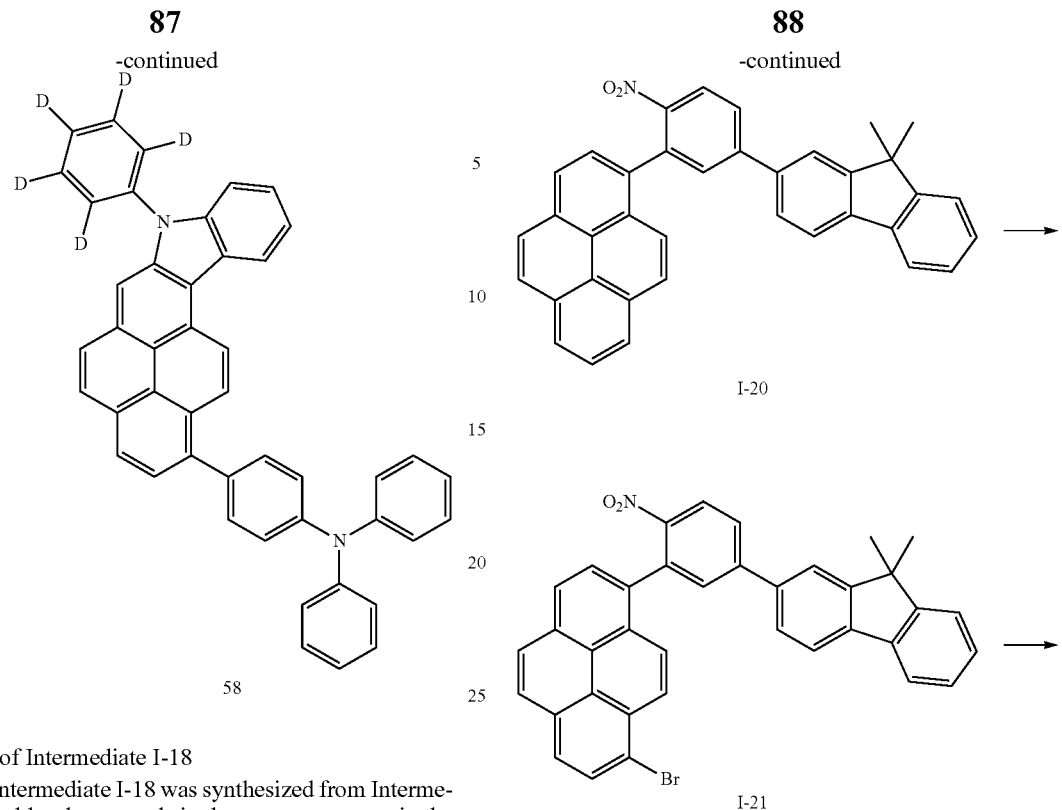

58

Synthesis of Intermediate I-18

3.48 g of Intermediate I-18 was synthesized from Intermediate I-3 and chlorobenzene-d$_5$ in the same manner as in the synthesis of Intermediate I-4 (Yield: 77%). This compound was identified using LC-MS and NMR. $C_{28}H_{11}D_5BrN$: M+450.1

$^1$H NMR (CDCl$_3$, 400 MHz) δ (ppm) 8.89-8.87 (d, 1H), 8.85-8.83 (d, 1H), 8.44-8.42 (d, 1H), 8.23-8.19 (m, 2H), 8.14 (s, 1), 8.03-7.97 (dd, 2H), 7.37-7.29 (m, 3H)

Synthesis of Compound 58

2.52 g of Compound 58 was synthesized from Intermediate I-18 and Intermediate I-5 in the same manner as in the synthesis or Compound 3 (Yield: 82%). This compound was identified using LC-MS and NMR. $C_{46}H_{25}D_5N_2$: M+615.3

$^1$H NMR (CDCl$_3$, 400 MHz) δ (ppm) 9.26-9.24 (d, 1H), 8.63-8.57 (m, 2H), 8.49-8.47 (d, 1H), 8.44 (s, 1H), 8.14-8.10 (t, 3H), 7.65-7.59 (m, 9H), 7.34-7.32 (m, 2H), 7.25-7.21 (m, 2H), 7.10-7.08 (dd, 4H)

Synthesis Example 8

Synthesis of Compound 63

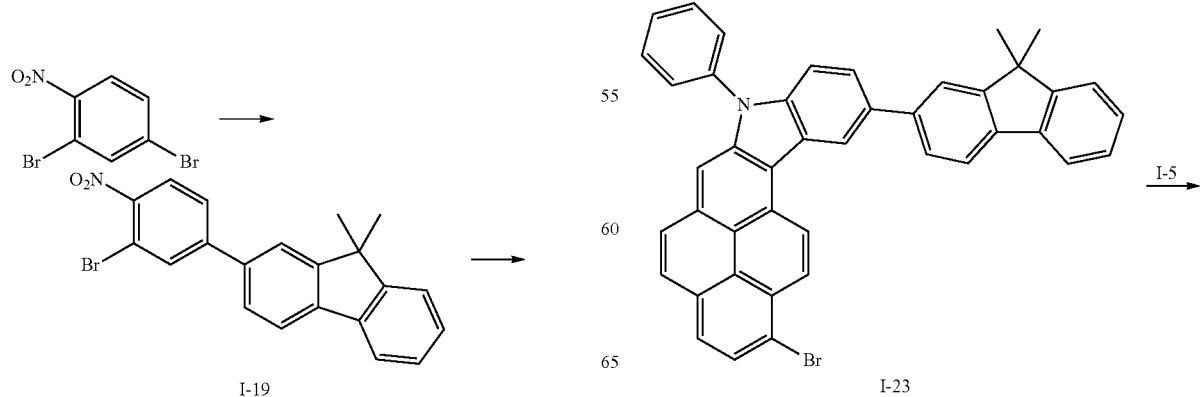

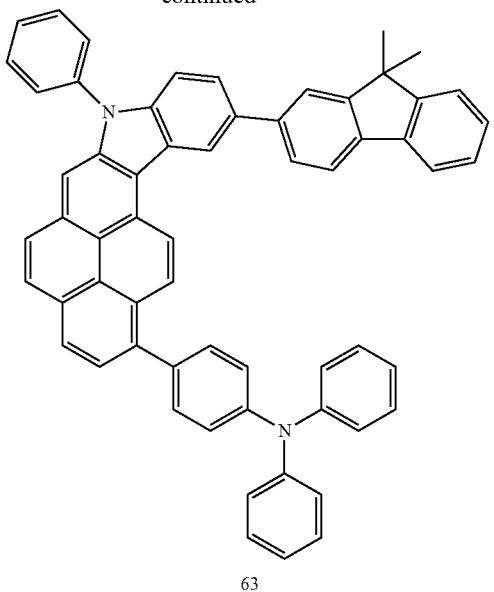

63

Synthesis of Intermediate I-19

5.62 g (20.0 mmol) of 2,4-dibromo-1-nitrobenzene, 4.52 g (19.0 mmol) of dimethylfluorene-2-boronic acid, 1.15 g (1.0 mmol) of Pd(PPh$_3$)$_4$, and 8.29 g (60.0 mmol) of K$_2$CO$_3$ were dissolved in 80 mL of a mixed solution THF/H$_2$O (2:1) to obtain a solution, which was then stirred at about 70° C. for about 5 hours. The reaction solution was cooled to room temperature, followed by three times of extraction with 60 mL of water and 60 mL of diethylether. The organic phase was collected, and was dried using magnesium sulfate to evaporate the solvent. The residue was separated and purified using silica gel column chromatography to obtain 4.57 g of Intermediate I-19 (Yield: 58%) This compound was identified using LC-MS and NMR. C$_{21}$H$_{16}$BrNO$_2$: M+393.0

$^1$H NMR (CDCl$_3$, 400 MHz) δ (ppm) 8.06-8.04 (d, 1H), 7.79-7.77 (m, 1H), 7.65-7.64 (d, 1H), 7.60-7.57 (dd, 1H), 7.50-7.48 (dd, 1H), 7.44-7.41 (m, 1H), 7.28-7.26 (dd, 1H), 7.10-7.03 (m, 3H), 1.90 (s, 6H)

Synthesis of Intermediate I-20

4.28 g of Intermediate I-20 was synthesized from Intermediate I-19 and pyren-1-yl-boronic acid in the same manner as in the synthesis of Intermediate I-1 (Yield: 83%). This compound was identified using LC-MS and NMR. C$_{37}$H$_{25}$NO$_2$: M+515.2

$^1$H NMR (CDCl$_3$, 400 MHz) δ (ppm) 8.67-8.66 (d, 1H), 8.38-8.36 (d, 1H), 8.21-8.06 (m, 8H), 7.80-7.77 (m, 2H), 7.50-7.48 (m, 1H), 7.34-7.31 (m, 1H), 7.21-7.18 (dd, 1H), 7.09-7.03 (m, 4H), 1.89 (s, 6H)

Synthesis of Intermediate I-21

2.79 g of Intermediate I-21 was synthesized from Intermediate I-20 in the same manner as in the synthesis of Intermediate I-2 (Yield: 47%). This compound was identified using LC-MS and NMR. C$_{37}$H$_{24}$BrNO$_2$: M+593.1

$^1$H NMR (CDCl$_3$, 400 MHz) δ (ppm) 8.85-8.83 (d, 1H), 8.47-8.46 (dd, 1H), 8.34-8.32 (d, 1H), 8.13-8.04 (m, 4H), 7.98-7.93 (m, 2H), 7.79-7.77 (m, 2H), 7.50-7.48 (dd, 1H), 7.24-7.21 (dt, 1H), 7.11-7.08 (m, 1H), 6.99-6.93 (m, 4H), 1.87 (s, 6H)

Synthesis of Intermediate I-22

3.21 g of Intermediate I-22 was synthesized from Intermediate I-21 in the same manner as in the synthesis of Intermediate I-3 (Yield: 57%). This compound was identified using LC-MS and NMR. C$_{37}$H$_{24}$BrN: M+561.1

$^1$H NMR (CDCl$_3$, 400 MHz) δ (ppm) 10.38 (s, 1H), 8.85-8.77 (dd, 2H), 8.49-8.47 (d, 1H), 8.26-8.24 (d, 1H), 8.02-7.96 (m, 4H), 7.79-7.77 (dd, 1H), 7.50-7.48 (d, 1H), 7.44-7.42 (d, 1H), 7.34-7.32 (dd, 1H), 7.24-7.20 (dt, 1H), 7.02-6.93 (m, 41-1), 1.87 (s, 6H)

Synthesis of Intermediate I-23

4.98 g of Intermediate I-23 was synthesized from Intermediate I-22 in the same manner as in the synthesis of Intermediate I-4 (Yield: 78%). This compound was identified using LC-MS and NMR. C$_{43}$H$_{28}$BrN: M+637.1

$^1$H NMR (CDCl$_3$, 400 MHz) δ (ppm) 9.05-9.02 (dd, 2H), 8.54-8.52 (d, 1H), 8.31-8.29 (d, 1H), 8.19 (s, 1H), 8.13-8.07 (dd, 2H), 7.93-7.91 (d, 1H), 7.79-7.77 (dd, 1H), 7.67 (dd, 1H), 7.51-7.47 (m, 5H), 7.37-7.31 (m, 1H), 7.24-7.21 (dt, 1H), 7.02-6.93 (m, 5H), 1.86 (d, 6H)

Synthesis of Compound 63

2.93 g of Compound 63 was synthesized from Intermediate I-23 and Intermediate I-5 in the same manner as in the synthesis of Compound 3 (Yield: 73%). This compound was identified using LC-MS and NMR. C$_{61}$H$_{42}$N$_2$: M+802.3

$^1$H NMR (CDCl$_3$, 400 MHz) δ (ppm) 9.11-9.09 (d, 1H), 8.60-8.57 (d, 1H), 8.49-8.48 (d, 1H), 8.29 (s, 1H), 8.23-8.18 (m, 4H), 7.99-7.97 (dd, 1H), 7.77 (dd, 1H), 7.61-7.58 (m, 5H), 7.46-7.39 (m, 7.34-7.31 (dt, 1H), 7.22-7.13 (m, 5H), 7.04-7.00 (m, 2H), 6.95-6.91 (m, 2H), 6.80-6.78 (m, 4H), 1.86 (s, 6H)

Synthesis Example 9

Synthesis of Compound 75

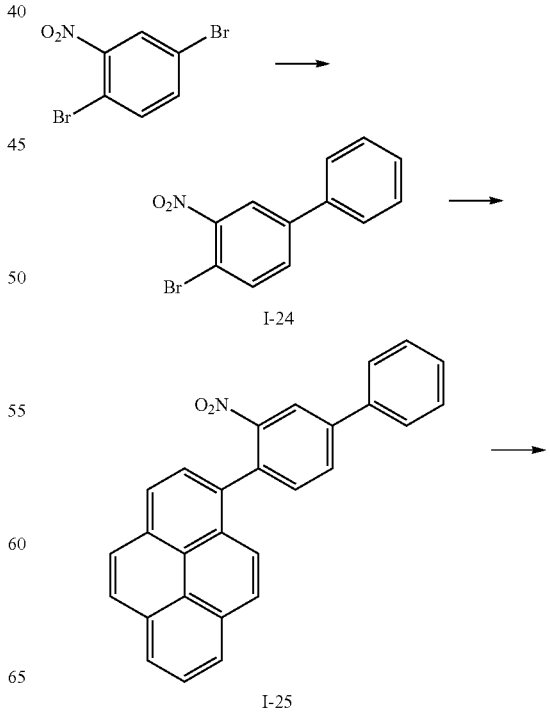

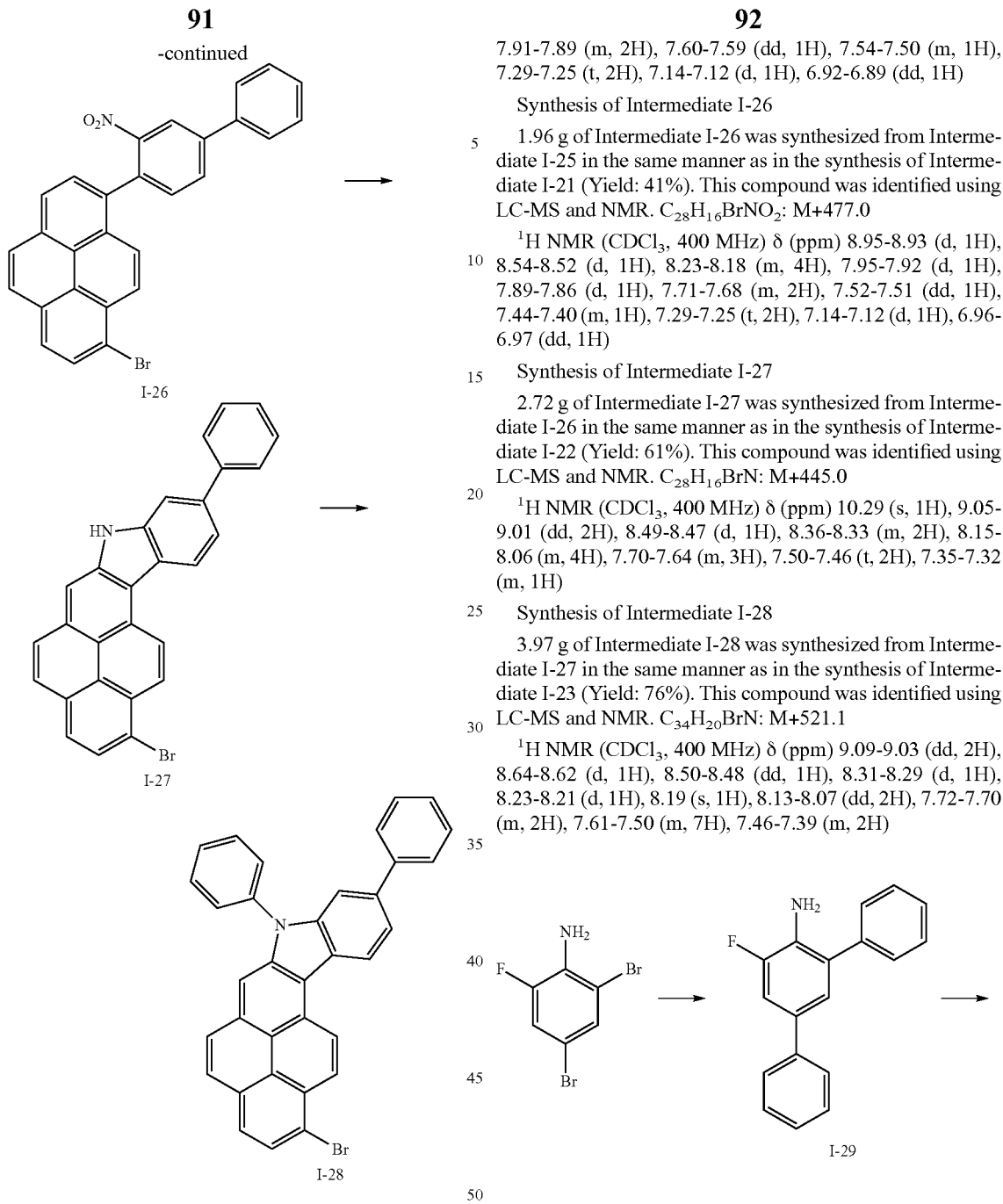

7.91-7.89 (m, 2H), 7.60-7.59 (dd, 1H), 7.54-7.50 (m, 1H), 7.29-7.25 (t, 2H), 7.14-7.12 (d, 1H), 6.92-6.89 (dd, 1H)

Synthesis of Intermediate I-26

1.96 g of Intermediate I-26 was synthesized from Intermediate I-25 in the same manner as in the synthesis of Intermediate I-21 (Yield: 41%). This compound was identified using LC-MS and NMR. $C_{28}H_{16}BrNO_2$: M+477.0

$^1$H NMR (CDCl$_3$, 400 MHz) δ (ppm) 8.95-8.93 (d, 1H), 8.54-8.52 (d, 1H), 8.23-8.18 (m, 4H), 7.95-7.92 (d, 1H), 7.89-7.86 (d, 1H), 7.71-7.68 (m, 2H), 7.52-7.51 (dd, 1H), 7.44-7.40 (m, 1H), 7.29-7.25 (t, 2H), 7.14-7.12 (d, 1H), 6.96-6.97 (dd, 1H)

Synthesis of Intermediate I-27

2.72 g of Intermediate I-27 was synthesized from Intermediate I-26 in the same manner as in the synthesis of Intermediate I-22 (Yield: 61%). This compound was identified using LC-MS and NMR. $C_{28}H_{16}BrN$: M+445.0

$^1$H NMR (CDCl$_3$, 400 MHz) δ (ppm) 10.29 (s, 1H), 9.05-9.01 (dd, 2H), 8.49-8.47 (d, 1H), 8.36-8.33 (m, 2H), 8.15-8.06 (m, 4H), 7.70-7.64 (m, 3H), 7.50-7.46 (t, 2H), 7.35-7.32 (m, 1H)

Synthesis of Intermediate I-28

3.97 g of Intermediate I-28 was synthesized from Intermediate I-27 in the same manner as in the synthesis of Intermediate I-23 (Yield: 76%). This compound was identified using LC-MS and NMR. $C_{34}H_{20}BrN$: M+521.1

$^1$H NMR (CDCl$_3$, 400 MHz) δ (ppm) 9.09-9.03 (dd, 2H), 8.64-8.62 (d, 1H), 8.50-8.48 (dd, 1H), 8.31-8.29 (d, 1H), 8.23-8.21 (d, 1H), 8.19 (s, 1H), 8.13-8.07 (dd, 2H), 7.72-7.70 (m, 2H), 7.61-7.50 (m, 7H), 7.46-7.39 (m, 2H)

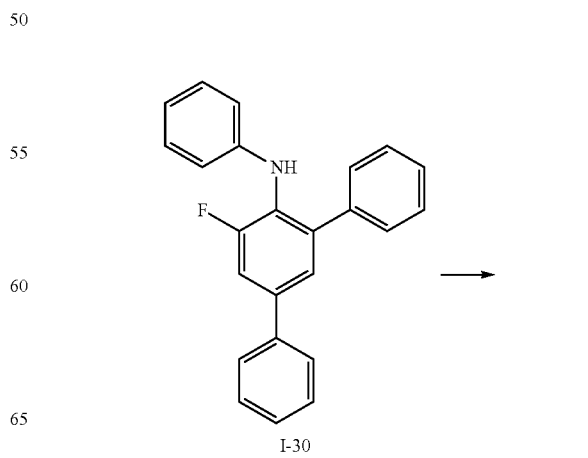

Synthesis of Intermediate I-24

3.39 g of Intermediate I-24 was synthesized from 1,4-dibromo-2-nitrobenzene and phenylboronic acid in the same manner as in the synthesis of Intermediate I-19 (Yield: 61%). This compound was identified using LC-MS and NMR. $C_{12}H_8BrNO_2$: M+277.0

$^1$H NMR (CDCl$_3$, 400 MHz) δ (ppm) 8.15-8.14 (dd, 1H), 7.80-7.78 (m, 2H), 7.49-7.47 (d, 1H), 7.34-7.30 (m, 1H), 7.19-7.15 (m, 2H), 7.11-7.08 (dd, 1H)

Synthesis of Intermediate I-25

3.16 g of Intermediate I-25 was synthesized from Intermediate I-24 in the same manner as in the synthesis of Intermediate I-20 (Yield: 79%). This compound was identified using LC-MS and NMR. $C_{28}H_{17}NO_2$: M+399.1

$^1$H NMR (CDCl$_3$; 400 MHz) δ (ppm) 8.68-8.66 (d, 1H), 8.49-8.42 (m, 6H), 8.29-8.27 (d, 1H), 8.09-8.06 (d, 1H),

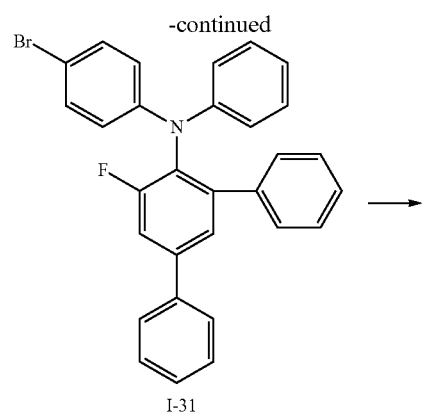

I-31

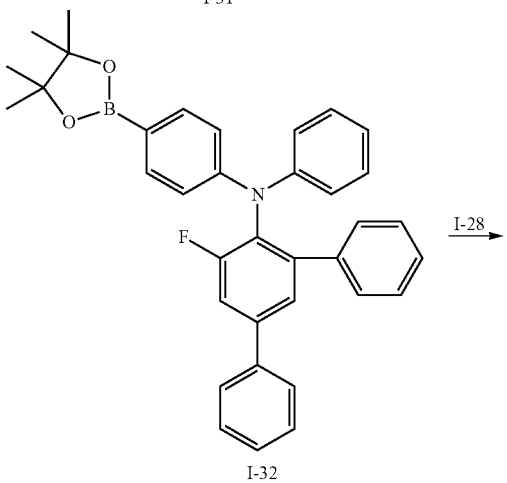

I-32

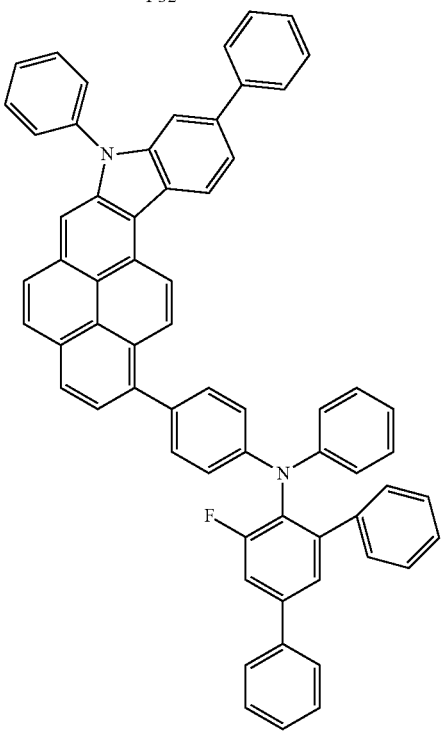

75

Synthesis of Intermediate I-29

5.38 g (20.0 mmol) of 2,4-dibromo-6-fluoro-phenylamine, 5.36 g (44.0 mmol) of phenylboronic acid, 1.15 g (1.0 mmol) of Pd(PPh$_3$)$_4$, and 8.29 g (60.0 mmol) of K$_2$CO$_3$ were dissolved in 80 mL of a mixed solution THF/H$_2$O (2:1) to obtain a solution, which was then stirred at about 70° C. for about 5 hours. The reaction solution was cooled to room temperature, followed by three times of extraction with 60 mL of water and 60 mL of diethylether. The organic phase was collected, and was dried using magnesium sulfate to evaporate the solvent. The residue was separated and purified using silica gel column chromatography to obtain 4.11 g of Intermediate I-29 (Yield: 78%) This compound was identified using LC-MS and NMR. C$_{18}$H$_{14}$FN: M+263.1

$^1$H NMR (CD$_2$Cl$_2$, 400 MHz) δ (ppm) 7.62-7.57 (t, 1H), 7.56-7.54 (m, 1H), 7.51-7.47 (m, 4H), 7.44-7.37 (m, 3H), 7.31-7.30 (m, 1H), 7.29-7.26 (m, 1H), 7.23-7.22 (m, 1H), 3.94 (s, 2H)

Synthesis of Intermediate I-30

2.44 g of Intermediate I-30 was synthesized from Intermediate I-29, in the same manner as in the synthesis of Intermediate I-8 (Yield: 72%). This compound was identified using LC-MS and NMR. C$_{24}$H$_{18}$FN: M+339.1

$^1$H NMR (CDCl$_3$, 400 MHz) δ (ppm) 7.79-7.78 (m, 1H), 7.63-7.61 (m, 2H), 7.57-7.54 (m, 4H), 7.42-7.38 (m, 2H), 7.28-7.21 (m, 3H), 7.12-7.10 (dt, 2H), 7.03-7.02 (d, 2H), 6.89-6.85 (dt, 1H), 4.23 (s, 1H)

Synthesis of Intermediate I-31

3.31 g of Intermediate I-31 was synthesized from Intermediate I-30 in the same manner as in the synthesis of Intermediate I-9 (Yield: 67%). This compound was identified using LC-MS and NMR. C$_{30}$H$_{21}$BrFN: M+493.1

$^1$H NMR (CDCl$_3$, 400 MHz) δ (ppm), 7.77-7.63 (m, 2H), 7.50-7.36 (m, 5H), 7.23-7.17 (m, 7H), 7.14-7.09 (dt, 2H), 6.92-6.84 (m, 3H), 6.77-6.72 (m, 2H)

Synthesis of Intermediate I-32

4.28 g of Intermediate I-32 was synthesized from Intermediate I-31 in the same manner as in the synthesis of Intermediate I-10 (Yield: 79%). This compound was identified using LC-MS and NMR. C$_{36}$H$_{33}$BFNO$_2$: M+541.3

$^1$H NMR (CDCl$_3$, 400 MHz) δ (ppm) 7.63-7.58 (m, 4H), 7.46-7.33 (m, 5H), 7.17-7.13 (m, 5H), 7.07-7.02 (m, 2H), 6.89-6.86 (dd, 3H), 6.82-6.78 (m, 2H)

Synthesis of Compound 75

3.26 g of Compound 75 was synthesized from Intermediate I-32 and Intermediate I-28 in the same manner as in the synthesis of Compound 3 (Yield: 76%). This compound was identified using LC-MS and NMR. C$_{64}$H$_{41}$FN$_2$: M+856.3

$^1$H NMR (CDCl$_3$, 400 MHz) δ (ppm) 9.06-9.04 (d, 1H), 8.50-8.48 (m, 2H), 8.39-8.37 (d, 1H), 8.33-8.27 (dd, 2H), 8.19-8.10 (m, 6H), 7.92-7.85 (m, 4H), 7.71-7.70 (dd, 2H), 7.61-7.50 (m, 9H), 7.46-7.36 (m, 9H), 7.14-7.10 (dt, 1H), 7.09-7.05 (m, 2H), 6.95-6.93 (dd, 2H)

Example 1

To manufacture an anode, a corning 15 Ω/cm$^2$ (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

Then, 2-TNATA, which is a HIL material, was vacuum-deposited on the glass substrate to form a HIL having a thickness of about 600 Å. Then, 4,4'-bis[N-(1-naphthyl)-N-phenylamino]biphenyl (NPB), which is a hole transporting compound, was vacuum-deposited on the HIL to form a HU having a thickness of about 300 Å.

A blue fluorescent host 9,10-di-naphthalene-2-yl-anthracene (ADN) and Compound 3 of Synthesis Example 1, which is a blue fluorescent dopant, were simultaneously deposited on the HU with a weight ratio of 98:2 to form an EML having a thickness of 300 Å.

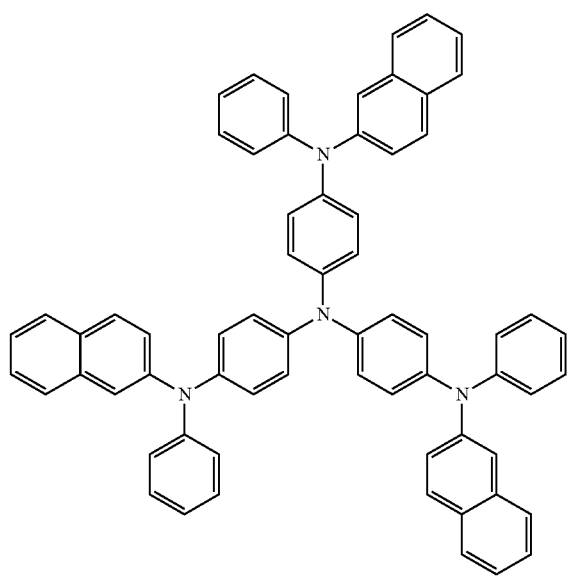

2-TNATA

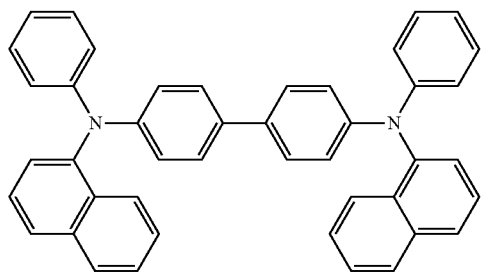

NPB

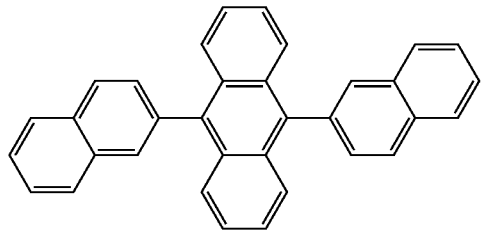

ADN

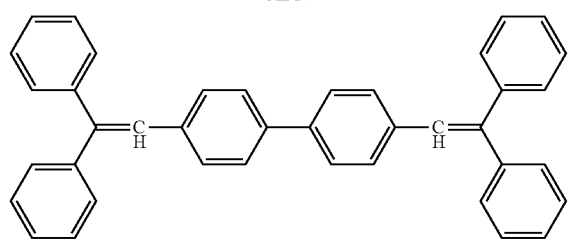

DPVBi

Then, Alq3 was deposited on the EML to form an En having a thickness of 300 Å, and then LiF, which is a halogenated alkali metal, was deposited on the ETL to form an EIL having a thickness of 10 Å. Then, Al was vacuum-deposited on the EIL to form a cathode having a thickness of 3000 Å, thereby forming an LiF/Al electrode and completing the manufacture of an organic light-emitting device.

The organic light-emitting device had a driving voltage of 6.45V at a current density of 50 mA/cm², a high luminosity of 2965 cd/m', a luminescent efficiency of 5.93 cd/A, and a half-lifespan of 275 hours at 100 mA/cm².

Example 2

An organic light-emitting device was manufactured in the same manner as in Example 1, except that Compound 5 was used, instead of Compound 3, to form the EML.

The organic light-emitting device had a driving voltage of 6.46V at a current density of 50 mA/cm', a high luminosity of 2940 cd/n1', a luminescent efficiency of 5.88 cd/A, and a half-lifespan of 267 hours at 100 mA/cm².

Example 3

An organic light-emitting device was manufactured in the same manner as in Example 1, except that Compound 11 was used, instead of Compound 3, to form the EML.

The organic light-emitting device had a driving voltage of 6.32V at a current density of 50 mA/cm', a high luminosity of 2985 cd/m', a luminescent efficiency of 5.97 cd/A, and a half-lifespan of 180 hours at 100 mA/cm².

Example 4

An organic light-emitting device was manufactured in the same manner as in Example 1, except that Compound 21 was used, instead of Compound 3, to form the EML.

The organic light-emitting device had a driving voltage of 6.45V at a current density of 50 in A/cm', a high luminosity of 2890 cd/m', a luminescent efficiency of 5.78 cd/A, and a half-lifespan of 260 hours at 100 mA/cm².

Example 5

An organic light-emitting device was manufactured in the same manner as in Example 1, except that Compound 24 was used, instead of Compound 3, to form the EML.

The organic light-emitting device had a driving voltage of 6.21V at a current density of 50 mA/cm', a high luminosity of 2560 cd/m', a luminescent efficiency of 5.12 cd/A, and a half-lifespan of 193 hours at 100 mA/cm².

Example 6

An organic light-emitting device was manufactured in the same manner as in Example 1, except that Compound 40 was used, instead of Compound 3, to form the EML.

The organic light-emitting device had a driving voltage of 6.41V at a current density of 50 mA/cm², a high luminosity of 2835 cd/m², a luminescent efficiency of 5.67 cd/A, and a half-lifespan of 232 hours at 100 mA/cm².

Example 7

An organic light-emitting device was manufactured in the same manner as in Example 1, except that Compound 58 was used, instead of Compound 3, to form the EML.

The organic light-emitting device had a driving voltage of 6.46V at a current density of 50 mA/cm', a high luminosity of 2745 cd/m', a luminescent efficiency of 5.49 cd/A, and a half-lifespan of 217 hours at 100 mA/cm².

Example 8

An organic light-emitting device was manufactured in the same manner as in Example 1, except that Compound 63 was used, instead of Compound 3, to form the EML.

The organic light-emitting device had a driving voltage of 6.42V at a current density of 50 mA/cm², a high luminosity of 2855 cd/m', a luminescent efficiency of 5.71 cd/A, and a half-lifespan of 225 hours at 100 mA/cm².

Example 9

An organic light-emitting device was manufactured in the same manner as in Example 1, except that Compound 75 was used, instead of Compound 3, to form the EML.

The organic light-emitting device had a driving voltage of 6.47V at a current density of 50 mA/cm², a high luminosity of 2945 cd/m², a luminescent efficiency of 5.89 cd/A, and a half-lifespan of 209 hours at 100 m/cm².

Comparative Example 1

An organic light-emitting device was manufactured in the same manner as in Example 1, except that a blue fluorescent dopant 1,4-bis-(2,2-diphenylvinyl)biphenyl (DPVBi) was used, instead of Compound 3, to form the EML.

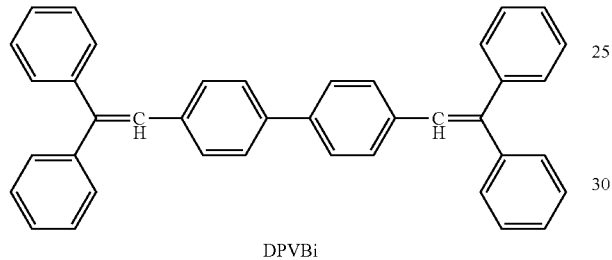

DPVBi

The organic light-emitting device had a driving voltage of 7.85V at a current density of 50 mA/cm', a luminosity of 1560 cd/m², a luminescent efficiency of 3.12 cd/A, and a half-lifespan of 113 hours at 100 mA/cm².

The organic light-emitting devices manufactured using the heterocyclic compounds represented by Formula 1 according to embodiments as blue dopants for EML had improved driving voltages and much higher I-V-L characteristics, as compared to those manufactured using DPVBi. In particular, the organic light-emitting devices according to the embodiments had markedly improved lifetimes. These results are shown in Table 1 below.

istics, and may be used to prevent crystallization due to high glass transition temperatures ($T_g$). The heterocyclic compounds may also be used as electron transporting materials for most color-fluorescent and phosphorescent devices, such as red, green, blue, and white fluorescent and phosphorescent devices, or as red, green, blue or white-light emitting materials. Thus, an organic light-emitting device with high-efficiency, low-driving voltage, high luminance and long lifespan may be manufactured using the heterocylic compounds.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A heterocyclic compound represented by Formula 1 below:

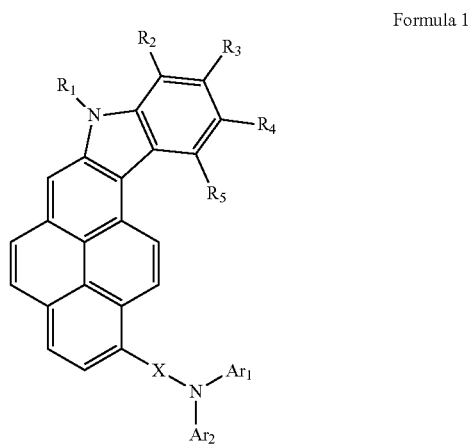

Formula 1 wherein, in Formula 1, $R_1$ through $R_5$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or

TABLE 1

| | EML material | Driving voltage (V) | Current density (mA/cm²) | Luminosity (cd/m²) | Luminescent efficiency (cd/A) | Emitting light color | Half life-span (hr @100 mA/cm²) |
|---|---|---|---|---|---|---|---|
| Example 1 | Compound 3 | 6.45 | 50 | 2,965 | 5.93 | blue | 275 hr |
| Example 2 | Compound 5 | 6.46 | 50 | 2,940 | 5.88 | blue | 267 hr |
| Example 3 | Compound 11 | 6.32 | 50 | 2,985 | 5.97 | blue | 180 hr |
| Example 4 | Compound 21 | 6.45 | 50 | 2,890 | 5.78 | blue | 260 hr |
| Example 5 | Compound 24 | 6.21 | 50 | 2,560 | 5.12 | bluish green | 193 hr |
| Example 6 | Compound 40 | 6.41 | 50 | 2,835 | 5.67 | blue | 232 hr |
| Example 7 | Compound 58 | 6.46 | 50 | 2,745 | 5.49 | blue | 217 hr |
| Example 8 | Compound 63 | 6.42 | 50 | 2,855 | 5.71 | blue | 225 hr |
| Example 9 | Compound 75 | 6.47 | 50 | 2,945 | 5.89 | blue | 209 hr |
| Comparative Example 1 | DPVBi | 7.85 | 50 | 1,560 | 3.12 | blue | 113 hr |

As described above, novel heterocyclic compounds according to the one or more of the above embodiments of the present invention have good electrical characteristics, good charge transporting capabilities and good emission characterunsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a amino group substituted with a $C_5$-$C_{60}$ aryl or $C_3$-$C_{60}$ heteroaryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, or a carboxyl group;

$Ar_1$ and $Ar_2$ are each independently a substituted or unsubstituted $C_3$-$C_{50}$ cycloalkyl group, a substituted or unsubstituted $C_5$-$C_{60}$ aryloxy group, a substituted or unsubstituted $C_5$-$C_{60}$ arythio group, a substituted or unsubstituted $C_5$-$C_{60}$ aryl group, a amino group substituted with a $C_5$-$C_{60}$ aryl or $C_3$-$C_{60}$ heteroaryl group, a substituted or unsubstituted $C_3$-$C_{60}$ heteroaryl group, or a substituted or unsubstituted $C_6$-$C_{60}$ condensed polycyclic group; and X is a divalent linking group represented by —$(Ar_3)_n$— where $Ar_3$ is a substituted or unsubstituted $C_5$-$C_{60}$ arylene group, a substituted or unsubstituted $C_3$-$C_{60}$ heteroarylene group, or a substituted or unsubstituted $C_6$-$C_{60}$ condensed polycyclic group, and n is an integer from 1 to 10, wherein n groups of $Ar_3$ are identical to or different from each other, and at least two adjacent groups of the n $Ar_3$ groups are fused or linked to each other by a single bond.

2. The heterocyclic compound of claim 1, wherein $R_1$ to $R_5$ in Formula 1 are each independently a hydrogen atom, a deuterium atom, a cyano group, a halogen atom, an unsubstituted $C_1$-$C_{20}$ alkyl group, a substituted $C_1$-$C_{20}$ alkyl group with at least one fluorine (—F) substituent, a substituted or unsubstituted $C_5$-$C_{20}$ aryl group, or a substituted or unsubstituted $C_3$-$C_{20}$ heteroaryl group.

3. The heterocyclic compound of claim 1, wherein $R_1$ to $R_5$ in Formula 1 are each independently a hydrogen atom, a deuterium atom, a halogen atom, a cyano group, a substituted or unsubstituted $C_1$-$C_{20}$ alkyl group, or groups represented by Formulae 2a to 2f below:

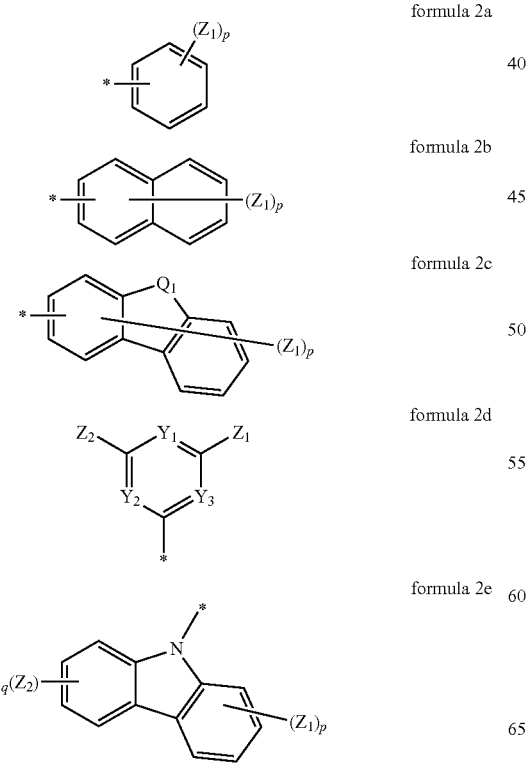

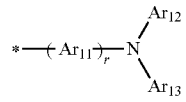

wherein, in Formulae 2a to 2f, $Q_1$ is a linking group represented by —$C(R_6)(R_7)$—, —$N(R_6)$—, —S—, or —O—;

$Y_1$, $Y_2$, and $Y_3$ are each independently a linking group represented by —N= or —$C(R_8)$=;

$Z_1$, $Z_2$, $Ar_{12}$, $Ar_{13}$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

$Ar_{11}$ is a substituted or unsubstituted $C_1$-$C_{20}$ alkylene group, a substituted or unsubstituted $C_5$-$C_{20}$ arylene group, or a substituted or unsubstituted $C_3$-$C_{20}$ heteroarylene group;

p is an integer from 1 to 12;

q is an integer from 1 to 12;

r is an integer from 0 to 5; and

* indicates a binding site.

4. The heterocyclic compound of claim 1, wherein $R_1$ to $R_5$ in Formula 1 are each independently a hydrogen atom, a deuterium atom, a halogen atom, a cyano group, a methyl group, an ethyl group, a propyl group, a butyl group, a pentyl group, or groups represented by Formulae 3a to 3h below:

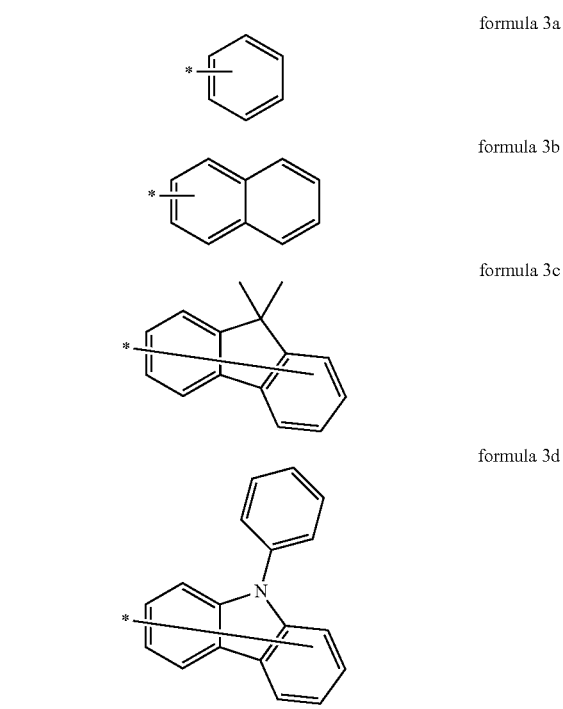

-continued

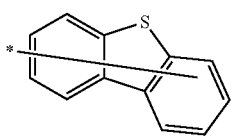
formula 3e

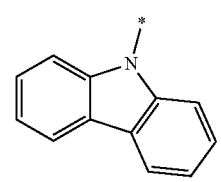
formula 3f

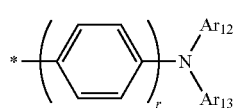
formula 3g

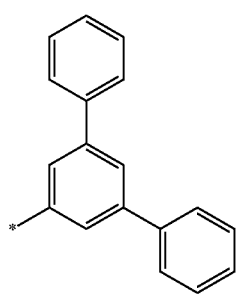
formula 3h wherein in Formula 3a to 3h, $Ar_{12}$ and $Ar_{13}$ are each independently an unsubstituted aryl group, a substituted or unsubstituted $C_3$-$C_{20}$ heteroaryl group, or a substituted or unsubstituted $C_6$-$C_{20}$ condensed polycyclic group;

r is an integer from 0 to 2; and

* indicates a binding site.

5. The heterocyclic compound of claim 1, wherein $R_2$ and $R_5$ in Formula 1 are hydrogen atoms; and $R_1$, $R_3$, and $R_4$ are each independently a hydrogen atom, a deuterium atom, a halogen atom, a cyano group, a methyl group, an ethyl group, a propyl group, a butyl group, a pentyl group, or groups represented by Formulae 3a to 3h below:

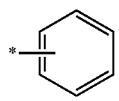
formula 3a

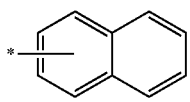
formula 3b

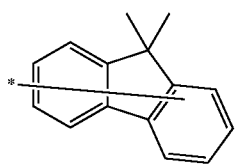
formula 3c

-continued

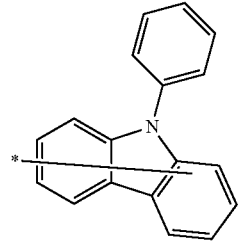
formula 3d

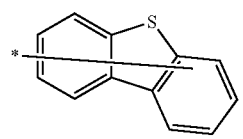
formula 3e

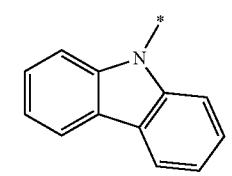
formula 3f

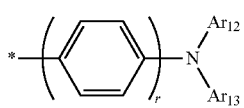
formula 3g

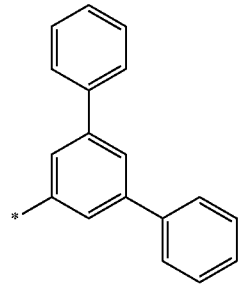
formula 3h wherein, in Formula 3a to 3h, $Ar_{12}$ and $Ar_{13}$ are each independently an unsubstituted aryl group, a substituted or unsubstituted $C_3$-$C_{20}$ heteroaryl group, or a substituted or unsubstituted $C_6$-$C_{20}$ condensed polycyclic group; r is an integer from 0 to 2; and * indicates a binding site.

6. The heterocyclic compound of claim 1, wherein $R_2$ and $R_5$ are hydrogen atoms; and $R_1$, $R_3$ and $R_4$ are each independently a hydrogen, a substituted or unsubstituted $C_1$-$C_{20}$ alkyl group, a substituted or unsubstituted $C_6$-$C_{20}$ aryl group, or a substituted or unsubstituted $C_3$-$C_{20}$ heteroaryl group.

7. The heterocyclic compound of claim 1, wherein $Ar_1$ and $Ar_2$ in Formula 1 are each independently a substituted or unsubstituted $C_1$-$C_{20}$ alkyl group, a substituted or unsubstituted $C_5$-$C_{20}$ aryl group, or a substituted or unsubstituted $C_3$-$C_{20}$ heteroaryl group.

8. The heterocyclic compound of claim 1, wherein $Ar_1$ and $Ar_2$ in Formula 1 are each independently a group represented by one of Formulae 4a to 4d below:

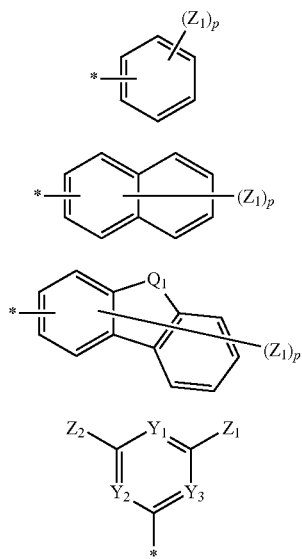

formula 4a formula 4b formula 4c formula 4d wherein, in Formula 4a to 4d, $Q_1$ is a linking group represented by —C($R_6$)($R_7$)—, —N($R_6$)—, —S—, or —O—;

$Y_1$, $Y_2$, and $Y_3$ are each independently a linking group represented by —N= or —C($R_8$)=;

$Z_1$, $Z_2$, $R_6$, $R_7$; and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

p is an integer from 1 to 8; and

* indicates a binding site.

9. The heterocyclic compound of claim 1, wherein $Ar_1$ and $Ar_2$ in Formula 1 are each independently a group represented by one of Formulae 5a to 5i below:

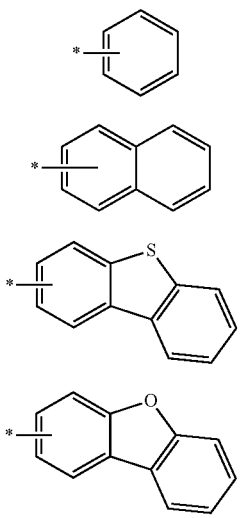

formula 5 formula 5b formula 5c formula 5d

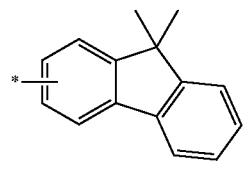

formula 5e

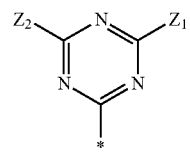

formula 5f

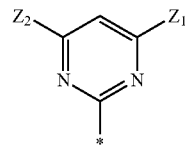

formula 5g

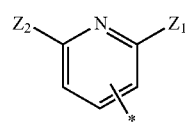

formula 5h

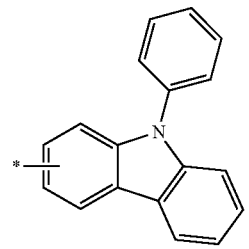

formula 5i wherein $Z_1$ and $Z_2$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, or a substituted or unsubstituted $C_6$-$C_{20}$ condensed polycyclic group; and * indicates a binding site.

10. The heterocyclic compound of claim 1, wherein $Ar_3$ for X in Formula 1 is a substituted or unsubstituted $C_5$-$C_{20}$ arylene group, a substituted or unsubstituted $C_3$-$C_{20}$ heteroarylene group, or a substituted or unsubstituted $C_6$-$C_{20}$ condensed polycyclic group.

11. The heterocyclic compound of claim 1, wherein $Ar_3$ for X in Formula 1 comprises a group represented by one of Formulae 6a to 6e below:

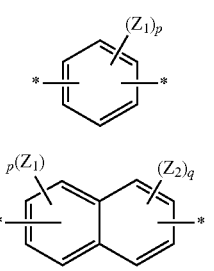

formula 6a formula 6b

-continued

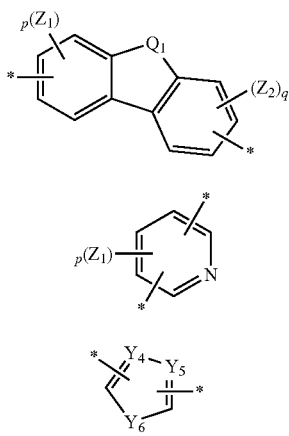

formula 6c formula 6d formula 6e wherein, in Formula 6a to 6e, $Q_1$ is a linking group represented by $-C(R_6)(R_7)-$, $-N(R_6)-$, or $-S-$;

$Y_4$, $Y_5$, and $Y_6$ are each independently a linking group represented by $-N=$ or $-C(R_8)=$, $-S-$, or $-O-$;

$Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

p is an integer from 1 to 8;

q is an integer from 1 to 8; and

* indicates a binding site.

12. The heterocyclic compound of claim 1, wherein n is 1 or 2.

13. The heterocyclic compound of claim 1, wherein X in Formula 1 comprises a group represented by one of Formulae 7a to 7j:

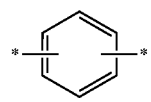

folmula 7a

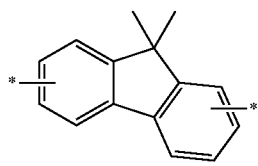

folmula 7b

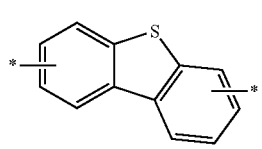

folmula 7c folmula 7d folmula 7e folmula 7f folmula 7g folmula 7h folmula 7i folmula 7j wherein, in Formula 7a to 7j, * indicates a binding site.

14. The heterocyclic compound of claim 1, wherein $R_1$, $R_3$, and $R_4$ in Formula 1 are each independently a hydrogen atom, a deuterium atom, a halogen atom, a cyano group, a methyl group, an ethyl group, a propyl group, a butyl group, a pentyl group, or groups represented by Formulae 3a to 3h below:

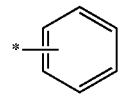

formula 3a

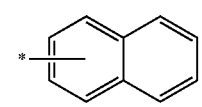

formula 3b

107

-continued formula 3c
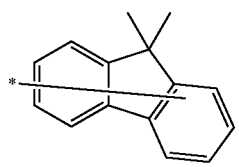

formula 3d
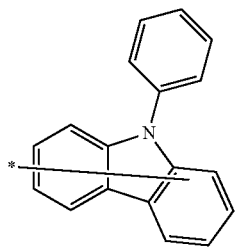

formula 3e
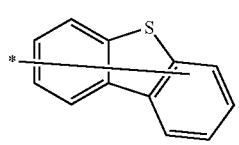

formula 3f
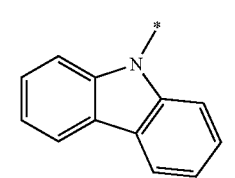

formula 3g
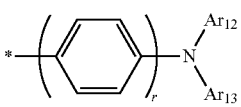

formula 3h
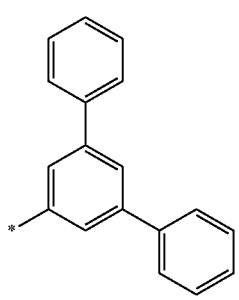

wherein, in Formula 3a to 3h, $Ar_{12}$ and $Ar_{13}$ are each independently an unsubstituted aryl group, a substituted or unsubstituted $C_3$-$C_{20}$ heteroaryl group, or a substituted or unsubstituted $C_6$-$C_{20}$ condensed polycyclic group; r is an integer from 0 to 2, and * indicates a binding site;

$R_2$ and $R_5$ are hydrogen atoms;

$Ar_a$ comprises a group represented by one of Formulae 6a to 6e below:

formula 6a
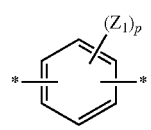

108

-continued formula 6b
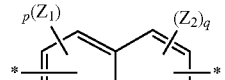

formula 6c
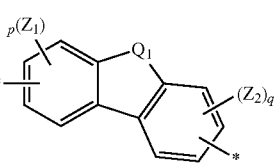

formula 6d
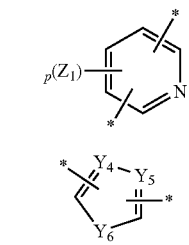

formula 6e
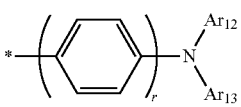

wherein, in Formulae 6a to 6e, $Q_1$ is a linking group represented by —C($R_6$)($R_7$)—, or —S—; $Y_4$, $Y_5$ and $Y_6$ are each independently a linking group represented by —N=, —C($R_8$)=, —S—, or —O—; $Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p is an integer from 1 to 8; q is an integer from 1 to 8; and * indicates a binding site;

n in Formula 1 is 1 or 2; and $Ar_1$ and $Ar_2$ are each independently selected from among groups represented by Formulae 4a to 4d below:

formula 4a
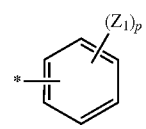

formula 4b
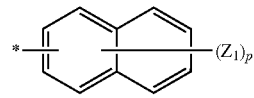

formula 4c
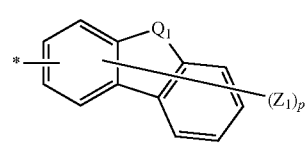

formula 4d
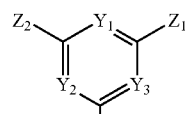

wherein, in Formulae 4a to 4d, $Q_1$ is a linking group represented by —C($R_6$) ($R_7$)—, —N($R_6$)—, —S—, or —O—; $Y_1$, $Y_2$ and $Y_3$ are each independently a linking group represented by —N= or —C($R_8$)=; $Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p is an integer from 1 to 8; and * indicates a binding site.

15. The heterocyclic compound of claim 1, represented by one of the compounds below:

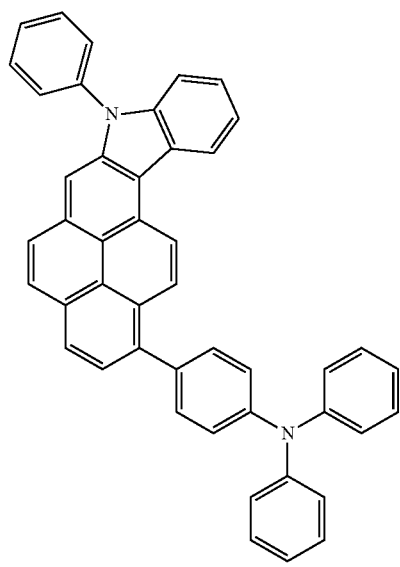

3

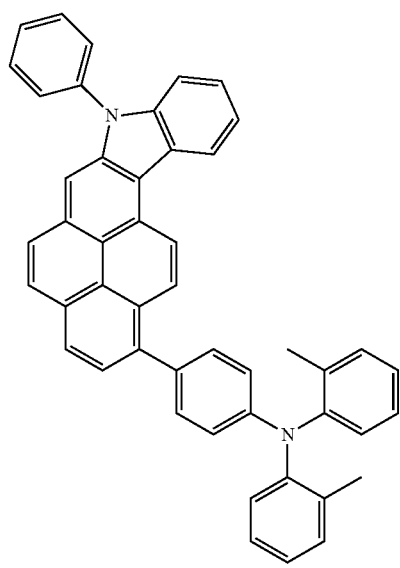

5

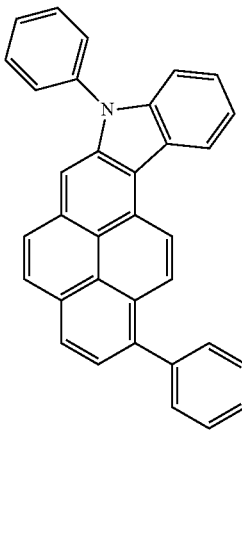

11

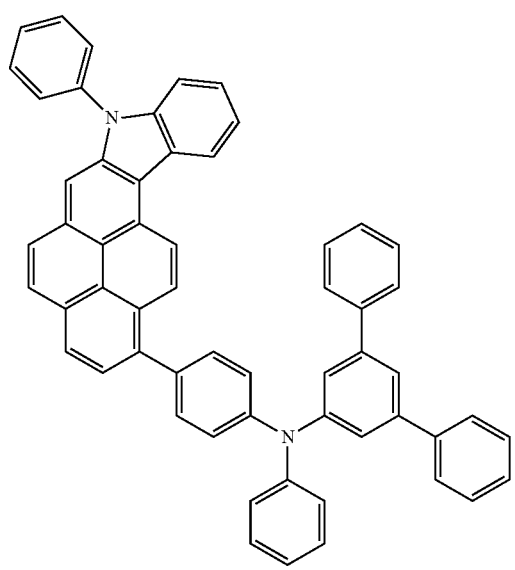

21

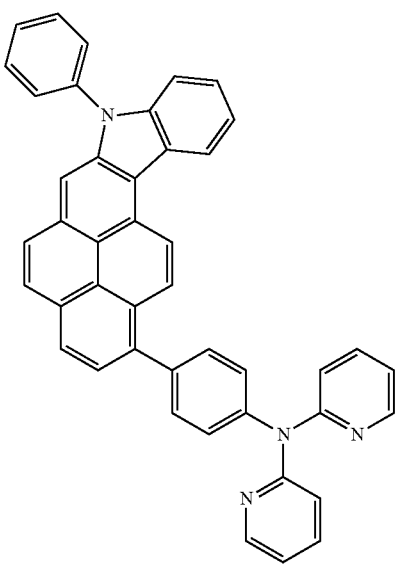

24

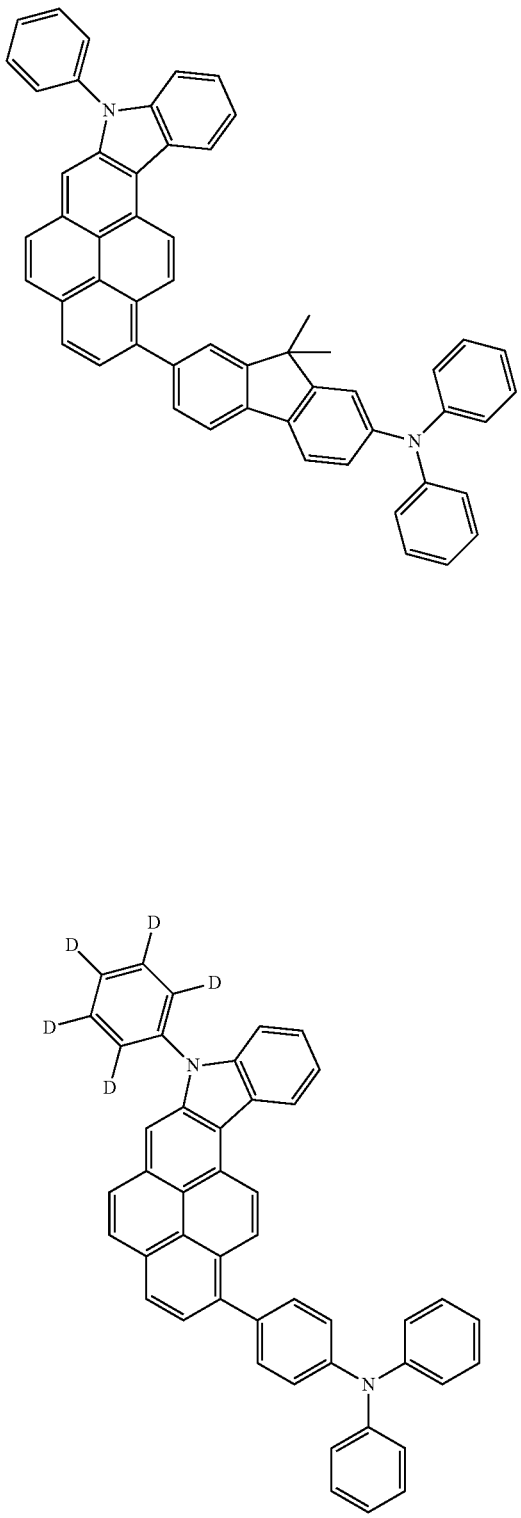

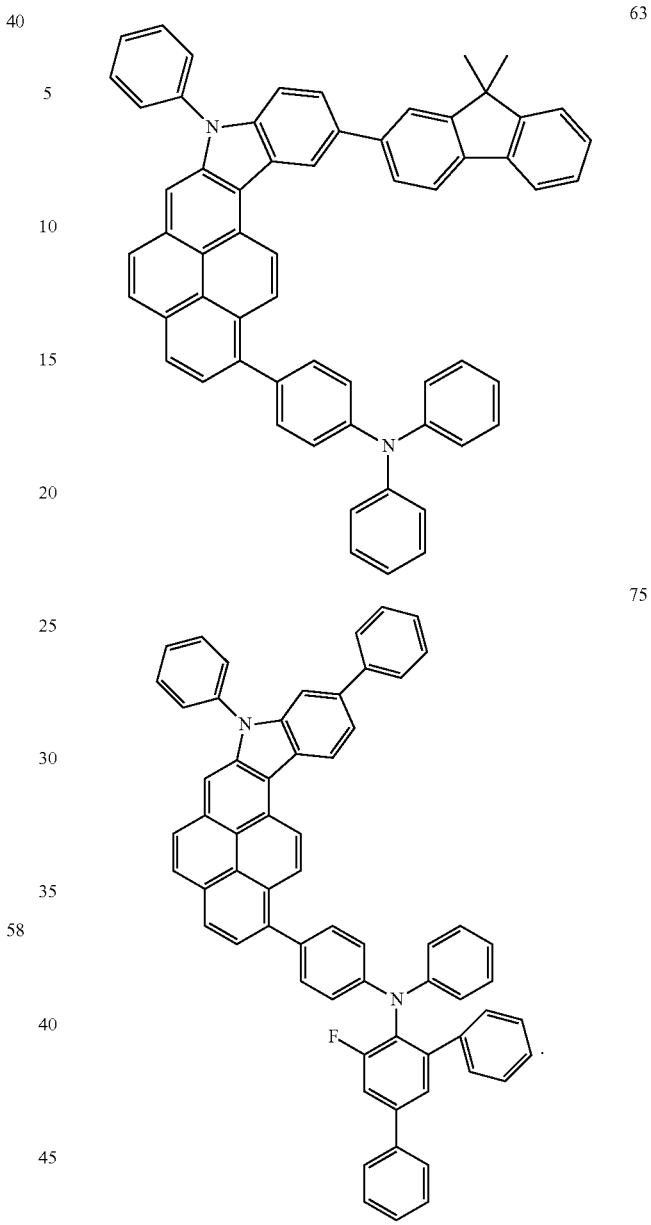

16. An organic light-emitting device comprising:
   a first electrode;
   a second electrode; and
   an organic layer between the first electrode and the second electrode,
   wherein the organic layer comprises a first layer including the heterocyclic compound represented by Formula 1 of claim 1.

17. The organic light-emitting device of claim 16, wherein the first layer comprises a hole injection layer, a hole transport layer, a functional layer having both hole injection and hole transport capabilities, an electron injection layer, an electron transport layer, a functional layer having both electron injection and electron transport capabilities or any combination thereof.

18. The organic light-emitting device of claim 16, wherein the first layer comprises an emission layer, and a heterocyclic compound of Formula 1 is used in the emission layer as a host or a dopant for a fluorescent or phosphorescent device.

19. The organic light-emitting device of claim 16, wherein the first layer comprises an emission layer,
wherein the emission layer comprises an anthracene compound, an arylamine compound, or a styryl compound.

20. The organic light-emitting device of claim 16, wherein the organic layer comprises an emission layer,
wherein the emission layer comprises red, green, blue, and white emission layers, one of which comprises a phosphorescent compound.

21. The organic light-emitting device of claim 16, wherein the first layer comprises a blue emission layer.

22. The organic light-emitting device of claim 16, wherein the first layer comprises a blue emission layer, and a heterocyclic compound of Formula 1, wherein the heterocyclic compound is used as a blue dopant.

23. The organic light-emitting device of claim 16, wherein the organic layer further comprises a hole injection layer, a hole transport layer, a functional layer having both hole injection and transport functions, an emission layer, a hole blocking layer, an electron transport layer, an electron injection layer, and a combination of at least two of these layers.

24. The organic light-emitting device of claim 23, wherein at least one of the hole injection layer, the hole transport layer, and the functional layer having both hole injection and transport functions further comprises a charge-generating material.

25. The organic light-emitting device of claim 23, wherein the electron transport layer comprises an electron transporting organic material and a metal-containing material.

26. The organic light-emitting device of claim 25, wherein the metal-containing material comprises a lithium complex.

27. The organic light-emitting device of claim 16, wherein the first layer is formed of a heterocyclic compound of Formula 1 of claim 1 by using a wet process.

28. A flat panel display device comprising the organic light-emitting device of claim 16, wherein the first electrode of the organic light-emitting device is electrically connected to a source electrode or a drain electrode of a thin-film transistor.

* * * * *